United States Patent
Meyer et al.

(10) Patent No.: US 9,526,822 B2
(45) Date of Patent: Dec. 27, 2016

(54) SODIUM AND BUFFER SOURCE CARTRIDGES FOR USE IN A MODULAR CONTROLLED COMPLIANT FLOW PATH

(71) Applicant: Medtronic, Inc., Minneapolis, MN (US)

(72) Inventors: Thomas E. Meyer, Stillwater, MN (US); David B. Lura, Maple Grove, MN (US); Bryant J. Pudil, Plymouth, MN (US); Martin T. Gerber, Maple Grove, MN (US)

(73) Assignee: Medtronic, Inc., Minneapolis, MN (US)

( * ) Notice: Subject to any disclaimer, the term of this patent is extended or adjusted under 35 U.S.C. 154(b) by 692 days.

(21) Appl. No.: 13/757,722

(22) Filed: Feb. 1, 2013

(65) Prior Publication Data
US 2014/0217030 A1    Aug. 7, 2014

(51) Int. Cl.
*A61M 1/16*    (2006.01)
*A61M 1/36*    (2006.01)

(52) U.S. Cl.
CPC .............. *A61M 1/3621* (2013.01); *A61M 1/16* (2013.01); *A61M 1/165* (2014.02); *A61M 1/1658* (2013.01); *A61M 1/1666* (2014.02); *A61M 1/3627* (2013.01)

(58) Field of Classification Search
CPC ...... A61M 1/16; A61M 1/165; A61M 1/1658; A61M 1/1666; A61M 1/3621; A61M 1/3627
USPC ............................... 210/137, 143, 646, 647
See application file for complete search history.

(56) References Cited

U.S. PATENT DOCUMENTS

| | | |
|---|---|---|
| 3,608,729 A | 9/1971 | Haselden |
| 3,669,878 A | 6/1972 | Marantz |
| 3,669,880 A | 6/1972 | Marantz |
| 3,850,835 A | 11/1974 | Marantz |
| 3,884,808 A | 5/1975 | Scott |
| 3,989,622 A | 11/1976 | Marantz |

(Continued)

FOREIGN PATENT DOCUMENTS

| | | |
|---|---|---|
| EP | 266795 A2 | 11/1987 |
| EP | 1364666 A1 | 11/2003 |

(Continued)

OTHER PUBLICATIONS

Culleton, BF et al. Effect of Frequent Nocturnal Hemodialysis vs. Conventional Hemodialysis on Left Ventricular Mass and Quality of Life. 2007 Journal of the American Medical Association 298 (11), 1291-1299.

(Continued)

*Primary Examiner* — Dirk Bass

(57) ABSTRACT

Systems and methods for using a sodium chloride source and a buffer source such as sodium bicarbonate in a controlled compliant flow path to generate from water a physiologically compatible fluid having a suitable level of a sodium ion and/or a buffer for use in hemodialysis, hemodiafiltration and hemofiltration. The system has a conditioning flow path that has at least a salination valve or salination pump, and at least one container has at least one solute in excess of the solubility of that solute. At least one of the solutes is a buffer source or sodium chloride. The conditioning flow path is in fluid communication with a controlled compliant flow path. The conditioning flow path can selectively meter fluid into and out of the controlled compliant flow path.

57 Claims, 36 Drawing Sheets

(56) References Cited

U.S. PATENT DOCUMENTS

| | | |
|---|---|---|
| 4,060,485 A | 11/1977 | Eaton |
| 4,371,385 A | 2/1983 | Johnson |
| 4,374,382 A | 2/1983 | Markowitz |
| 4,381,999 A | 5/1983 | Boucher |
| 4,460,555 A | 7/1984 | Thompson |
| 4,556,063 A | 12/1985 | Thompson |
| 4,562,751 A | 1/1986 | Nason |
| 4,581,141 A | 4/1986 | Ash |
| 4,650,587 A | 3/1987 | Polak |
| 4,678,408 A | 7/1987 | Mason |
| 4,685,903 A | 8/1987 | Cable |
| 4,750,494 A | 6/1988 | King |
| 4,784,495 A * | 11/1988 | Jonsson ............... A61M 1/1656 137/88 |
| 4,826,663 A | 5/1989 | Alberti |
| 4,828,693 A | 5/1989 | Lindsay |
| 5,080,653 A | 1/1992 | Voss |
| 5,092,886 A | 3/1992 | Dobos-Hardy |
| 5,097,122 A | 3/1992 | Colman |
| 5,127,404 A | 7/1992 | Wyborny |
| 5,284,470 A | 2/1994 | Beltz |
| 5,302,288 A | 4/1994 | Meidl |
| 5,305,745 A | 4/1994 | Zacouto |
| 5,318,750 A | 6/1994 | Lascombes |
| 5,468,388 A | 11/1995 | Goddard |
| 5,591,344 A * | 1/1997 | Kenley ................ A61L 2/04 210/134 |
| 5,683,432 A | 11/1997 | Goedeke |
| 5,762,782 A | 6/1998 | Kenley |
| 5,944,684 A | 8/1999 | Roberts |
| 5,972,223 A * | 10/1999 | Jonsson ............... A61L 2/0023 137/88 |
| 6,048,732 A | 4/2000 | Anslyn |
| 6,052,622 A | 4/2000 | Holstrom |
| 6,058,331 A | 5/2000 | King |
| 6,230,059 B1 | 5/2001 | Duffin |
| 6,248,093 B1 | 6/2001 | Moberg |
| 6,254,567 B1 | 7/2001 | Treu |
| 6,321,101 B1 | 11/2001 | Holstrom |
| 6,362,591 B1 | 3/2002 | Moberg |
| 6,363,279 B1 | 3/2002 | Ben-Haim |
| 6,554,798 B1 | 4/2003 | Mann |
| 6,555,986 B2 | 4/2003 | Moberg |
| 6,589,229 B1 | 7/2003 | Connelly |
| 6,602,399 B1 | 8/2003 | Fromherz |
| 6,627,164 B1 | 9/2003 | Wong |
| 6,676,608 B1 | 1/2004 | Keren |
| 6,711,439 B1 | 3/2004 | Bradley |
| 6,818,196 B2 | 11/2004 | Wong |
| 6,878,283 B2 | 4/2005 | Thompson |
| 6,960,179 B2 | 11/2005 | Gura |
| 7,077,819 B1 | 7/2006 | Goldau |
| 7,208,092 B2 | 4/2007 | Micheli |
| 7,276,042 B2 | 10/2007 | Polaschegg |
| 7,566,432 B2 | 7/2009 | Wong |
| 7,575,564 B2 | 8/2009 | Childers |
| 7,674,231 B2 | 3/2010 | McCombie |
| 7,704,361 B2 | 4/2010 | Garde |
| 7,736,507 B2 | 6/2010 | Wong |
| 7,754,852 B2 | 7/2010 | Burnett |
| 7,756,572 B1 | 7/2010 | Fard |
| 7,776,210 B2 | 8/2010 | Rosenbaum et al. |
| 7,794,141 B2 | 9/2010 | Perry |
| 7,850,635 B2 | 12/2010 | Polaschegg |
| 7,867,214 B2 | 1/2011 | Childers |
| 7,922,686 B2 | 4/2011 | Childers |
| 7,922,911 B2 | 4/2011 | Micheli |
| 7,947,179 B2 | 5/2011 | Rosenbaum et al. |
| 7,967,022 B2 | 6/2011 | Grant |
| 7,981,082 B2 | 7/2011 | Wang |
| 8,034,161 B2 | 10/2011 | Gura |
| 8,070,709 B2 | 12/2011 | Childers |
| 8,096,969 B2 | 1/2012 | Roberts |
| 8,183,046 B2 | 5/2012 | Lu |
| 8,187,250 B2 | 5/2012 | Roberts |
| 8,246,826 B2 | 8/2012 | Wilt |
| 8,273,049 B2 | 9/2012 | Demers |
| 8,292,594 B2 | 10/2012 | Tracey |
| 8,313,642 B2 | 11/2012 | Yu |
| 8,317,492 B2 | 11/2012 | Demers |
| 8,357,113 B2 | 1/2013 | Childers |
| 8,366,316 B2 | 2/2013 | Kamen |
| 8,366,655 B2 | 2/2013 | Kamen |
| 8,409,441 B2 | 4/2013 | Wilt |
| 8,499,780 B2 | 8/2013 | Wilt |
| 8,518,260 B2 | 8/2013 | Raimann |
| 8,535,525 B2 | 9/2013 | Heyes |
| 8,580,112 B2 | 11/2013 | Updyke |
| 8,597,227 B2 | 12/2013 | Childers |
| 8,696,626 B2 | 4/2014 | Kirsch |
| 2002/0042561 A1 | 4/2002 | Schulman |
| 2002/0112609 A1 | 8/2002 | Wong |
| 2003/0080059 A1 | 5/2003 | Peterson |
| 2003/0097086 A1 | 5/2003 | Gura |
| 2003/0105435 A1 | 6/2003 | Taylor |
| 2003/0114787 A1 | 6/2003 | Gura |
| 2004/0019312 A1 | 1/2004 | Childers |
| 2004/0099593 A1 | 5/2004 | DePaolis |
| 2004/0147900 A1 | 7/2004 | Polaschegg |
| 2004/0215090 A1 | 10/2004 | Erkkila |
| 2005/0065760 A1 | 3/2005 | Murtfeldt |
| 2005/0113796 A1 | 5/2005 | Taylor |
| 2005/0126961 A1 | 6/2005 | Bissler |
| 2005/0126998 A1 | 6/2005 | Childers |
| 2005/0131332 A1 * | 6/2005 | Kelly ................ A61M 1/1696 604/4.01 |
| 2005/0150832 A1 | 7/2005 | Tsukamoto |
| 2005/0234381 A1 | 10/2005 | Niemetz |
| 2005/0236330 A1 | 10/2005 | Nier |
| 2005/0274658 A1 | 12/2005 | Rosenbaum et al. |
| 2006/0025661 A1 | 2/2006 | Sweeney |
| 2006/0195064 A1 | 8/2006 | Plahey |
| 2006/0217771 A1 | 9/2006 | Soykan |
| 2006/0226079 A1 | 10/2006 | Mori |
| 2006/0241709 A1 | 10/2006 | Soykan |
| 2006/0264894 A1 | 11/2006 | Moberg |
| 2007/0007208 A1 | 1/2007 | Brugger |
| 2007/0066928 A1 | 3/2007 | Lannoy |
| 2007/0138011 A1 | 6/2007 | Hofmann |
| 2007/0175827 A1 | 8/2007 | Wariar |
| 2007/0179431 A1 | 8/2007 | Roberts et al. |
| 2007/0215545 A1 | 9/2007 | Bissler |
| 2007/0255250 A1 | 11/2007 | Moberg |
| 2008/0006570 A1 | 1/2008 | Gura |
| 2008/0021337 A1 | 1/2008 | Li |
| 2008/0053905 A9 | 3/2008 | Brugger |
| 2008/0067132 A1 | 3/2008 | Ross |
| 2008/0215247 A1 | 9/2008 | Tonelli |
| 2009/0020471 A1 | 1/2009 | Tsukamoto |
| 2009/0101577 A1 | 4/2009 | Fulkerson |
| 2009/0127193 A1 | 5/2009 | Updyke |
| 2009/0275849 A1 | 11/2009 | Stewart |
| 2009/0275883 A1 | 11/2009 | Chapman |
| 2009/0281484 A1 | 11/2009 | Childers |
| 2009/0282980 A1 | 11/2009 | Gura |
| 2010/0004588 A1 | 1/2010 | Yeh |
| 2010/0010429 A1 | 1/2010 | Childers |
| 2010/0078381 A1 | 4/2010 | Merchant |
| 2010/0078387 A1 | 4/2010 | Wong |
| 2010/0084330 A1 | 4/2010 | Wong |
| 2010/0094158 A1 | 4/2010 | Solem |
| 2010/0114012 A1 | 5/2010 | Sandford |
| 2010/0137693 A1 | 6/2010 | Porras |
| 2010/0168546 A1 | 7/2010 | Kamath |
| 2010/0217181 A1 | 8/2010 | Roberts |
| 2010/0224492 A1 | 9/2010 | Ding |
| 2010/0234795 A1 | 9/2010 | Wallenas |
| 2010/0241045 A1 | 9/2010 | Kelly |
| 2011/0017665 A1 | 1/2011 | Updyke |
| 2011/0066043 A1 | 3/2011 | Banet |
| 2011/0077574 A1 | 3/2011 | Sigg |
| 2011/0079558 A1 | 4/2011 | Raimann |
| 2011/0087187 A1 | 4/2011 | Beck |
| 2011/0130666 A1 | 6/2011 | Dong |

(56) References Cited

U.S. PATENT DOCUMENTS

| | | |
|---|---|---|
| 2011/0184340 A1 | 7/2011 | Tan |
| 2011/0272337 A1 | 11/2011 | Palmer |
| 2012/0016228 A1 | 1/2012 | Kroh |
| 2012/0083729 A1 | 4/2012 | Childers |
| 2012/0085707 A1 | 4/2012 | Beiriger |
| 2012/0115248 A1 | 5/2012 | Ansyln |
| 2012/0220528 A1 | 8/2012 | VanAntwerp |
| 2012/0258546 A1 | 10/2012 | Marran |
| 2012/0273415 A1 | 11/2012 | Gerber |
| 2012/0273420 A1 | 11/2012 | Gerber |
| 2012/0277546 A1 | 11/2012 | Soykan et al. |
| 2012/0277551 A1 | 11/2012 | Gerber |
| 2012/0277552 A1 | 11/2012 | Gerber |
| 2012/0277604 A1 | 11/2012 | Gerber |
| 2012/0277650 A1 | 11/2012 | Gerber |
| 2012/0277655 A1 | 11/2012 | Gerber |
| 2012/0277722 A1 | 11/2012 | Gerber |
| 2013/0037465 A1 | 2/2013 | Heyes |
| 2013/0199998 A1 | 8/2013 | Kelly |
| 2013/0213890 A1 | 8/2013 | Kelly |
| 2013/0274642 A1 | 10/2013 | Soykan |
| 2013/0324915 A1 | 12/2013 | (Krensky) Britton |
| 2013/0330208 A1 | 12/2013 | Ly |
| 2013/0331774 A1 | 12/2013 | Farrell |
| 2014/0018728 A1 | 1/2014 | Plahey |
| 2014/0042092 A1 | 2/2014 | Akonur |
| 2014/0088442 A1 | 3/2014 | Soykan et al. |
| 2014/0110340 A1 | 4/2014 | White |
| 2014/0110341 A1 | 4/2014 | White |
| 2014/0158538 A1 | 6/2014 | Collier |
| 2014/0158588 A1 | 6/2014 | Pudil |
| 2014/0158623 A1 | 6/2014 | Pudil |
| 2014/0190876 A1 | 7/2014 | Meyer |
| 2014/0220699 A1 | 8/2014 | Pudil |

FOREIGN PATENT DOCUMENTS

| | | |
|---|---|---|
| EP | 0906768 B1 | 2/2004 |
| EP | 1450879 | 10/2008 |
| EP | 1592494 B1 | 6/2009 |
| EP | 2100553 A1 | 9/2009 |
| EP | 2575827 A2 | 12/2010 |
| EP | 2576453 A2 | 12/2011 |
| EP | 2701580 | 11/2012 |
| EP | 2701595 | 11/2012 |
| EP | 1345856 B1 | 3/2013 |
| EP | 2344220 B1 | 4/2013 |
| EP | 2701596 | 3/2014 |
| JP | 5099464 | 10/2012 |
| WO | 9937342 | 7/1999 |
| WO | 0057935 | 10/2000 |
| WO | 0066197 A1 | 11/2000 |
| WO | 0170307 A1 | 9/2001 |
| WO | 0185295 A2 | 9/2001 |
| WO | 03043677 A2 | 5/2003 |
| WO | 03043680 | 5/2003 |
| WO | 03051422 A2 | 6/2003 |
| WO | 2004008826 | 1/2004 |
| WO | 2004009156 | 1/2004 |
| WO | 2004030716 A2 | 4/2004 |
| WO | 2004030717 A2 | 4/2004 |
| WO | 2004064616 A2 | 8/2004 |
| WO | 2005123230 A2 | 12/2005 |
| WO | 2007089855 A2 | 8/2007 |
| WO | 2009026603 | 3/2009 |
| WO | 2009026603 A1 | 3/2009 |
| WO | 2009157877 | 12/2009 |
| WO | 2009157878 | 12/2009 |
| WO | 2010028860 | 3/2010 |
| WO | 2010028860 A1 | 3/2010 |
| WO | 2011025705 A1 | 3/2011 |
| WO | 2012148781 | 11/2012 |
| WO | 2012148786 | 11/2012 |
| WO | 2012148789 | 11/2012 |
| WO | 2012162515 A2 | 11/2012 |
| WO | 2012172398 | 12/2012 |
| WO | 2013019179 A1 | 2/2013 |
| WO | 2013019994 | 2/2013 |
| WO | 2013025844 | 2/2013 |
| WO | 2013028809 A3 | 2/2013 |
| WO | 2013103607 A1 | 7/2013 |
| WO | 2013103906 | 7/2013 |
| WO | 2013114063 A | 8/2013 |
| WO | 2013121162 A1 | 8/2013 |
| WO | 2014066254 | 5/2014 |
| WO | 2014066255 | 5/2014 |
| WO | 2014077082 | 5/2014 |
| WO | 2014121162 | 8/2014 |
| WO | 2014121163 | 8/2014 |
| WO | 2014121167 | 8/2014 |
| WO | 2014121169 | 8/2014 |

OTHER PUBLICATIONS

Leifer, I., et al., A Study on the Temperature Variation of Rise Velocity for Large Clean Bubbles, J. Atmospheric & Oceanic Tech., vol. 17, pp. 1392-1402.

Talaia, MAR, Terminal Velocity of a Bubble Rise in a Liquid Column, Talaia, World Acad. of Sci., Engineering & Tech., vol. 28, pp. 264-268.

The FHN Trial Group. In-Center. Hemodialysis Six Times per Week versus Three Times per Week, New England Journal of Medicine, 2010.

U.S. Appl. No. 13/757,693, filed Feb. 1, 2013.

PCT/US2014/014357 International Search Report and Written Opinion.

U.S. Appl. No. 13/757,722, filed Feb. 1, 2013.

U.S. Appl. No. 13/757,794, filed Feb. 2, 2012.

U.S. Appl. No. 13/791,755, filed Mar. 8, 2013.

U.S. Appl. No. 13/757,792, filed Feb. 2, 2013.

U.S. Appl. No. 13/837,287, filed Mar. 15, 2013.

U.S. Appl. No. 13/757,794, filed Feb. 2, 2013.

Bleyer, et. al., Sudden and cardiac death rates in hemodialysis patients, Kidney International, 1999, 1553-1559 : 55.

MacLean, et, al., Effects of hindlimb contraction on pressor and muscle interstitial metabolite responses in the cat, J. App. Physiol., 1998, 1583-1592, 85(4).

Overgaard, et. al., Activity-induced recovery of excitability in K+-depressed rat soieus muscle, Am. J. Physiol. Regulatory integrative Comp. Physiol., 2001, R48-R55, vol. 280.

Overgaard. et. al., Relations between excitability and contractility in rate soleus'muscle: role of the NA+—K+ pump and NA+—K—S gradients. Journal of Physiology, 1999, 215-225, 518(1).

PCT/US2012/034330, International Search Report, Aug. 28, 2012.

PCT/US2012/034332, International Search Report, Jul. 5, 2012.

Roberts M, The regenerative dialysis (REDY) sorbent system. Nephrology, 1998, 275-278:4.

Ronco, et. al., "Cardiorenal Syndrome", J. Am. Coll. Cardiol., 2008, 1527-1539: 52.

Siegenthalar, et. al., Pulmonary fluid status monitoring with intrathoracic impedance, Journal of Clinical Monitoring and Computing, 2010, 449-451 : 24.

U.S. Appl. No. 60/650,497.

U.S. Appl. No. 61/480,544.

Wang, Fundamentals of intrathoracic impedance monitoring in heart failure, Am. J. Cardiology, 2007, 3G-10G : Suppl.

Weiner, et. al., Article: Cardiac Function and Cardiovascular Disease in Chronic Kidney Disease, Book: Primer on Kidney Diseases (Author: Greenberg, et al), 2009,499-505, 5th Ed., Saunders Elsevier, Philadelphia, PA.

Wang, Fundamentals of intrathoracic impedance monitoring in heart failure, Am. J. Cardiology, 2007, 3G-310: Suppl.

Brynda, et. al., The detection of toman 2-microglcbuiin by grating coupler immunosensor with three dimensional antibody networks. Biosensors & Bioelectronics, 1999, 363-368, 14(4).

Hemametrics, Crit-Line Hematocrit Accuracy, 2003, 1-5, vol. 1, Tech Note No. 11 (Rev. D).

(56) References Cited

OTHER PUBLICATIONS

Lima, et. al., An electrochemical sensor based on nanostructure hollsndite-type manganese oxide for detection of potassium ion, Sensors, 2009, 6613-8625, 9.
Nedelkov, et. al., Design of buffer exchange surfaces and sensor chips for biosensor chip mass spectrometry, Proteomics, 2002, 441-446, 2(4).
PCT/US/2012/034327, International Search Report, Aug. 13, 2013.
PCT/US/2012/034329, International Search Report, Dec. 3, 2012.
PCT/US2012/034331, International Search Report, Jul. 9, 2012.
PCT/US2012/034334, International Search Report, Jul. 6, 2012.
PCT/US2012/034335, International Search Report, Sep. 5, 2012.
Redfield, et. al, "Restoration of renal response to atria! natriuretic factor in experimental low-output heat failure", Am. J. Physiol., 1989, R917-923 : 257.
Rogoza, et. al., Validation of A&D UA-767 device for the self-measurement of blood pressure, Blood Pressure Monitoring, 2000, 227-231, 5(4).
Secemsky, et. al, High prevalence of cardiac autonomic dysfunction and T-wave alternans in dialysis patients. Heart Rhythm, Apr. 2011, 592-598 : vol. 8, No. 4.
Wei, et. al., Fullerene-cryptand coated piezoelectric crystal urea sensor based on urease, Analytica Chimica Acta, 2001,77-85:437.
Zhong, et. al., Miniature urea sensor based on H(+)-ion sensitive field effect transistor and its application in clinical analysis, Chin. J. Biotechnol., 1992, 57-65. 8(1).
Coast, et al. 1990, An approach to Cardiac Arrhythmia analysis Using Hidden Markov Models, IEEE Transactions on Biomedical Engineering. 1990, 37(9):826-835.

U.S. Appl. No. 13/368,225.
U.S. Appl. No. 13/424,533.
U.S. Appl. No. 13/424,467.
U.S. Appl. No. 13/424,454.
U.S. Appl. No. 13/424,490.
U.S. Appl. No. 13/424,517.
U.S. Appl. No. 61/480,532.
PCT/US2012/034330, International Preliminary Report on Patentability, Oct. 29, 2013.
PCT Application, PCT/US20013/020404, filed Jan. 4, 2013.
U.S. Appl. No. 14/261,651, filed Apr. 25, 2014.
U.S. Appl. No. 13/836,973, filed Mar. 15, 2013.
U.S. Appl. No. 14/259,655, filed Apr. 23, 2014.
U.S. Appl. No. 14/259,589, filed Apr. 23, 2014.
PCT/US2012/034333, International Preliminary Report on Patentability, Oct. 29, 2013.
PCT/US2012/034333, International Search Report, Aug. 29, 2013.
U.S. Appl. No. 13/424,429.
U.S. Appl. No. 13/424,479.
U.S. Appl. No. 13/424,525.
U.S. Appl. No. 61/480,528.
U.S. Appl. No. 61/480,530.
U.S. Appl. No. 61/480,535.
U.S. Appl. No. 61/480,539.
U.S. Appl. No. 61/480,541.
ISA Invitation to Pay Additional Fees, PCT/US2012/034323 mailed Aug. 2, 2012.

\* cited by examiner

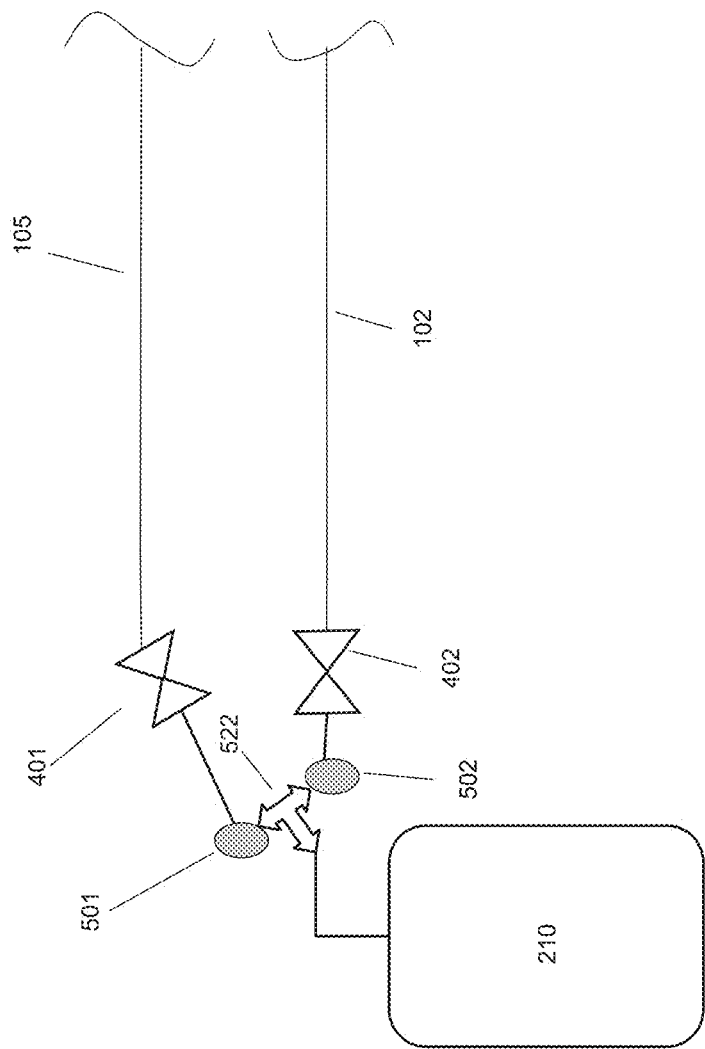

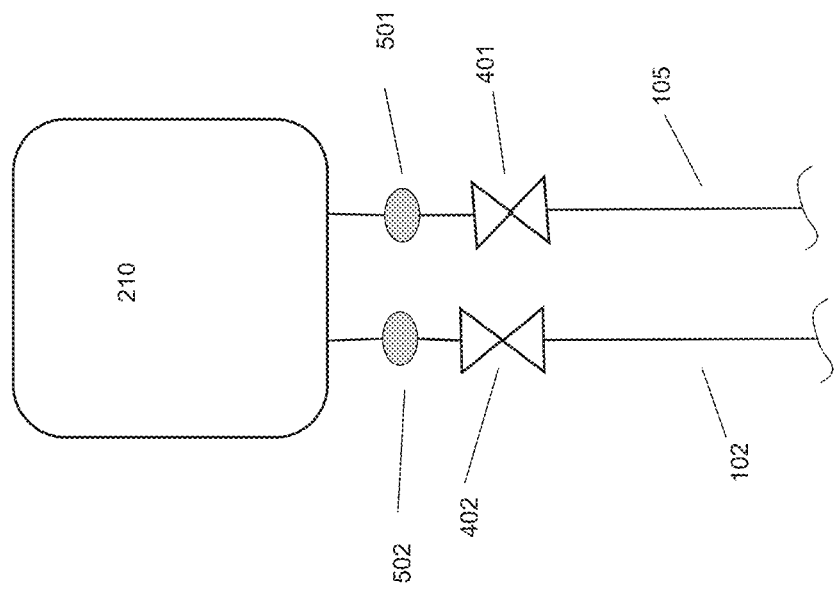

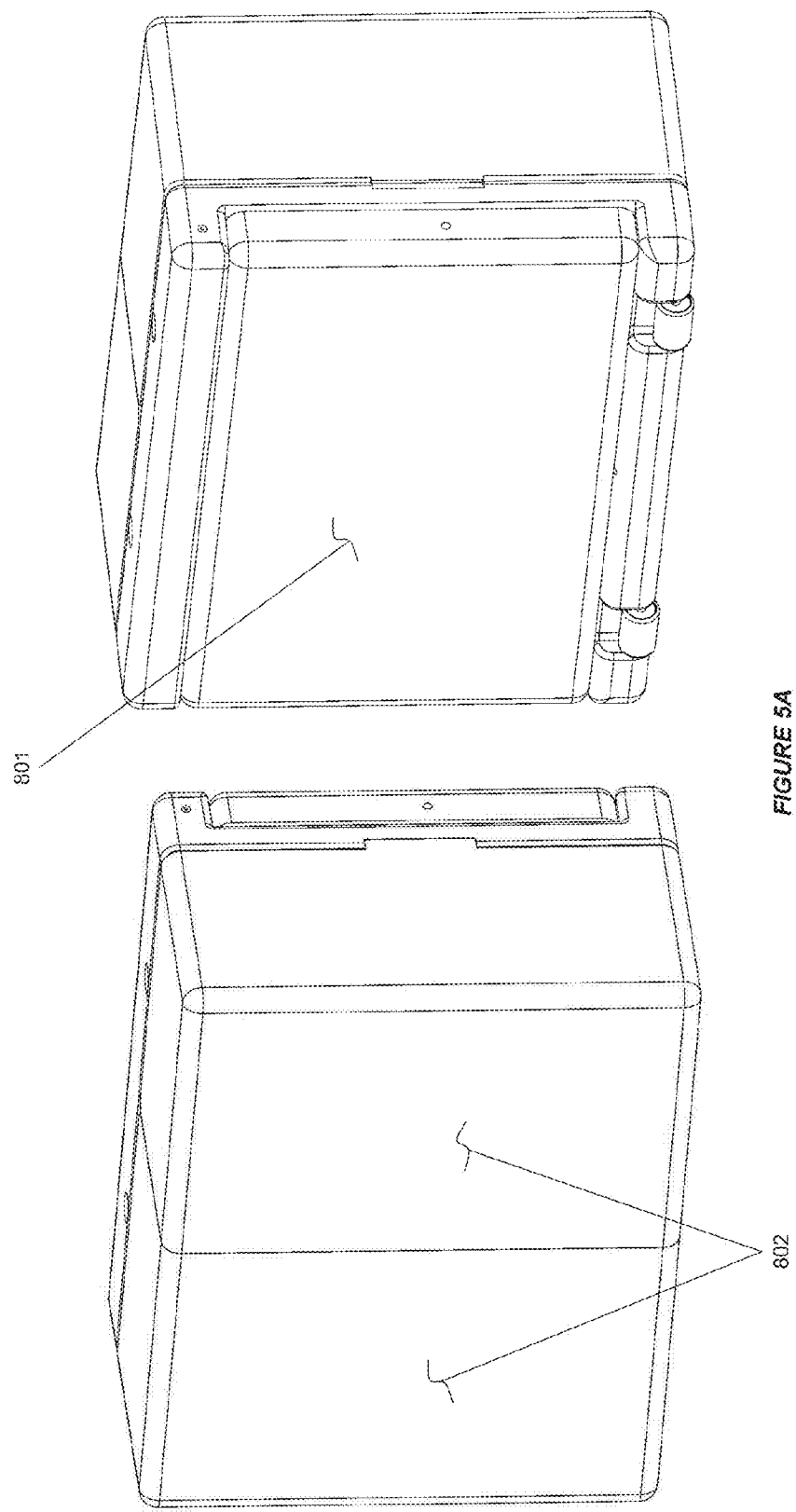

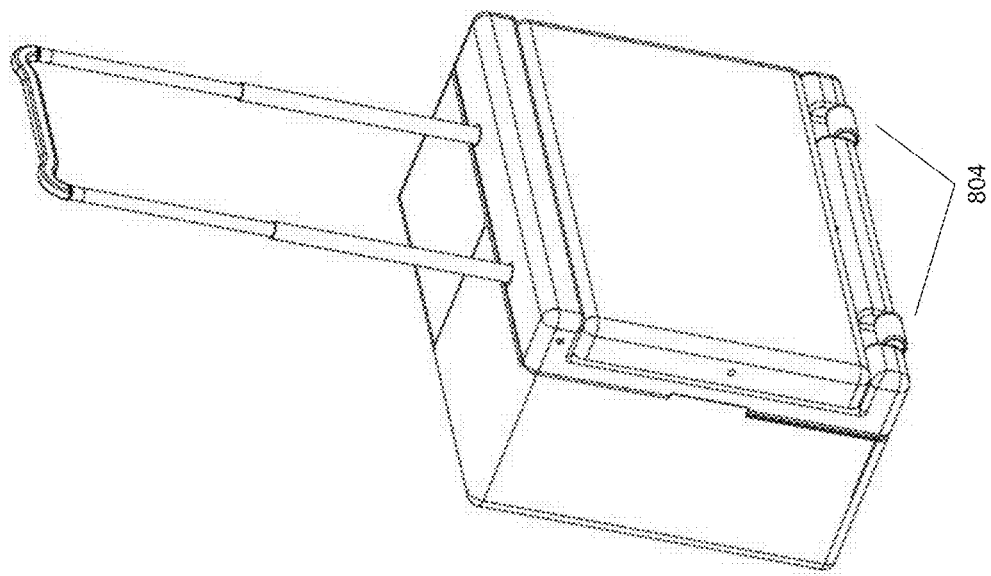
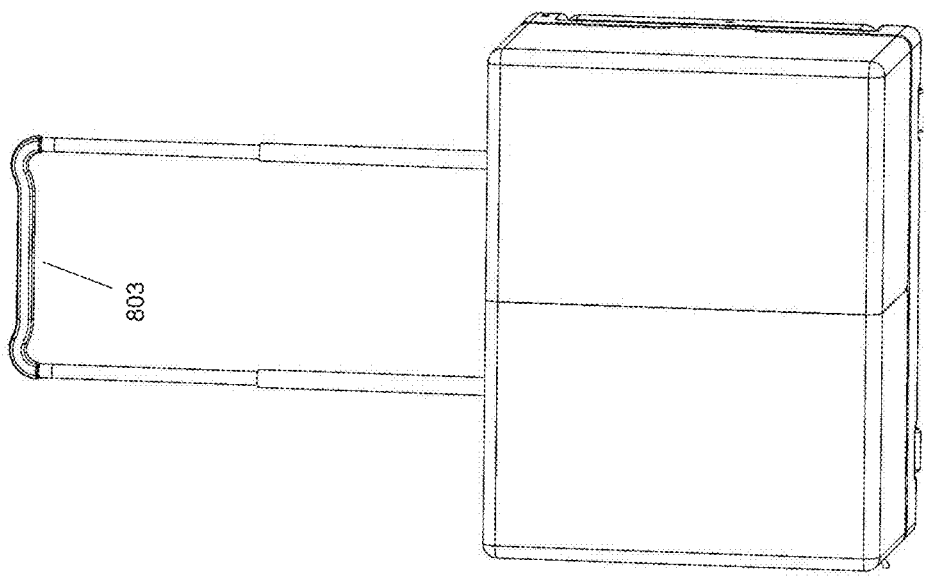
FIGURE 5B

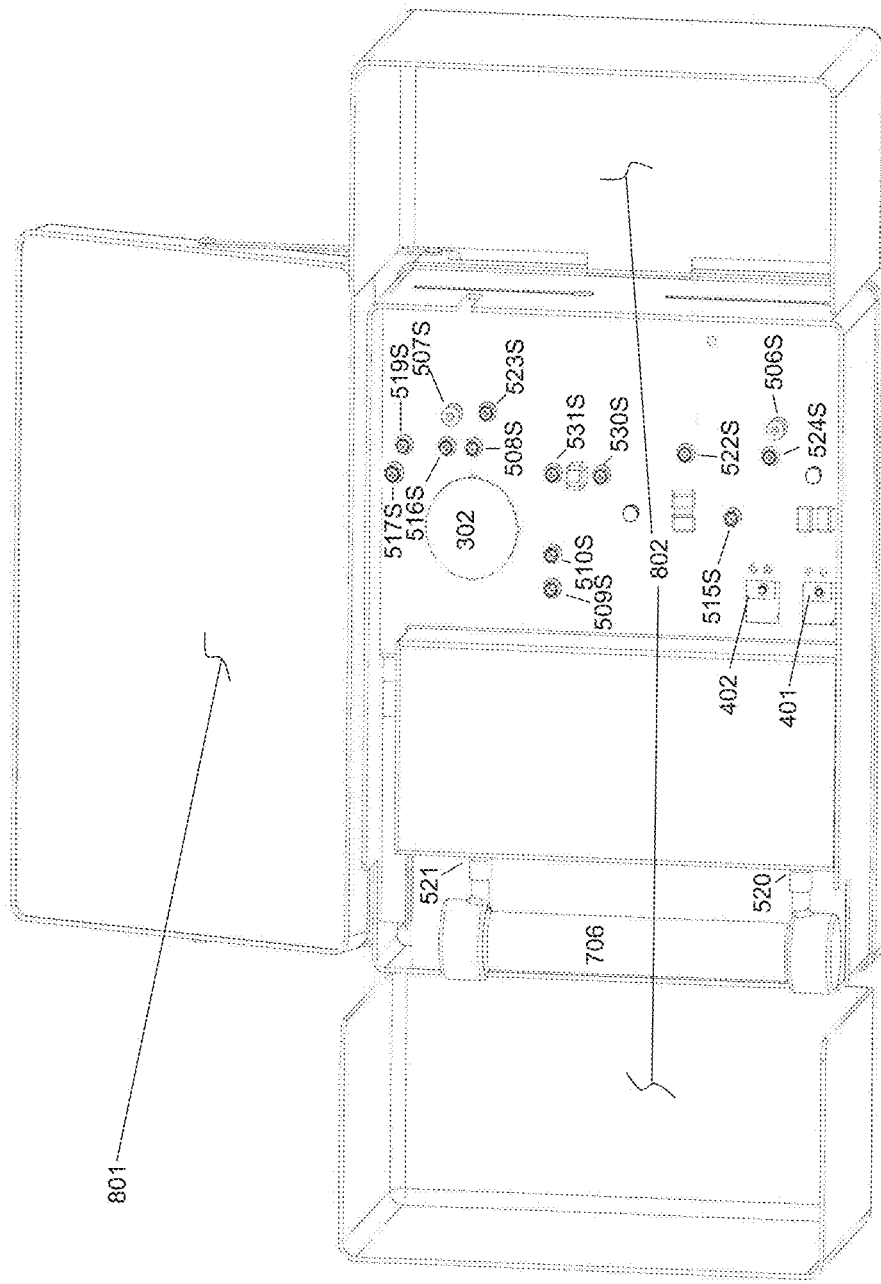

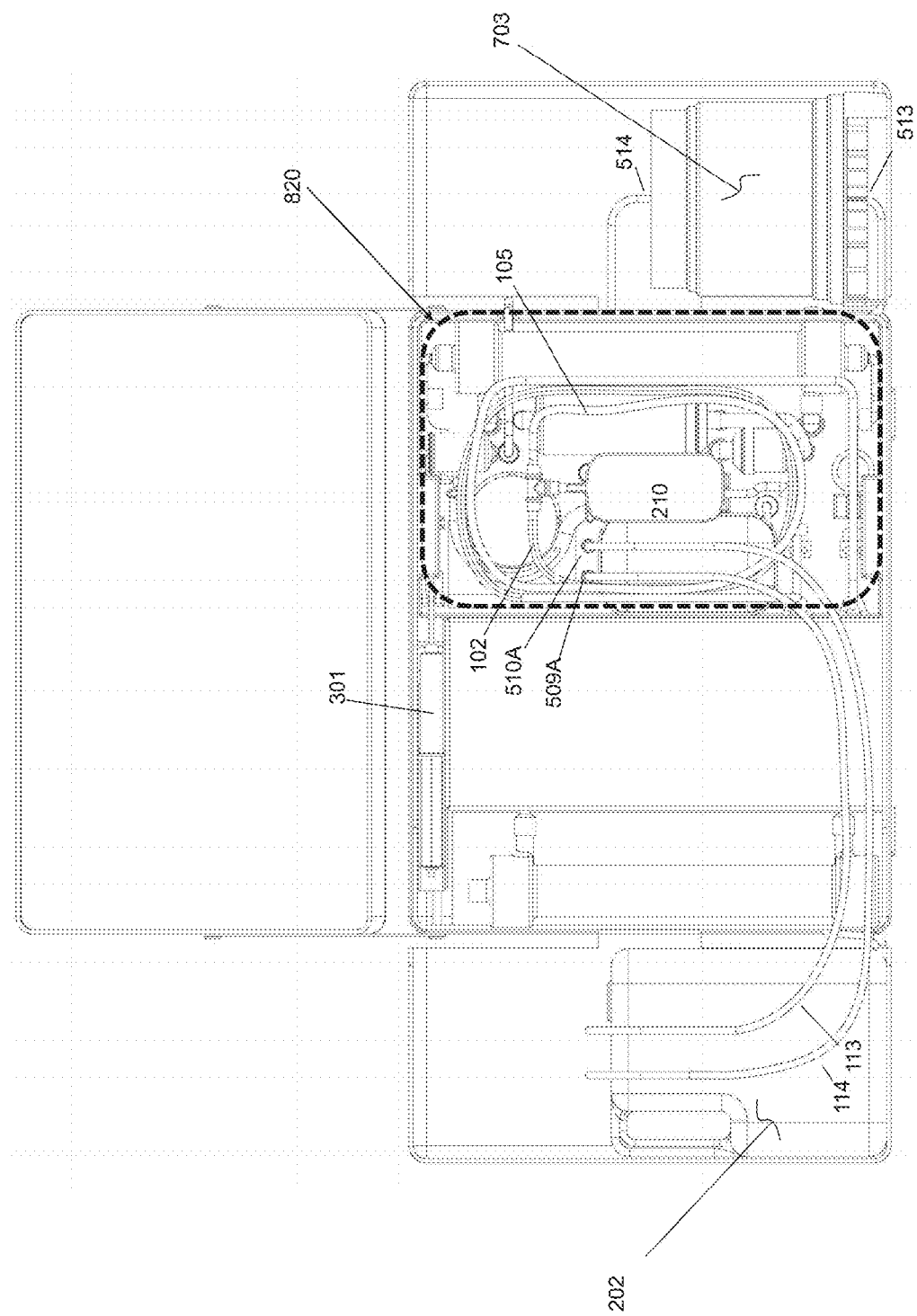

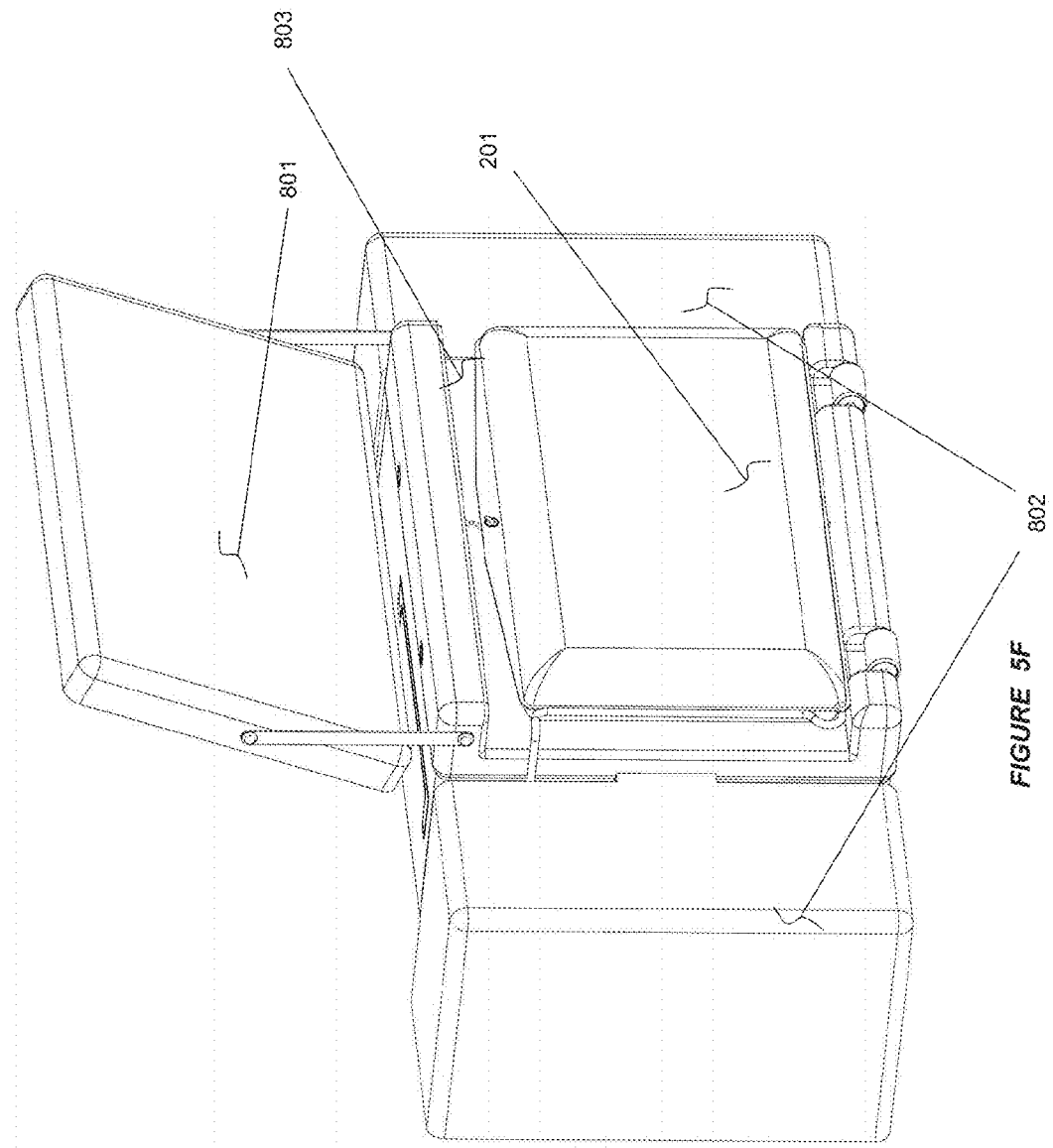

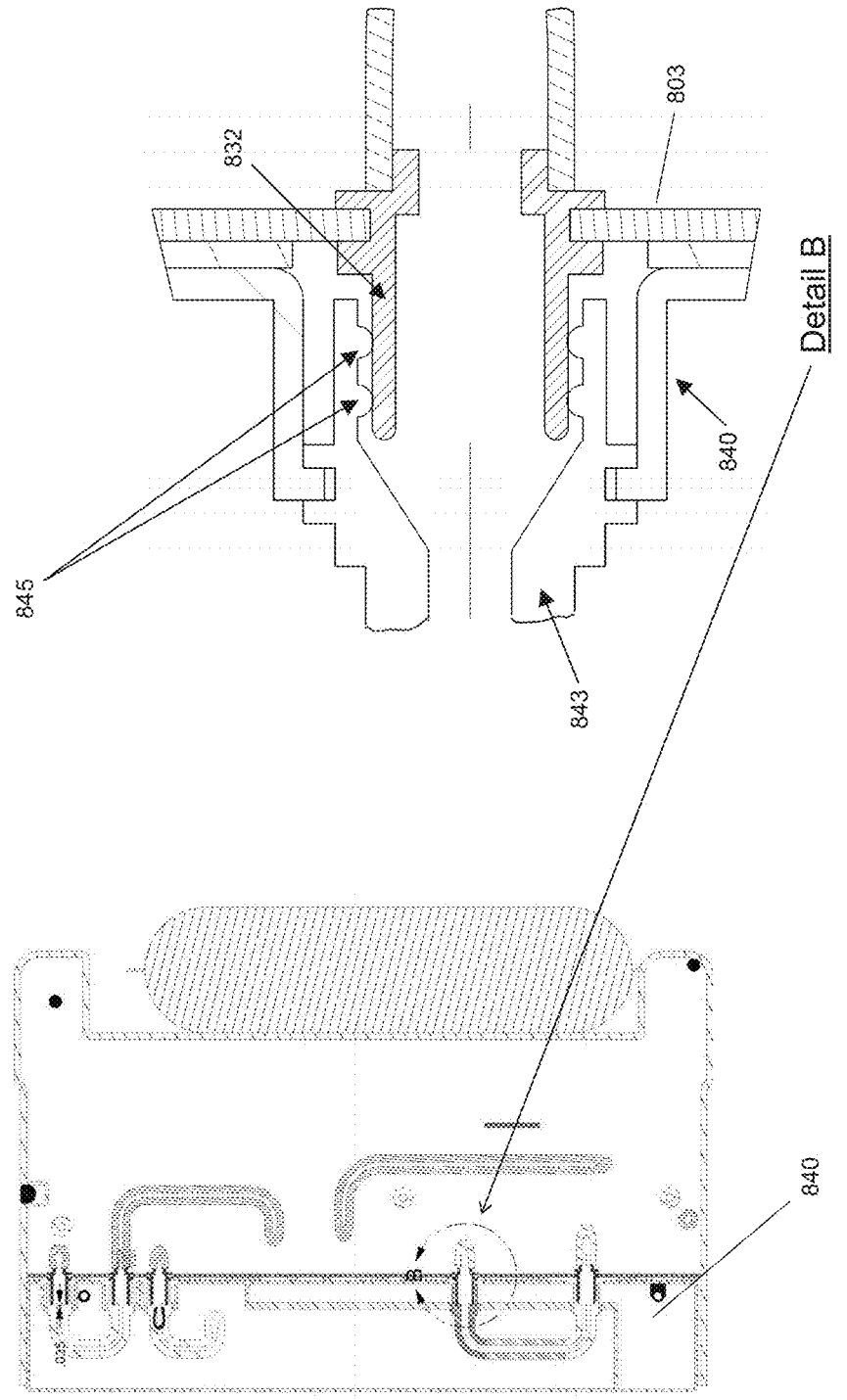

SODIUM AND BUFFER SOURCE CARTRIDGES FOR USE IN A MODULAR CONTROLLED COMPLIANT FLOW PATH

FIELD OF THE INVENTION

This disclosure relates to systems and methods for using a sodium chloride source and a buffer source such as sodium bicarbonate in a controlled compliant flow path to generate from water a physiologically compatible fluid having a suitable level of a sodium ion and/or a buffer for use in hemodialysis, hemodiafiltration and hemofiltration. The sodium chloride source and a buffer source can be configured as a dry sodium chloride and/or dry sodium bicarbonate cartridge or container wherein the cartridges or containers can infuse electrolytes in the treatment of pathological conditions such as End Stage Renal Disease (ESRD). The systems and methods have a modular design such that a dialyzer, control components, dialysate regeneration cartridge and fluid reservoirs are configured to be capable of operating free of a high volume of purified water source and drain utilities and infrastructure. A separate supply of packaged or prepared sterile saline is not required for priming, fluid bolus, or blood rinse back when using the present invention.

BACKGROUND

Chronic Kidney Disease (CKD), also known as chronic renal disease, may be a sudden or progressive loss in renal function. As the disease severity progresses, a patient with severe renal failure develops many symptoms that, if left untreated, eventually result in death. The most severe stage of CKD is End Stage Renal Disease (ESRD). ESRD, also referred to as kidney failure or renal failure, is the medical condition wherein a person's kidneys fail to sufficiently remove toxins, waste products, and excess fluid, and to maintain proper electrolyte levels.

Current treatments for CKD seek to manage comorbidities and, if possible, slow the progression of the disease. However, as the disease progresses, renal function decreases and eventually renal replacement therapy is employed to compensate for lost kidney function. Renal replacement therapy typically entails transplantation of a new kidney, or dialysis. Kidney dialysis is a medical procedure that is performed to aid or replace some of the kidney functions in severe renal failure. Hemodialysis, hemofiltration, hemodiafiltration, and peritoneal dialysis are all replacement therapies for patients who have lost most or all of their kidney function. Dialysis can remove many of the toxins and wastes that the natural kidney would remove. In addition, these therapies are used to balance the electrolyte or blood salt levels and to remove excess fluid that accumulates in patients with renal failure.

Hemodialysis treatment can be performed to remove waste products from the blood that are no longer being effectively removed by the kidneys, such as urea, creatinine and phosphates. Although the population of patients afflicted with CKD grows each year, there is no cure. The excess fluid accumulated in patients suffering from renal failure is generally removed by the ultrafiltration action of a dialysis procedure.

Hemodialysis procedures in developed countries are usually carried out three times a week in three to five hour sessions. In some geographies, hemodialysis is less available and conducted less frequently. Dialysis emulates kidney function by removing waste solutes, excess electrolytes and excess fluid from a patient's blood. During dialysis, the patient's blood that contains a high concentration of waste solutes is exposed to a semi-permeable membrane in contact with a solute-deficient dialysis solution (dialysate). Solute removal and electrolyte balancing is accomplished via diffusion across the membrane. Fluid removal is accomplished via pressure-driven convective transport through the membrane, commonly referred to as ultrafiltration. Once the blood is purified, it is then returned to the patient. Although effective at removing wastes from blood, dialysis treatments are administered intermittently and therefore do not emulate the continuous function of a natural kidney. Moreover, there are many inconveniences associated with dialysis, such as the necessity of traveling to a dialysis center and committing to time consuming treatments multiple times per week.

Although hemodialysis removes excess fluid, interdialytic intervals of a hemodialysis schedule create variations in the patient's waste removal, impurity removal, fluid removal and electrolyte balance. These variations result in patient complications and the high rates of patient morbidity and mortality. Since the mid-1990s a number of physicians have prescribed treatment regimens with increased dialysis frequency and treatment time to try to eliminate the problems associated with the thrice-weekly hemodialysis schedule. Two recent randomized controlled clinical studies have shown statistically significant benefits of a more frequent dialysis regimen. Culleton et al. (Culleton, B F et al. Effect of Frequent Nocturnal Hemodialysis vs. Conventional Hemodialysis on Left Ventricular Mass and Quality of Life. 2007 Journal of the American Medical Association 298 (11)) reported that when compared with conventional hemodialysis (trice weekly) daily nocturnal hemodialysis improved left ventricular mass (a surrogate for mortality), reduced the need for blood pressure medications and improved some measures of mineral metabolism. The FHN trial (The FHN Trial Group. In-Center Hemodialysis Six Times per Week versus Three Times per Week, New England Journal of Medicine, 2010) was a comparison of increased treatment frequency of 5.2 hemodialysis treatments a week compared with the traditional thrice-weekly regimen: "Frequent hemodialysis, as compared with conventional hemodialysis, was associated with favorable results with respect to the composite outcomes of death or change in left ventricular mass and death or change in a physical-health composite score." Based on this data it would be desirable to have a hemodialysis system that would allow kidney patients to dialyze from five to seven days a week, if not continuously.

Despite the clinical results from the Culleton and FHN research, few patients presently undergo a higher frequency of dialysis treatment. More frequent hemodialysis is only used on a small part of the patient population due to the burden and cost of more frequent therapies. Even the thrice weekly-regime is a significant burden to ESRD patients, and an increase in treatment frequency can often be difficult due to the deficiencies in known devices and the cost of the additional treatments. Most dialysis is performed in a dialysis center; hence, there is a need for the practical implementation of more frequent hemodialysis using a simple, wearable/portable, and safe technology that can be used by a patient at home.

Typical home-dialysis equipment employs an amount of dialysis fluid greater than 20 liters, up to 120 liters or more, that must be produced by a dedicated water purification system. The typical requirement for large amounts of purified water creates a barrier in that stationary, expensive, and often architecturally incompatible water purification supply and drain systems must be connected to the plumbing.

A different water-related barrier to treatment exists in some developing regions of the world, in that infrastructure to produce the large volumes of purified water may not exist within feasible traveling distance for persons suffering from ESRD. Thus, a dialysis therapy system that does not require large volumes of purified water could increase availability of life-saving hemodialysis therapy for those suffering from ESRD in such regions. In such regions, a system that can provide dialysis therapy from just a few liters of potable or bottled drinking water is of special value. In developing regions, or even in developed regions suffering from natural disaster, a model for delivering life-saving hemodialysis therapy can be mobile dialysis units that can travel to the location where therapy is needed and provide the needed therapy. Equipment that is compact, lightweight, and free of requirements for large volumes of purified water, and not requiring a high ratio of skilled technicians per patient to operate the equipment is the equipment of choice for this therapy delivery modality.

The large volume of dialysate fluid required for dialysis is in part attributable to the large quantity of solution necessary for the diffusion of waste products removed and the balancing of electrolytes within the dialysate from the blood of a dialysis patient. Regeneration of spent dialysate is one way to reduce the total volume of a dialysis system by eliminating the need for a large reserve of fresh dialysate. However, existing technologies for regenerating spent dialysate have been met with various limitations. For example, the Recirculating Dialysate System ("REDY system") may be subject to variations in pH and sodium concentrations that depart from physiological norms. Additionally, REDY systems have limited or no ability to remove sulfates, and may not be easily portable by the individual receiving therapy.

Development of dialysate recirculating techniques has resulted in systems that employ a variety of sorbent media, including activated carbon, urease, and zirconium-, aluminum-, and magnesium-based materials. Yet one of the problems associated with sorbent regeneration of spent dialysate is the buildup of sodium ions released as a byproduct of the adsorption process, thus necessitating a high degree of sodium concentration control which has yet to be achieved by currently available wearable or portable dialysis systems.

Some systems have attempted to address the volume and weight problems by allowing for external connections to a tap water source. However, the introduction of tap water into a dialysis system necessitates additional purification measures, thus adding to system complexity and size. As a result, such systems may not be useful for mobile or portable use.

Sorbent-based dialysate regeneration systems can be found in U.S. Pat. No. 3,669,878 Marantz et al., which describes sorbent removal of urea and ammonium ions from spent dialysate via urease, ammonium carbonate, and zirconium phosphate; U.S. Pat. No. 3,669,880 Marantz et al., which describes directing a controlled volume of dialysate through zirconium phosphate, activated carbon, and hydrated zirconium oxide columns; U.S. Pat. No. 3,850,835 Marantz et al., which describes production of a zirconium hydrous oxide ion exchange media; and U.S. Pat. No. 3,989,622 Marantz et al., which describes adsorption of urease on aluminum oxide and magnesium silicate media to convert liquid urea to ammonium carbonate.

U.S. Pat. No. 4,581,141 Ash describes removal of uremic substances from dialysate via a calcium-based cation exchanger, urease, and aliphatic carboxylic acid resin. U.S. Pat. No. 4,826,663 Alberti et al. describes a method of preparing a zirconium phosphate ion exchanger. U.S. Pat. No. 6,627,164 Wong describes production of sodium zirconium carbonate for ion exchange in renal dialysis, and U.S. Pat. No. 7,566,432 Wong describes production of zirconium phosphate particles for ion exchange in regenerative dialysis. U.S. Pat. No. 6,818,196 Wong, U.S. Pat. No. 7,736,507 Wong, U.S. Application Publication 2002/0112609 Wong, U.S. Application Publication 2010/0078387 Wong, and U.S. Application Publication 2010/00784330 Wong, describe cartridges for purification of dialysis solutions using sodium zirconium carbonate.

U.S. Pat. No. 6,878,283 Thompson, U.S. Pat. No. 7,776,210 Rosenbaum et al., U.S. Application Publication 2010/0326911 Rosenbaum et al., U.S. Application Publication 2010/0078381 Merchant, U.S. Application Publication 2009/0127193 Updyke et al. and U.S. Application Publication 2011/0017665 Updyke et al. describe filter cartridges having a plurality of types of filter media including zirconium compounds, urease, and alumina for dialysis systems. WO 2009/157877 A1 describes a urease material having urease immobilized on a substrate intermixed with a cation exchange material or zirconium phosphate material to improve workability for the reduction of clogging and to improve absorption of ammonium ions generated by the urease.

Management of impurities in regenerated dialysate can be found in U.S. Pat. No. 4,460,555 Thompson and U.S. Pat. No. 4,650,587 Polak et al., which describes magnesium phosphate media for removal of ammonia from aqueous solutions, U.S. Application Publication 2009/0282980 Gura et al.; "A Study on the Temperature Variation of Rise Velocity for Large Clean Bubbles," Leifer et al., J. Atmospheric & Oceanic Tech., Vol. 17, pp 1392-1402; "Terminal Velocity of a Bubble Rise in a Liquid Column," Talaia, World Acad. of Sci., Engineering & Tech., Vol. 28, pp. 264-68; U.S. patent application Ser. No. 12/937,928 to Beck; U.S. Pat. No. 5,468,388 to Goddard et al.; U.S. patent application Ser. No. 12/182,489 to Kirsch; U.S. patent application Ser. No. 12/355,128 to Gura et al.; U.S. Pat. No. 4,371,385 to Johnson; U.S. Pat. No. 4,381,999 to Boucher et al.; U.S. patent application Ser. No. 12/516,786 to Wallenborg et al.; U.S. Pat. No. 4,828,693 to Lindsay et al.; U.S. Pat. No. 5,762,782 to Kenley et al.; U.S. Pat. No. 7,981,082 to Wang et al.; and U.S. patent application Ser. No. 13/100,847 to Palmer.

There is a need for systems and/or methods that can simplify and automate these tasks for those individuals suffering from ESRD who are unable to access a dialysis centers, or who prefer not to. There is also a further need for expansion of hemodialysis therapy to individuals, or those living in developing regions where there is limited space available for the equipment at the home including those individuals suffering from ESRD who live in a single room shared by multiple individuals.

In particular, it is a need to provide a system that is capable of modifying water into any one of a solution for priming an extracorporeal flow path, rinsing or flushing a dialyzer and blood flow conduits, a physiologically compatible solution for contacting blood, a physiologically compatible solution for bolus infusion to a subject, and a solution for blood rinse back to a subject.

SUMMARY OF THE INVENTION

The present invention describes system and methods for generating a physiologically compatible fluid that has a conditioning flow path having at least a salination valve or salination pump, and at least one container having at least one solute in excess of the solubility of that solute wherein at least one of the solutes is a buffer source or sodium chloride; said conditioning flow path in fluid communication with a controlled compliant flow path wherein the conditioning flow path has a means for selectively metering fluid into and out of the controlled compliant flow path.

In any embodiment, the system can have a controlled compliant flow path that modifies water into any one of a solution for priming an extracorporeal flow path, rinsing or flushing a dialyzer and blood flow conduits, a physiologically compatible solution for contacting blood, a physiologically compatible solution for bolus infusion to a subject, and a solution for blood rinse back to a subject.

In any embodiment, the system can have a means for selectively metering in and metering out fluid from a controlled compliant flow path that generates a physiologically compatible level of a sodium ion and/or a buffer from the at least one container in the conditioning flow path. In any embodiment, the system can have a sodium chloride container and a buffer source container wherein the conduits and containers of the conditioning flow path have a non-compliant volume.

In any embodiment, the system can have a sodium chloride and a buffer source that are dry compositions wherein the dry compositions are hydrated by circulating a fluid through the conditioning flow path.

In any embodiment, the system can have a conditioning flow path inlet and a conditioning flow path outlet that are in fluid communication with any point on the controlled compliant flow path.

In any embodiment, the system can have a means for selectively metering fluid into and out of the controlled compliant flow path that can be a fluid balance control pump in fluid communication with the controlled compliant flow path and a fluid reservoir.

In any embodiment, the system can have a means for selectively metering fluid into and out of the controlled compliant flow path wherein the means can be any one of a control pump, a water pump, a salination pump, an acid concentrate pump, a replacement fluid pump, and combinations thereof.

In any embodiment, the system can have a controlled compliant flow path that has at least one pump or valve in fluid communication with both a conduit of the controlled compliant flow path and a container; and a pump in fluid communication with a conduit of the controlled compliant flow path and a water source.

In any embodiment, the system can have at least one pump or valve in fluid communication with a conduit of the controlled compliant flow path and at least a buffer source or a sodium source, a pump in fluid communication with a conduit of the controlled compliant flow path and a water source.

In any embodiment, the system can have fluid passing through a sodium chloride container to increase the sodium chloride concentration of the fluid and fluid passing through the buffer source container to increase the buffer concentration of the fluid.

In any embodiment, the system can have a sodium chloride container, the buffer source container and the salination valve being configured into a consumables cartridge.

In any embodiment, the system can have a sodium chloride and the buffer source that are contained in separate compartments of a common container or cartridge.

In any embodiment, the system can have a sodium compartment and a buffer source compartment sharing a common fluid inlet port or a common fluid outlet port. In any embodiment, the system can have a container that is disposable. In any embodiment, the system can have a container that is re-usable and refilled or replenished with sodium chloride or a buffer source.

In any embodiment, the system can also have a common reservoir and a control pump in fluid communication with the conditioning flow path wherein the common reservoir contains any one of a dialysate, a filtrate, a volume of a physiologically compatible priming solution, a volume of a physiologically compatible solution to provide a bolus of fluid to a subject receiving treatment, a volume of physiologically compatible solution to provide solution for return of blood from an extracorporeal flow path to a subject receiving treatment, a volume of solution returned to the common reservoir from an extracorporeal flow path when blood from a subject is introduced to the extracorporeal flow path, fluids drained from the system, and combinations thereof.

The method of the invention provides for generating a physiologically compatible fluid and preparing the physiologically compatible fluid from water using the any one of the systems described herein. The controlled compliant flow path can modify water into any one of a solution for priming a blood system, a solution for flushing or rinsing a dialyzer or an extracorporeal flow path, a physiologically compatible solution for contacting blood, a physiologically compatible solution for bolus infusion to a subject, and a solution for blood rinse back to a subject.

In any embodiment, the method can have a first container that is a sodium chloride cartridge and a second container that is a buffer source cartridge, and can generate a predetermined level of sodium ion and buffer from the sodium chloride cartridge and the buffer source cartridge.

In any embodiment, the method can generate a physiologically compatible priming solution and store the physiologically compatible priming solution in a therapy solution reservoir using a control pump on the controlled compliant flow path.

In any embodiment, the method can have the step of generating a physiologically compatible bolus infusion solution and storing the physiologically compatible bolus infusion solution in a therapy solution reservoir using a control pump on the controlled compliant flow path.

In any embodiment, the method can have the step of generating a physiologically compatible rinse-back solution; and storing the physiologically compatible rinse-back solution in a therapy solution reservoir using a control pump on the controlled compliant flow path.

In any embodiment, the method can have the step of providing water to a system having a conditioning flow path in fluid communication with a controlled compliant flow path wherein the controlled compliant flow path is in fluid communication with an extracorporeal flow path across a semi-permeable membrane; configuring the system to bypass the extracorporeal flow path, the system having a bypass conduit flow path for conveying fluid through a first segment of the controlled compliant flow path without contacting the semipermeable membrane; removing dissolved gas from the water; conveying the water through the conditioning flow path; reconstituting an electrolyte source to generate a physiologically compatible fluid, and conveying the fluid through the first segment of the controlled compliant flow path.

In any embodiment, the method can have a conditioning flow path that has a buffer source cartridge.

In any embodiment, the method can have a buffer source cartridge that is an interchangeable bicarbonate cartridge and a sodium source cartridge that is an interchangeable sodium chloride cartridge wherein the conditioning flow path has a sodium conduit flow path with a sodium source configured in parallel with a buffer source conduit flow path with a buffer source.

SUMMARY OF THE DRAWINGS

FIG. 4A shows the patient blood access connector ends of the extracorporeal flow path joined at a tee connection with fluid overflow reservoir for storage of excess priming fluid in accordance with certain embodiments.

FIG. 4C shows the patient blood access connector ends of the extracorporeal flow path connected to separate inlet and outlet ports of an overflow reservoir for priming of an extracorporeal flow path in accordance with certain embodiments.

FIG. 5A shows a hemodialysis device in configuration for storage or transport stowage in accordance with certain embodiments.

FIG. 5B shows hemodialysis device in transport configuration in accordance with certain embodiments.

FIG. 5C shows a user interface and shelf doors deployed on the main body of a hemodialysis device base module in "set-up ready" configuration with fluid connection ports exposed in accordance with certain embodiments.

FIG. 5E shows an example of a therapy disposables and consumables cassette, sorbent cartridge, and connected water supply reservoir in accordance with certain embodiments.

FIG. 5F shows an example of a therapy solution reservoir (control reservoir) deployed on a hemodialysis device in accordance with certain embodiments.

FIG. 7B shows a mating fluid connection port configuration for fluid communication between a cleaning and disinfection manifold and a fluid pathway of a base module.

Throughout the figures and the specification, components with the same numbers in the FIGS. refer to the same components.

DETAILED DESCRIPTION OF THE INVENTION

Definitions

Figure 1:
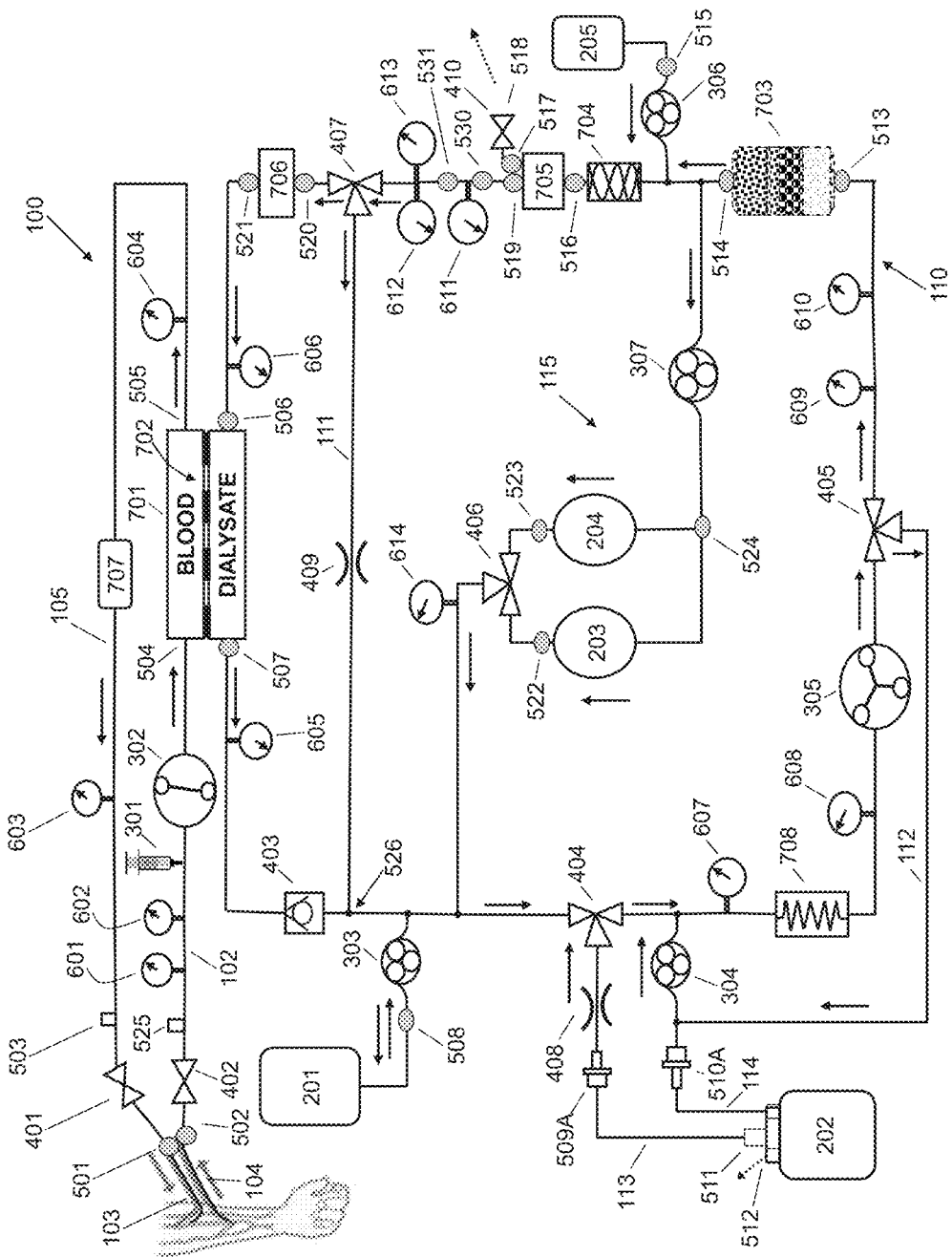
FIG. 1 shows a hemodialysis device having a controlled compliant flow path and jumpered ports in accordance with certain embodiments.

Unless defined otherwise, all technical and scientific terms used herein generally have the same meaning as commonly understood by one of ordinary skill in the relevant art. The definitions provided herein should not be rigidly construed without taking into account the context and other ascribed meanings provided, or by their use, in other parts of the specification, claims, and drawings.

The articles "a" and "an" are used herein to refer to one or to more than one (i.e., to at least one) of the grammatical object of the article. By way of example, "an element" means one element or more than one element.

An "acid" can be either an Arrhenius acid, a Brønsted-Lowry acid, or a Lewis acid. The Arrhenius acids are substances or fluids which increase the concentration of hydronium ions (H3O+) in solution. The Brønsted-Lowry acid is a substance which can act as a proton donor. Lewis acids are electron-pair acceptors The term "cation infusate pump" historically known as an "acid concentrate pump" in dialysis systems refers to a pump that serves the function to move or control the flow of a fluid to and/or from a reservoir having a substance that contains at least one cation species, such as calcium, magnesium and potassium ions. In the present invention, the historically used term of "acid concentrate pump" is used.

The term "activated carbon" refers to a porous carbon material having a surface area greater than 500 m² per gram. Activated carbon can be capable of absorbing several species including heavy metals such as lead, mercury, arsenic, cadmium, chromium and thallium among others, oxidants such as chlorine and chloramines, fluoride ions, and waste species such as phosphate and certain nitrogen-containing waste species such as creatinine and uric acid.

The terms "administering," "administer," "delivering," and "deliver," can be used in context to indicate the provision of water; aqueous solutions such as saline and dialysate that may contain salts acids, bases, and sugars; anticoagulant; or therapeutics such as erythropoietin and vitamins to a dialysate, dialysis circuit, or extracorporeal flow path where such water, or agent will enter the blood of the patient by diffusion, transversal of a diffusion membrane or other means.

The term "air trap" refers to a structure for separating a gas from a mixture of a gas and a liquid or any other separation means known in the art. An air trap can include a hydrophobic membrane for allowing gases to pass and for preventing the passage of water.

The term "albumin sieving coefficient" can be used to describe the amount of albumin that will cross a membrane.

The terms "ammonia sensing module" and "ammonia detector" refer to a unit that performs all or part of the function to detect a predetermined level of, or measure a concentration of, ammonia and/or ammonium ions in a fluid.

The term "anticoagulant" is a substance that prevents or delays the clotting of blood, such as heparin, Fragmin®, and sodium citrate.

The term "atmospheric pressure" refers to the local pressure of air in the environment in proximity to the system at the time that the system is operating.

A "base" can be either a substance that can accept hydrogen cations (protons) or more generally, donate a pair of valence electrons. A soluble base is referred to as an alkali if it contains and releases hydroxide ions (OH—) quantitatively. The Brønsted-Lowry theory defines bases as proton (hydrogen ion) acceptors, while the more general Lewis theory defines bases as electron pair donors, allowing other Lewis acids than protons to be included. [1] The Arrhenius bases act as hydroxide anions, which is strictly applicable only to alkali.

The term "base module" refers to a basic unit of an apparatus for hemodialysis, hemodiafiltration, or hemofiltration that incorporates one or more fluid pathways. Exemplary, non-limiting components that can be included in the base module include conduits, valves, pumps, fluid connection ports, sensing devices, a controller and a user interface. The base module can be configured to interface with reusable or disposable modules of the apparatus for hemodialysis, hemodiafiltration, or hemofiltration to form at least one complete fluid circuit, such as a dialysis, cleaning, disinfection, priming or blood rinse back circuit.

The term "bicarbonate buffer component" refers to any composition contain bicarbonate (HCO3—) ion or a conjugate acid of bicarbonate ion in any amount, proportion or pH of the composition. The bicarbonate buffering system is an important buffer system in the acid-base homeostasis of living things, including humans. As a buffer, it tends to maintain a relatively constant plasma pH and counteract any force that would alter it. In this system, carbon dioxide (CO2) combines with water to form carbonic acid (H2CO3), which in turn rapidly dissociates to form hydrogen ions and bicarbonate (HCO3—) as shown in the reactions below. The carbon dioxide-carbonic acid equilibrium is catalyzed by the enzyme carbonic anhydrase; the carbonic acid-bicarbonate equilibrium is simple proton dissociation/association and needs no catalyst.

$$CO_2 + H_2O \leftrightarrows H_2CO_3 \leftrightarrows HCO_3^- + H^+$$

Any disturbance of the system will be compensated by a shift in the chemical equilibrium according to Le Chatelier's principle. For example, if one attempted to acidify the blood by dumping in an excess of hydrogen ions (acidemia), some of those hydrogen ions will associate with bicarbonate, forming carbonic acid, resulting in a smaller net increase of acidity than otherwise.

The term "bicarbonate cartridge" refers to a container that can be a stand-alone container or alternatively can be integrally formed with an apparatus for hemodialysis, hemodiafiltration, or hemofiltration. The bicarbonate cartridge can store a source of buffering material, such as sodium bicarbonate, and can be configured to interface with at least one other functional module found in systems for hemodialysis, hemodiafiltration, or hemofiltration. For example, the bicarbonate cartridge can contain at least one fluid pathway and include components such as conduits, valves, filters or fluid connection ports. The bicarbonate cartridge can be disposable or be consumable wherein the cartridge is recharged upon depletion. Specifically, the term "bicarbonate consumables container" refers to an object or apparatus having or holding a material in solid and/or solution form that is a source of bicarbonate, such as sodium bicarbonate, that is depleted during operation of the system. The object or apparatus may be single use, or may be replenished and used multiple times, for example, by refilling the object to replace the consumed material.

The term "bidirectional pump" refers to a device configured to perform work on a fluid to cause the fluid to flow alternatively in either of two opposing directions.

A "biocompatible material" is a material that has the ability to interface with living biological tissues with an acceptable host response in any of specific medical systems, methods of treatment or delivery contemplated herein. The biocompatible material can consist of synthetic, natural or modified natural polymers intended to contact or interact with the biological systems during application of any of the inventions contained herein.

The term "blood access connection" refers to a junction or aperture through which the blood of a subject is conveyed to or from an extracorporeal circuit. Commonly, the blood access connection is made between a terminal end of a conduit of an extracorporeal circuit and the terminal end of a catheter or fistula needle that is distal to the subject receiving therapy. A subject may have more than one blood access connection when receiving therapy. In the case of two blood access connections they can be referred to as an arterial blood access connection and a venous blood access connection.

The term "blood rinse back" refers to returning the blood from a dialyzer and/or extracorporeal circuit to a subject, normally at conclusion of a therapy session and prior to disconnecting or removing the subject's blood access connection or connections. The procedure can include conveying a physiologically compatible solution through the extracorporeal circuit to push or flush the blood from the extracorporeal circuit to the subject via the subject's blood access connection or connections.

The term "bolus" refers to an increase (or at times a decrease) of limited duration in an amount or concentration of one or more solutes, for example sodium, glucose and potassium, or a solvent, for example water, such that the concentration of a solution is changed. The term "bolus" includes delivery of solute and/or solvent to the dialysate fluid path such that it is delivered to the blood of a subject via diffusion and/or convection across a dialysis membrane such that the amount or concentration in the subject is increased or decreased. A "bolus" may also be delivered directly to the extracorporeal flow path or the blood of a subject without first passing through the dialysis membrane.

The term "bottled water" refers to water that may be filtered or purified and has been packaged in a container. Bottled water can include water that has been packaged and provided to a consumer as drinking water.

The terms "bubble detector", "bubble sensor", "gas detector" and "air detector" refer to a device that can detect the presence of a void, void space, or gas bubble in a liquid.

The term "buffer source" refers to a stored material, such as bicarbonate, acetate or lactate that provides buffering.

The term "buffer conduit flow path" refers to a fluid flow path in fluid communication with a stored source of a buffering material, such as bicarbonate.

The term "buffer source" refers to a stored material, such as bicarbonate, acetate or lactate that provides buffering.

The terms "buffer source container" and "buffer source cartridge" refer to objects that have or hold one or more materials, in solid and/or solution form, that are a source of buffering, for example a bicarbonate, a lactate, or acetate; and the object further having at least one port or opening to allow at least a portion of the buffering material to be released from the object during operation of the system.

The terms "bypass circuit," "bypass conduit," "bypass flow path," "bypass conduit flow path" and "bypass" refer to a component or collection of components configured or operable to create an alternate fluid pathway to convey a fluid around one or more other components of a fluid circuit such that at least a portion of the fluid does not contact or pass through the one or more other components. At times the term "shunt" may be used interchangeable with the term "bypass" When any of the above "bypass" terms listed in this paragraph are used in context as being part of a controlled compliant system, then the relevant referenced "bypass" has the proper characteristics as to operate within a controlled compliant system as defined herein The term "cartridge" refers to a compartment or collection of compartments that contains at least one material used for operation of the system of the present invention.

The term "cassette" refers to a grouping of components that are arranged together for attachment to, or use with the device, apparatus, or system. One or more components in a cassette can be any combination of single use, disposable, consumable, replaceable, or durable items or materials.

The term "cation infusate source" refers to a source from which cations can be obtained. Examples of cations include, but are not limited to, calcium, magnesium and potassium. The source can be a solution containing cations or a dry composition that is hydrated by the system. The cation infusate source is not limited to cations and may optionally include other substances to be infused into a dialysate or replacement fluid, non-limiting examples can be glucose, dextrose, acetic acid and citric acid.

The term "cation concentrate reservoir" refers to an object having or holding a substance that is comprised of at least one cation, for example calcium, magnesium, or potassium ions.

"Chronic kidney disease" (CKD) is a condition characterized by the slow loss of kidney function over time. The most common causes of CKD are high blood pressure, diabetes, heart disease, and diseases that cause inflammation in the kidneys. CKD can also be caused by infections or urinary blockages. If CKD progresses, it can lead to end-stage renal disease (ESRD), where the kidneys fail to function at a sufficient level.

The term "citric acid" refers to an organic acid having the chemical formula $C_6H_8O_7$, and may include anhydrous and hydrous forms of the molecule, and aqueous solutions containing the molecule.

The term "cleaning and/or disinfection concentrate" refers to a dry substance or solutions containing at least one material for use in cleaning and/or disinfection of an apparatus.

The term "cleaning and/or disinfection solution" refers to a fluid that is used for the purpose of removing, destroying or impairing at least a portion of at least one contaminant. The contaminant may be organic, inorganic or an organism. The fluid may accomplish the purpose by transmission of thermal energy, by chemical means, flow friction or any combination thereof.

The terms "cleaning manifold" and "cleaning and disinfection manifold" refer to an apparatus that has fluid connection ports and one or more fluid pathways, or fluid port jumpers, that, when connected to jumpered ports of a base module, create a one or more pathways for fluid to be conveyed between the jumpered ports of the base module. A cleaning manifold may be further comprised of additional elements, for example valves and reservoirs.

The term "common container," "common cartridge," or "common reservoir," and the like refer to an object or apparatus that can hold more than one material; however, the time of holding more than one material may or may not necessarily be at the same time. The material(s) may be in solid and/or solution forms and may be held in separate compartments within the object or apparatus.

The term "common fluid inlet port" refers to an opening or aperture through which all fluid first passes to enter an object, apparatus or assembly.

The term "common fluid outlet port" refers to an opening or aperture through which all fluid passes to exit an object, apparatus or assembly.

The terms "communicate" and "communication" include, but are not limited to, the connection of system electrical elements, either directly or remotely, for data transmission among and between said elements. The terms also include, but are not limited, to the connection of system fluid elements enabling fluid interface among and between said elements.

The terms "component" and "components" refer to a part or element of a larger set or system. As used herein, a component may be an individual element, or it may itself be a grouping of components that are configured as a set, for example, as a cassette or a cleaning and/or disinfection manifold.

The term "comprising" includes, but is not limited to, whatever follows the word "comprising." Thus, use of the term indicates that the listed elements are required or mandatory but that other elements are optional and may or may not be present.

The term "concentrate pump" refers to a device that can perform work on a fluid solution to cause the fluid to flow and can actively control the transfer of fluid volume such as an infusate or an acid concentrate into a circuit.

The terms "conditioning conduit flow path" or "conditioning flow path" refer to a fluid pathway, circuit or flow loop that incorporates a source of a conditioning material, for example a sodium salt or bicarbonate.

The term "conditioning flow path inlet" refers to a location on a conditioning flow path where fluid enters the conditioning flow path.

The term "conditioning flow path outlet" refers to a location on a conditioning flow path where fluid exits the conditioning flow path.

The term "conductive species" refers to a material's ability to conduct an electric current. Electrolytes are an example of a conductive species in dialysate fluids, such as, but not limited to the presence sodium, potassium, magnesium, phosphate, and chloride ions. A fluid's ability to conduct an electrical current is due in large part to the ions present in the solution.

The terms "conductivity meter," "conductivity sensor," "conductivity detector" and the like refer to devices for measuring the electrical conductance of a solution and/or the ion, such as a sodium ion, concentration of a solution. In specific examples, the conductivity sensor, meter, or detector can be directed to a specific ion such as sodium and be referred to as a "sodium electrode," "sodium sensor," "sodium detector," or "sodium meter."

The term "conduit," "circuit" or "flow path" refers to a vessel or passageway having a void volume through which a fluid can travel or move. A conduit can have a dimension parallel to the direction of travel of the fluid that is significantly longer than a dimension orthogonal to the direction of travel of the fluid The term "connectable" refers to being able to be joined together for purposes including but not limited to maintaining a position, allowing a flow of fluid, performing a measurement, transmitting power, and transmitting electrical signals. The term "connectable" can refer to being able to be joined together temporarily or permanently.

The term "consisting of" includes and is limited to whatever follows the phrase "consisting of." Thus, the phrase indicates that the limited elements are required or mandatory and that no other elements may be present.

The term "consisting essentially of" includes whatever follows the term "consisting essentially of" and additional elements, structures, acts or features that do not affect the basic operation of the apparatus, structure or method described.

The term "consumables" refers to components that are dissipated, wasted, spent or used up during the performance of any function in the present invention. Examples include a quantity of sodium, bicarbonate, electrolytes, infusates, sorbents, cleaning and disinfecting ingredients, anticoagulants, and components for one or more concentrate solutions.

The terms "consumables cartridge" and "consumables container" refer to an object or apparatus having or holding one or more materials that are depleted during operation of the system. The one or more materials may be in solid and/or solution form and can be in separate compartments of the object or apparatus. The object or apparatus may be single use, or may be replenished and used multiple times, for example, by refilling the object to replace the consumed material.

The term "contact" "contacted" or "contacting" refers to (1) a coming together or touching of objects, fluids, or surfaces; (2) the state or condition of touching or of immediate proximity; (3) connection or interaction. For example, in reference to a "dialysate contacting a sorbent material" refers to dialysate that has come together, has touched, or is in immediate proximity to connect or interact with any material or material layer of a sorbent container, system or cartridge.

The term "container" as used herein is a receptacle that may be flexible or inflexible for holding any fluid or solid, such as for example a spent dialysate fluid, or a sodium chloride or sodium bicarbonate solution or solid, or the like.

The term "contaminant" refers to an undesirable or unwanted substance or organism that may cause impairment of the health of a subject receiving a treatment or of the operation of the system.

The term "control pump," such as for example an "ultrafiltrate pump," refers to a pump that is operable to pump fluid bi-directionally to actively control the transfer of fluid volume into or out of a compartment or circuit.

The terms "control reservoir," "ultrafiltrate reservoir," "solution reservoir," "therapy solution reservoir," or "waste reservoir" can refer to a vessel or container, optionally accessible by a control pump that contains a variable amount of fluid, including fluid that can be referred to as an ultrafiltrate. These reservoirs can function as a common reservoir to store fluid volume from multiple sources in a system. Other fluids that can be contained by these reservoirs include, for example, water, priming fluids, waste fluids, dialysate, including spent dialysate, and mixtures thereof. In certain embodiments, the reservoirs can be substantially inflexible, or non-flexible. In other embodiments, the reservoirs can be flexible containers such as a polymer bag.

The term "control signals" refers to energy that is provided from one element of a system to another element of a system to convey information from one element to another or to cause an action. For example, a control signal can energize a valve actuator to cause a valve to open or close. In another example a switch on a valve can convey the open or close state of a valve to a controller.

A "control system" consists of combinations of components that act together to maintain a system to a desired set of performance specifications. The control system can use processors, memory and computer components configured to interoperate to maintain the desired performance specifications. It can also include fluid control components and solute control components as known within the art to maintain the performance specifications The term "control valve" or "valve" refers to a device that can be operated to regulate the flow of fluid through a conduit or flow path by selectively permitting fluid flow, preventing fluid flow, modifying the rate of fluid flow, or selectively guiding a fluid flow to pass from one conduit or flow path to one or more other conduits or flow paths.

The terms "controlled compliance" and "controlled compliant" describe the ability to actively control the transfer of fluid volume into or out of a compartment, flow path or circuit. In certain embodiments, the variable volume of fluid in a dialysate circuit controlled or compliant flow path expands and contracts via the control of one or more pumps in conjunction with one or more reservoirs. The volume of fluid in the system is generally constant (unless additional fluids are added to a reservoir from outside of the system) once the system is in operation if the patient fluid volume(s), flow paths, and reservoirs are considered part of the total volume of the system (each individual volume may sometimes be referred to as a fluid compartment). The attached reservoirs allow the system to adjust the patient fluid volume by withdrawing fluid and storing the desired amount in an attached control reservoir and/or by providing purified and/or rebalanced fluids to the patient and optionally removing waste products. The terms "controlled compliance" and "controlled compliant" are not to be confused with the term "non-compliant volume," which simply refers to a vessel, conduit, container, flow path, conditioning flow path or cartridge that resists the introduction of a volume of fluid after air has been removed from a defined space such as a vessel, conduit, container, flow path, conditioning flow path or cartridge. In one embodiment, and as discussed herein and shown in the drawings is that the controlled compliant system can move fluids bi-directionally. In certain cases, the bi-directional fluid movement is across a semi-permeable membrane either inside or outside a dialyzer. The bi-directional fluid flow can also occur across, through, or between of vessels, conduits, containers, flow paths, conditioning flow paths or cartridges of the invention in selected modes of operation. The term "moving fluid bi-directionally" as used in connection with a barrier, such as a semi-permeable membrane, refers to the ability to move a fluid across the barrier in either direction. "Moving fluid bi-directionally" also can apply to the ability to move fluid in both directions in the flow path or between a flow path and reservoir in a controlled compliant system.

The terms "controlled compliant flow path", "controlled compliant dialysate flow path" and "controlled compliant solution flow path" refer to flow paths operating within a controlled compliant system having the characteristic of controlled compliance, or of being controlled compliant as defined herein.

The term "controller," "control unit," "processor," or "microprocessor" refers to a device which monitors and affects the operational conditions of a given system. The operational conditions are typically referred to as output variables of the system wherein the output variables can be affected by adjusting certain input variables.

The term "convective clearance" refers to the movement of solute molecules or ions across a semi-permeable barrier due to force created by solvent molecules moving across the semi-permeable barrier.

The terms "coordinately operates" and "coordinately operating" refer to controlling the function of two or more elements or devices so that the combined functioning of the two or more elements or devices accomplishes a desired result. The term does not exclusively imply that all such elements or devices are simultaneously energized.

The term "de-aeration" refers to removing some or all of the air contained in a liquid including both dissolved and non-dissolved air contained in the liquid.

The term "de-aeration flow path" or "de-aeration flow circuit" refers to a set of elements that are configured in fluid communication along a fluid flow pathway such a liquid can be passed through the fluid flow pathway to accomplish removal of some or all of the air or gas contained in the liquid, including removal of air or gas that is dissolved in the liquid.

The term "degas module" or "degassing module" refers to a component that separates and removes any portion of one or more dissolved or undissolved gas from a liquid. A degas module can include a hydrophobic membrane for allowing ingress or egress of gases through a surface of the module while preventing the passage of liquid through that surface of the module.

The term "deionization resin" refers to any type of resin or material that can exchange one type of ion for another. In one specific case, the term can refer to the removal of ions such as potassium, magnesium, sodium and calcium in exchange for hydrogen and/or sodium ions.

The term "detachable" refers to a characteristic of an object or apparatus that permits it to be removed and/or disconnected from another object or apparatus.

The term "dialysate" describes a fluid into or out of which solutes from a fluid to be dialyzed diffuse through a membrane. A dialysate typically contains electrolytes that are close in concentration to the physiological concentration of electrolytes found in blood. A common sodium level for dialysate is ~140 mEq/L. Normal blood sodium levels range from approximately 135 mEq/L to 145 mEq/L. The REDY system typically uses dialysate ranging from 120 mEq/L to 160 mEq/L. In certain embodiments, a "predetermined limit" or "predetermined concentration" of sodium values can be based off the common sodium levels for dialysate and normal blood sodium levels.

The term "dialysate flow loop," "dialysate flow path" or "dialysate conduit flow path" refers to any portion of a fluid pathway that conveys a dialysate and is configured to form at least part of a fluid circuit for hemodialysis, hemofiltration, hemodiafiltration or ultrafiltration The term "dialysate regeneration unit" or "dialysate regeneration system" refers to a system for removing certain electrolytes and waste species including urea from a dialysate after contact with a dialyzer. In certain instances, the component contained within the "dialysate regeneration unit" or "dialysate regeneration system" can decrease the concentration or conductivity of at least one ionic species, or release and/or absorb at least one solute from a dialysate.

"Dialysis" is a type of filtration, or a process of selective diffusion through a membrane. Dialysis removes solutes of a specific range of molecular weights via diffusion through a membrane from a fluid to be dialyzed into a dialysate. During dialysis, a fluid to be dialyzed is passed over a filter membrane, while dialysate is passed over the other side of that membrane. Dissolved solutes are transported across the filter membrane by diffusion between the fluids. The dialysate is used to remove or add solutes from the fluid to be dialyzed. The dialysate can also provide enrichment to the other fluid.

The terms "dialysis membrane," "hemodialysis membrane," "hemofiltration membrane," "hemodiafiltration membrane," "ultrafiltration membrane," can often generally be referred to as a "membrane," or can refer to a semi-permeable barrier selective to allow diffusion and/or convection of solutes between blood and dialysate, or blood and filtrate, of a specific range of molecular weights in either direction through the barrier that separates blood and dialysate, or blood and filtrate, while allowing diffusive and/or convective transfer between the blood on one side of the membrane and the dialysate or filtrate circuit on the other side of the membrane.

The term "dialyzer" refers to a cartridge or container with two flow paths separated by semi-permeable membranes. One flow path is for blood and one flow path is for dialysate. The membranes can be in the form of hollow fibers, flat sheets, or spiral wound or other conventional forms known to those of skill in the art. Membranes can be selected from the following materials of polysulfone, polyethersulfone, poly(methyl methacrylate), modified cellulose, or other materials known to those skilled in the art.

The term "diluent" or "diluate" refers to a fluid having a concentration of a specific species less than a fluid to which the diluent is added.

The term "disinfection fluid" refers to a solution for use in cleaning and disinfecting an apparatus for hemodialysis, hemodiafiltration or hemofiltration. The disinfection fluid may act thermally, chemically, and combinations thereof to inhibit growth of or to destroy microorganisms. The "disinfection fluid" may further act to remove, at least in part, a buildup of microorganisms on a surface of a fluid flow path, such buildups of microorganisms may be commonly referred to as a biofilm.

The terms "disposable" and "disposables" refer to any component that is suitable for one or multiple use, but requires replacement or refurbishment. Non-limiting examples include a disposable dialyzer, urea sensors, and a degassing module. Disposables can also mean components that have a limited life such as microbial filters, containers, replaceable reservoirs and the like.

The term "downstream" refers to a relative position in which components of the device or fluid have moved relative to which the dialysate or other fluid has moved within a conduit or flow path.

The term "downstream conductivity" refers to the conductivity of a fluid solution as measured at a location of a fluid flow path in the direction of the normal fluid flow from a reference point.

The term "drain connection" refers to being joined in fluid communication with a conduit or vessel that can accept fluid egress from the system.

The term "dry" as applied to a solid or a powder contained in a cartridge means not visibly wet, and may refer interchangeably to anhydrous and also to partially hydrated forms of those materials, for example, monohydrates and dihydrates.

The term "dry composition" refers to a compound that does not contain a substantial quantity of water and can include anhydrous forms as well as hydrates for example, monohydrates and dihydrates.

The term "effluent dialysate," as used herein describes the discharge or outflow from a dialyzer after the dialysate has been used for dialysis.

The term "electrode" as used herein describes an electrical conductor used to make contact with a part of a fluid, a solid or solution. For example, electrical conductors can be used as electrodes to contact any fluid (e.g. dialysate) to measure the conductivity of the fluid or deliver or receive charge to the fluid.

The term "electrolyte" refers to an ion or ions dissolved in an aqueous medium, including but not limited to sodium, potassium, calcium, magnesium, acetate and chloride.

The term "electrolyte source" "electrolyte source" refers to a stored substance that provides one or more electrolytes The terms "equilibrated," "equilibrate," "to equilibrate," and the like refer to a state where a concentration of a solute in a first fluid has become approximately equal to the concentration of that solute in the second fluid. However, the term equilibrated as used herein does not imply that the concentration of the solute in the first fluid and the second fluid have become equal. The term can also be used in reference to the process of one or more fluids coming into equilibrium where the fluids have equal pressures, such as between a liquid and a gas.

The terms "equilibrated," "equilibrate," "to equilibrate," and the like refer to a state where a concentration of a solute in a first fluid has become approximately equal to the concentration of that solute in the second fluid. However, the term equilibrated as used herein does not imply that the concentration of the solute in the first fluid and the second fluid have become equal. The term can also be used in reference to the process of one or more gases coming into equilibrium where the gases have equal pressures or between a liquid and a gas.

The phrase "equilibrated to the solute species concentration" refers to a concentration of a particular solute species in a first fluid that has become approximately equal to the concentration of that solute species in the second fluid. The concentration need not be exact.

The terms "evacuation volume", "priming volume" and "void volume" refer to the internal volume of a component or collection of components comprising a fluid flow path and are the volume of fluid that can be removed from the fluid flow path to empty the fluid flow path if it has been filled with fluid.

The term "extracorporeal," as used herein generally means situated or occurring outside the body.

The term "extracorporeal circuit" or "extracorporeal flow path" refers to a fluid pathway incorporating one or more components such as but not limited to conduits, valves, pumps, fluid connection ports or sensing devices configured therein such that the pathway conveys blood from a subject to an apparatus for hemodialysis, hemofiltration, hemodiafiltration or ultrafiltration and back to the subject.

The terms "extracorporeal flow path pump" and "blood pump" refer to a device to move or convey fluid through an extracorporeal circuit. The pump may be of any type suitable for pumping blood, including those known to persons of skill in the art, for example peristaltic pumps, tubing pumps, diaphragm pumps, centrifugal pumps, and shuttle pumps.

The terms "filtrate regeneration unit" and "filtrate regeneration system" refer, in context, to a system for removing certain electrolytes and waste species including urea from a filtrate produced using filtration.

The terms "filtrate regeneration circuit", "filtrate regeneration loop", and the like, refer to a flow path containing fluid resulting from filtration; for the removal of certain electrolytes and waste species including urea.

The term "filtration" refers to a process of separating solutes from a fluid, by passing the fluid through a filter medium across which certain solutes or suspensions cannot pass. Filtration is driven by the pressure difference across the membrane.

The term "first terminal end" of a flow path refers to one end of the flow path and "second terminal end" refers to another end of the flow path. Neither the "first terminal end" nor the "second terminal end" has any limitation on placement on an arterial or venous side.

The term "first terminal valve" refers to a valve substantially located at one end of a first fluid conduit without any requirement that the valve be place on an arterial or venous side. Similarly, the term "second terminal valve" refers to a valve substantially located at one end of a second fluid conduit and so on without any limitation on placement on an arterial or venous side The term "flow loop" refers to a grouping of components that may guide the movement of a fluid, convey the fluid, exchange energy with the fluid, modify the composition of the fluid, measure a characteristic of the fluid and/or detect the fluid. A flow loop comprises a route or a collection of routes for a fluid to move within. Within a flow loop there may be more than one route that a volume of fluid can follow to move from one position to another position. A fluid volume may move through a flow loop such that it recirculates, or passes the same position more than once as it moves through a flow loop. A flow loop may operate to cause fluid volume ingress to and fluid volume egress from the flow loop. The term "flow loop" and "flow path" often may be used interchangeably. Further types of flow paths may be further defined; for example, (1) a recirculation flow path, would be a flow path whose function is in whole or part is to recirculate fluid through the defined flow path; (2) a dialyzer recirculation flow path would be a flow path whose function is in whole or part is to recirculate fluid through the defined flow path having a dialyzer' (3) a controlled compliant flow path would be a flow path would be a flow path that is controlled compliant as defined herein. Any of the defined flow paths may be referred to numerically, as a first flow path, second, third flow path, or fourth flow path, and the like flow paths.

The term "flow path" refers to a route or a collection of routes for a fluid to move within. Within a flow path there may be more than one route that a fluid can follow to move from a first position to a second position. A fluid may move through a flow path such that it recirculates, or passes the same position more than once as it moves through a flow path. A flow path may be a single element such as a tube, or a flow path may be a grouping of components of any type that guide the movement of a fluid. The term "flow loop" and "flow path" often may be used interchangeably.

The terms "flow restriction" and "flow restriction device" and "flow restrictor" refer to an element or grouping of elements that resist the flow of fluid through the element or grouping of elements such that the fluid pressure within a flow stream that passes through the element or grouping of elements is greater upstream of the element or grouping of elements than downstream of the element or grouping of elements. A flow restrictor may be an active or passive device. Non-limiting examples of passive flow restriction devices are orifices, venturis, a narrowing, or a simple length of tubing with flow cross section that produces the desired pressure drop when the fluid flows through it, such tubing being essentially rigid or compliant. Non-limiting examples of active flow restrictors are pinch valves, gate valves and variable orifice valves. The term "flow stream" refers to fluid moving along a flow path.

The term "fluid balance control pump" refers to where a control pump is used to adjust the concentration or amount of a solute or fluid in the system. For example, a fluid balance control pump is used for selectively metering in or selectively metering out a designated fluid wherein the concentration or amount of a solute or fluid is adjusted The term "fluid communication" refers to the ability of fluid to move from one part, element, or component to another; or the state of being connected, such that fluid can move by pressure differences from one portion that is connected to another portion.

The term "fluid port" refers to an aperture through which a liquid or gas can be conveyed.

The term "fluid port cap or plug" refers to a device that can be connected to a fluid port to prevent fluid from passing through the fluid port. A fluid cap or plug may be configured into an apparatus having multiple caps or plugs to prevent fluid from passing through multiple fluid ports when the apparatus is connected to the multiple fluid ports.

The term "fluid port jumper" refers to a device that can be connected between two or more fluid ports to enable a fluid to move between the two or more fluid ports by passing through the device. A fluid port jumper can be a discrete tube or conduit. Multiple fluid port jumpers can be arranged into an assembly such as a cleaning manifold.

The term "flush reservoir" is used to describe a container that can accept or store fluid that is removed from the system during rinsing or cleaning of fluid pathways of the system, including draining the system after cleaning and/or disinfection has been completed.

The term "gas port" refers to an aperture through which any gaseous form of matter can be conveyed.

"Gas phase pressure" also known as "vapor" is the equilibrium pressure from a liquid or a solid at a specific temperature. If the vapor is in contact with a liquid or solid phase, the two phases will be in a state of equilibrium.

"Hemodiafiltration" is a therapy that combines hemofiltration and hemodialysis.

"Hemodialysis" is a technique where blood and a "cleansing fluid" called dialysate are exposed to each other separated by a semi-permeable membrane. Solutes within the permeability range of the membrane pass while diffusing along existing concentration gradients. Water and solutes are also transferred by convection across a pressure gradient that may exist across the dialysis membrane. The dialysate employed during hemodialysis has soluble ions such as sodium, calcium and potassium ions and is not pure water. The sieving properties of the membrane exclude certain solutes above a certain threshold from crossing the membrane. One common sieving property is "albumin sieving." In most situations it is not desirable to remove albumin during renal replacement therapy, as lower blood serum albumin is associated with increased mortality rates.

The term "hemofilter" refers to a apparatus (or may refer to a filter) used in hemofiltration. A hemofilter apparatus can be connected to an extracorporeal circuit and configured to operate with a semipermeable membrane that separates at least a portion of the fluid volume from blood to produce a filtrate fluid.

"Hemofiltration" is a therapy in which blood is filtered across a semi-permeable membrane. Water and solutes are removed from the blood via pressure-driven convection across the membrane. The sieving properties of the membrane exclude certain solutes above a certain threshold from crossing the membrane. One common sieving property is "albumin sieving." In most situations it is not desirable to remove albumin during renal replacement therapy, as lower blood serum albumin is associated with increased mortality rates. In hemofiltration, solutes small enough to pass through the membrane in proportion to their plasma concentration are removed. The driving force is a pressure gradient rather than a concentration gradient. A positive hydrostatic pressure drives water and solutes across the filter membrane from the blood compartment to the filtrate compartment, from which it is drained. Solutes, both small and large, get dragged through the membrane at a similar rate by the flow of water that has been engineered by the hydrostatic pressure. Hence, convection overcomes the reduced removal rate of larger solutes (due to their slow speed of diffusion) observed in hemodialysis. The rate of solute removal is proportional to the amount of fluid removed from the blood circuit, which can be adjusted to meet the needs of a clinical situation. In general, the removal of large amounts of plasma water from the patient requires volume substitution. Substitution fluid, typically a buffered solution close to the plasma water composition a patient needs, can be administered pre or post filter (pre-dilution mode, post-dilution mode).

The term "hydrophobic membrane" refers to a semipermeable porous material that may allow gas phases of matter to pass through, but which substantially resists the flow of water through the material due to the surface interaction between the water and the hydrophobic material.

The terms "hydrophobic vent" and "hydrophobic vent membrane" refer to a porous material layer or covering that can resist the passage of a liquid such as water through the pores while allowing the passage of a gas. The pores may also be of a sufficiently small size to substantially prevent the passage of microorganisms.

The term "impedance meter" refers to a device for measuring the opposition of an object or structure to an alternating current.

The terms "impurity", or "impurity species" refer to a molecular or ionic species that originates from tap water, a sorbent cartridge, a source other than a patient's or the subject's blood including, for example, but limited to chlorine, fluoride ions, and aluminum-containing species. The term "impurity species" can also refer to solutes in a blood that are in too high of a concentration in the blood from standard ranges known in the art or that are solutes that have resulted from metabolism to generate a non-healthy component now residing in the blood. In certain instances, an "impurity species" can also be regarded as a "waste species," or "waste products."

The terms "infusate container" and "infusate reservoir" refer to a vessel, which can be substantially flexible or non-flexible for holding a solution, for example a solution of one or more salts, for the adjustment of the composition of a dialysate.

The term "infusate solution" refers to a solution of one or more salts or chemicals for the adjustment of the composition of a dialysate, such as salts of calcium, magnesium and potassium, and glucose.

The term "infusate system" refers to a system that incorporates at least one fluid pathway including components such as conduits, valves, pumps or fluid connection ports, an infusate container or a controller configured to add an infusate solution to a dialysate.

The term "interchangeable bicarbonate cartridge" refers to a bicarbonate cartridge that can be configured for removal and replacement with a like bicarbonate cartridge. Interchangeable bicarbonate cartridges can be single use disposable, or re-fillable, re-usable containers.

The term "interchangeable sodium chloride cartridge" refers to a sodium chloride cartridge that can be configured for removal and replacement with a like sodium chloride cartridge. Interchangeable sodium chloride cartridges can be single use disposable, or re-fillable, re-usable containers.

The terms "introduce" and "introducing" refer to causing a substance to become present where it was not present, or to cause the amount or concentration of a substance to be increased.

The term "ion-exchange material" refers to any type of resin or material that can exchange one type of ion for another. The "ion-exchange material" can include anion and cation exchange materials. In one specific case, the term can refer to the removal of ions such as potassium, magnesium, sodium, phosphate and calcium in exchange for other ions such as potassium, sodium, acetate, hydrogen and/or hydroxide.

An "ion-exchange resin" or "ion-exchange polymer" is an insoluble matrix (or support structure) that can be in the form of small (1-2 mm diameter) beads, fabricated from an organic polymer substrate. The material has a developed structure of pores on the surface of which are sites with easily trapped and released ions. The trapping of ions takes place only with simultaneous releasing of other ions; thus the process is called ion-exchange. There are multiple different types of ion-exchange resins which are fabricated to selectively prefer one or several different types of ions. In one specific case, the term can refer to the removal of ions such as potassium, magnesium, sodium, phosphate and calcium in exchange for other ions such as potassium, sodium, acetate, hydrogen and/or hydroxide.

The term "ion selective electrode" refers to electrodes coated with a material that only allows certain ions to pass through. An "ion selective electrode" (ISE), also known as a specific ion electrode (SIE), is a transducer (or sensor) that converts the activity of a specific ion dissolved in a solution into an electrical potential, which can be measured by a voltmeter or pH meter. The voltage is theoretically dependent on the logarithm of the ionic activity, according to the Nernst equation. The sensing part of the electrode is usually made as an ion-specific membrane, along with a reference electrode.

The term "jumper" refers to a fluid conduit that completes a fluid pathway at least between two or more points of connection within a fluid circuit. The term "jumper" is not limited to a tube shaped item, but may be any component or arrangement of components that allows fluid to pass from at least a first point of connection to at least a second point of connection.

The term "jumpered port" refers to any connection opening that may be connected to another connection opening by an intermediate component or grouping of components to allow a fluid flow to occur between the said connection openings. The jumpered port can be configured to interface with a fluid conduit, pathway or passageway external to a unit or module having the jumpered port. The term "jumpered port" is intended to be interpreted in its broadest sense and encompasses any facilitation of fluid from one flow path or segment of a flow path to another using any of holes, fittings, fixtures, outlet, inlet, orifice, connectors, couplings, junctions or the like.

The term "junction" refers to a common point of connection between two or more flow paths or conduits that allows a liquid and/or a gas to move from one pathway or conduit to another. A junction may be a reversible connection that can be separated when transfer of a liquid and/or gas between the flow paths or conduits is not needed The term "kidney replacement therapy" as used herein describes the use of a provided system to replace, supplement, or augment the function of a patient with impaired kidney function, such as would occur for a patient with Chronic Kidney Disease. Examples of kidney replacement therapy would include dialysis, hemofiltration, hemodialysis, hemodiafiltration, peritoneal dialysis, and the like.

The term "luer connector" or "luer adapter" refers to adapters or connectors conforming to International Standards Organization (ISO) standards 594-2.

The term "manifold" refers to a collection of one or more fluid pathways that are formed within a single unit or subassembly. Many types of manifolds can be used, e.g. a cleaning and/or disinfecting manifold is used to clean or disinfect the defined flow loop when the flow loop is connected to the cleaning and/or disinfecting manifold.

The term "material layer" refers to the layers of materials found in a sorbent cartridge. The material layers in a sorbent cartridge may have one or more layers selected from a urease-containing material, alumina, zirconium phosphate, zirconium oxide, and activated carbon.

The term "memory" refers to a device for recording digital information that can be accessed by a microprocessor, such as RAM, Dynamic RAM, microprocessor cache, FLASH memory, or memory card.

The term "metabolic waste species," as used herein describes organic and inorganic components generated by a patient. They can be metabolic products such as urea, uric acid, creatinine, chlorides, inorganic sulfates and phosphate, or excess electrolytes such as sodium, potassium, etc. It will be understood that the specific "metabolic waste species" can vary between individuals depending on diet and environmental factors. Hence, the term is intended to encompass any waste component that is normally removed by a kidney or by dialysis without restriction on the specific type of waste substance.

The term "microbial filter" refers to a device configured to inhibit the passage of microbes or fragments of microbes such as endotoxins conveyed by a fluid or solution while allowing the passage of the fluid or solution.

The term "mid-weight uremic wastes" refers to substances that can pass through a dialysis membrane and have a molecular weight less than about 66,000 g/mol and greater than about 1000 g/mol. An example of a middle molecule is beta-2 microglobulin.

The term "moving fluid bi-directionally" as used in connection with a barrier, such as a semi-permeable membrane, refers to the ability to move a fluid across the barrier in either direction. "Moving fluid bi-directionally" also can apply to the ability to move fluid in both directions in the flow loop in a controlled compliant system.

The term "nitrogenous waste" refers to any non-polymeric nitrogen-containing organic compound originating from the blood of a patient. Nitrogenous waste includes urea and creatinine, which are both "waste species."

The term "one-way valve" refers to a device that allows flow to pass in one direction through the valve, but prevents or substantially resists flow through the valve in the opposite direction. Such devices can include devices commonly referred to as check valves.

The term "osmolarity" is defined as the number of osmoles of a solute per liter of solution. Thus, a "hyperosmolar solution" represents a solution with an increase in osmolarity compared to physiologic solutions. Certain compounds, such as mannitol, may have an effect on the osmotic properties of a solution as described herein.

The term "parallel or wound hollow fiber assembly" refers to any device that incorporates a porous or non-porous hollow fiber material that allows a gas to pass through the material wall of the hollow fibers, but resists the passage of a liquid through the material wall and is configured as multiple strands aligned in parallel or wrapped around a core. The liquid to be degassed may be conveyed through either the inside of the hollow fibers or around the outside of the hollow fibers. Optionally, a gas may be conveyed on the side of the material wall that is opposite the liquid to be degassed. Optionally, a vacuum may be applied on the side of the material wall that is opposite the liquid to be degassed.

The terms "pathway," "conveyance pathway" and "flow path" refer to the route through which a fluid, such as dialysate or blood travels.

A "patient" or "subject" is a member of any animal species, preferably a mammalian species, optionally a human. The subject can be an apparently healthy individual, an individual suffering from a disease, or an individual being treated for a disease.

The term "patient fluid balance" refers to the amount or volume of fluid added to or removed from a subject undergoing a treatment.

The term "peristaltic pump" refers to a pump that operates by compression of a flexible conduit or tube through which the fluid to be pumped passes.

"Peritoneal dialysis" is a therapy wherein a dialysate is infused into the peritoneal cavity, which serves as a natural dialyzer. In general, waste components diffuse from a patient's bloodstream across a peritoneal membrane into the dialysis solution via a concentration gradient. In general, excess fluid in the form of plasma water flows from a patient's bloodstream across a peritoneal membrane into the dialysis solution via an osmotic gradient.

The term "physiologically compatible fluid" or "physiological compatible solution" refers to a fluid that can be safely introduced into the bloodstream of a living subject.

The term "plumbing," as used herein generally describes any system of valves, conduits, channels, and lines for supplying and directing any of the fluids used in the invention.

The term "priming process" refers to the process of conveying a liquid into the void volume of a fluid pathway to fill the pathway with liquid.

The term "porosity," as used herein describes the fraction of open pore volume of a membrane.

The terms "portable system" or "wearable system" refers to a system in whole or in part having a mass and dimension to allow for transport by a single individual by carrying the system or wearing the system on the individual's body. The terms are to be interpreted broadly without any limitation as to size, weight, length of time carried, comfort, ease of use, and specific use by any person whether man, woman or child. The term is to be used in a general sense wherein one of ordinary skill will understand that portability as contemplated by the invention encompasses a wide range of weights, geometries, configurations and size.

The term "potable water" refers to drinking water or water that is generally safe for human consumption with low risk of immediate or long term harm. The level of safety for human consumption can depend on a particular geography where water safe for human consumption may be different from water considered safe in another jurisdiction. The term does not necessarily include water that is completely free of impurities, contaminants, pathogens or toxins. Other types of water suitable for use in the present invention can include purified, deionized, distilled, bottled drinking water, or other pre-processed water that would be understood by those of ordinary skill in the art as being suitable for use in dialysis The term "prefilled" refers to a substance that has been added in advance.

The terms "pressure differential" and "pressure drop" refer to the difference in pressure measurements of a fluid between two points of measurement.

The terms "pressure meter" and "pressure sensor" refer to a device for measuring the pressure of a gas or liquid in a vessel or container.

The term "priming fluid" refers to a liquid that can be used to displace gas from a flow path.

The term "priming overflow reservoir" refers to a reservoir which during priming is used to collect the overflow of fluid during the priming process.

The term "priming process" or "priming" refers to the process of conveying a liquid into the void volume of a fluid pathway to fill the pathway with liquid.

The term "priming volume" refers to the volume of priming fluid required to fill the void volume of the subject pathway, device, or component, as the particular case may be.

The terms "processor," "computer processor," and "microprocessor" as used herein are broad terms and are to be given their ordinary and customary meaning to a person of ordinary skill in the art. The terms refer without limitation to a computer system, state machine, processor, or the like designed to perform arithmetic or logic operations using logic circuitry that responds to and processes the basic instructions that drive a computer. In some embodiments, the terms can include ROM ("read-only memory") and/or RAM ("random-access memory") associated therewith.

The term "programmable" as used herein refers to a device using computer hardware architecture with a stored program and being capable of carrying out a set of commands, automatically that can be changed or replaced.

The term "pulsatile pump" refers to a pump where the pumped fluid undergoes periodic variation in velocity and/or pressure.

The term "pump" refers to any device that causes the movement of fluids or gases by the application of suction or pressure.

The terms "pump rate" and "volumetric pumping rate" refer to the volume of fluid that a pump conveys per unit of time.

The term "purified water" refers to water that has been physically processed to remove at least a portion of at least one impurity from the water.

The terms "reconstitute" or "reconstituting" refer to creating a solution by addition of a liquid to a dry material or to a solution of higher concentration to change the concentration level of the solution.

The term "refilled" refers to having replenished or restored a substance that has been consumed or degraded.

The term "remnant volume" or "residual volume" refers to the volume of fluid remaining in a fluid flow path after the fluid flow path has been partially emptied or evacuated.

The terms "replacement fluid" and "substitution fluid" refer to fluid that is delivered to the blood of a subject undergoing convective renal replacement therapies such as hemofiltration or hemodiafiltration in order to replace at least a portion of the fluid volume that is removed from the subject's blood when the blood is passed through a hemofilter or a dialyzer.

The term "replenished" refers to having refilled or restored a substance that has been consumed or degraded.

The term "reserve for bolus infusion" refers to an amount of solution available, if needed, for the purpose of administering fluid to a subject receiving therapy, for example, to treat an episode of intradialytic hypotension.

The term "reusable" refers to an item that is used more than once. Reusable does not imply infinitely durable. A reusable item may be replaced or discarded after multiple uses.

The term "reversible connections" refers to any type of detachable, permanent or non-permanent connection configured for multiple uses.

The term "salination pump" refers to a pump configured to move fluid and/or control movement of fluid through a conditioning flow path, such as through or from a source of a conditioning material such as sodium chloride or sodium bicarbonate.

The term "salination valve" refers to a valve configured to control the flow of fluid in a conditioning flow path, such as through or from a source of a conditioning material such as sodium chloride or sodium bicarbonate.

The term "segment" refers to a portion of the whole, such as a portion of a fluid flow path or a portion of a fluid circuit. A segment is not limited to a tube or conduit, and includes any grouping of elements that are described for a particular segment. Use of the term "segment", by itself, does not imply reversible or detachable connection to another segment. In an embodiment, a segment may be permanently connected to one or more other segments or removably or detachably connected to one or more segments.

The terms "selectively meter fluid in" or "selectively meter fluid out" generally refer to a process for controllably transferring fluids from one fluid compartment (e.g. a selected patient fluid volume, flow path, or reservoir) to another fluid compartment. One non-limiting example is where a control pump may transfer a defined fluid volume container, reservoirs, flow paths, conduit of the controlled compliant system. When fluid is moved from a reservoir into another part of the system, the process is referred to as "selectively metering fluid in" as related to that part of the system. Similarly, one non-limiting example of removing spent dialysate from a dialysate flow path in a controlled compliant system and storing the spent dialysate in a control reservoir, wherein a defined volume of the spent dialysate is transferred to a reservoir, such as a control reservoir can be referred to as "selectively metering-out" the fluid from the dialysate flow path.

The term "semipermeable membrane," also termed a "selectively permeable membrane," a "partially permeable membrane," or a "differentially permeable membrane," is a membrane that will allow certain molecules or ions to pass through it by diffusion and occasionally specialized "facilitated diffusion." The rate of passage depends on the pressure, concentration, and temperature of the molecules or solutes on either side, as well as the permeability of the membrane to each solute. The term "semi-permeable membrane" can also refer to a material that inhibits the passage of larger molecular weight components of a solution while allowing passage of other components of a solution having a smaller molecular weight. For example, Dialyzer membranes come with different pore sizes. Those with smaller pore size are called "low-flux" and those with larger pore sizes are called "high-flux." Some larger molecules, such as beta-2-microglobulin, are not effectively removed with low-flux dialyzers. Because beta-2-microglobulin is a large molecule, with a molecular weight of about 11,600 daltons, it does not pass effectively through low-flux dialysis membranes.

The term "sensor," which can also be referred to as a "detector" in certain instances, as used herein can be a converter that measures a physical quantity of a matter in a solution, liquid or gas, and can convert it into a signal which can be read by an electronic instrument.

The term "sensor element" refers to a device or component of a system that detects or measures a physical property.

The term "shunt," as most often used herein describes a passage between channels, in the described filtration and purification systems, wherein the shunt diverts or permits flow from one pathway or region to another. An alternate meaning of "shunt" can refer to a pathway or passage by which a bodily fluid (such as blood) is diverted from one channel, circulatory path, or part to another. At times the term "bypass" maybe used interchangeable with the term "shunt."

The term "sodium source" refers to a source from which sodium can be obtained. For example, the sodium source can be a solution containing sodium chloride or a dry sodium chloride composition that is hydrated by the system.

The terms "sodium chloride cartridge" and "sodium chloride container" refer to an object that can be a stand-alone enclosure or alternatively can be integrally formed with an apparatus for hemodialysis, hemodiafiltration, or hemofiltration. The object can store a source of sodium, such as sodium chloride in solid and/or solution form, and can be configured to interface with at least one other functional module found in systems for hemodialysis, hemodiafiltration, or hemofiltration. For example, the sodium chloride cartridge or container can contain at least one fluid pathway and include components such as conduits, valves, filters or fluid connection ports.

The term "sodium conduit flow path" refers to a flow path in fluid communication with a sodium chloride cartridge which then can pump saturated sodium solution into the dialysate by pumping and metering action of a salination pump.

The term "sodium source" refers to a source from which sodium can be obtained. For example, the sodium source can be a solution containing sodium chloride or a dry sodium chloride composition that is hydrated by the system The term "solid bicarbonate" refers to a composition containing a salt of bicarbonate such as sodium bicarbonate at any purity level. In general, the solid bicarbonate will be easily soluble in water to form a solution.

The term "solute" refers to a substance dissolved, suspended, or present in another substance, usually the component of a solution present in the lesser amount.

The term "solution regeneration system" refers to one or more sorbent materials for removing specific solutes from solution, such as urea. "Solution regeneration system" includes configurations where at least some of the materials contained in the system do not act by mechanisms of adsorption or absorption. The materials that comprise the solution regeneration system may be configured in a single container or sorbent cartridge, or in separate containers or cartridges.

The terms "sorbent cartridge" and "sorbent container" interchangeably refer to an enclosure having one or more sorbent materials for removing specific solutes from solution, such as urea. In certain embodiments, the term "sorbent cartridge" includes configurations where at least some of the materials contained in the cartridge do not act by mechanisms of adsorption or absorption.

The terms "sorbent regeneration," "sorbent regeneration system," "sorbent system, and the like, refer, in context, to devices that are part of a sorbent regenerated dialysate delivery system for hemodialysis, functioning as an artificial kidney system for the treatment of patients with renal failure or toxemic conditions, and that consists of a sorbent cartridge and the means to circulate dialysate through this cartridge and the dialysate compartment of the dialyzer. The device is used with the extracorporeal blood system and the dialyzer of the hemodialysis system and accessories. The device may include the means to maintain the temperature, conductivity, electrolyte balance, flow rate and pressure of the dialysate, and alarms to indicate abnormal dialysate conditions. The sorbent cartridge may include absorbent, ion exchange and catalytics.

The term "source of cations" refers to a source from which cations can be obtained. Examples of cations include, but are not limited to, calcium, magnesium and potassium. The source can be a solution containing cations or a dry composition that is hydrated by the system. The cation infusate source is not limited to cations and may optionally include other substances to be infused into a dialysate or replacement fluid. Non-limiting examples include glucose, dextrose, acetic acid and citric acid.

The term "specified gas membrane permeability" refers to a determined rate at which a membrane will allow a gas to pass through the membrane from a first surface to a second surface, the rate being proportional to the difference in absolute pressure of the gas in proximity to the first side of the membrane and in proximity to the second side of the membrane.

The term "spent dialysate" refers to a dialysate that has exchanged solutes and/or water with blood through a dialysis membrane and contains one or more impurity, or waste species, or waste substance, such as urea.

The term "static mixer" refers to a device that mixes two or more component materials in a fluid solution without requiring the use of moving parts.

The term "substantially inflexible volume" refers to a three-dimensional space within a vessel or container that can accommodate a maximum amount of non-compressible fluid and resists the addition of any volume of fluid above the maximum amount. The presence of a volume of fluid less than the maximum amount will fail to completely fill the vessel or container. Once a substantially inflexible volume has been filled with a fluid, removal of fluid from that volume will create a negative pressure that resists fluid removal unless fluid is added and removed simultaneously at substantially equal rates. Those skilled in the art will recognize that a minimal amount of expansion or contraction of the vessel or container can occur in a substantially inflexible volume; however, the addition or subtraction of a significant volume of fluid over a maximum or minimum will be resisted.

The term "tap water" refers to water, as defined herein, from a piped supply.

The term "temperature sensor" refers to a device that detects or measures the degree or intensity of heat present in a substance, object, or fluid.

The term "therapy cassette" refers to a detachable set of one or more components that can be connected to an apparatus for performing hemodialysis, hemodiafiltration, or hemofiltration. A connection between a therapy cassette and an apparatus may be for purposes including, but not limited to, maintaining a position, allowing a flow of fluid, performing a measurement, transmitting power, and transmitting electrical signals. A therapy cassette can incorporate at least one fluid pathway, and any one or combination of the following exemplary, non-limiting components such as conduits, fluid connection ports, concentrates, cartridges, valves, sensor elements, reservoirs, filters, vents, dialyzers, and disposable and consumable components. A therapy cassette can be configured to interface with at least one other module of a dialysis apparatus such as a base module, to form at least one complete fluid circuit such as a controlled compliant flow path or a blood circuit for performing hemodialysis, hemodiafiltration, or hemofiltration. One or more components in a cassette can be any combination of single use, disposable, consumable, replaceable, or durable items or materials.

A 'therapy solution reservoir" refers to any container or reservoir that holds a physiological compatible fluid.

The terms "treating" and "treatment" refer to the management and care of a patient having a pathology or condition by administration of one or more therapy contemplated by the present invention. Treating also includes administering one or more methods of the present invention or using any of the systems, devices or compositions of the present invention in the treatment of a patient. As used herein, "treatment" or "therapy" refers to both therapeutic treatment and prophylactic or preventative measures. "Treating" or "treatment" does not require complete alleviation of signs or symptoms, does not require a cure, and includes protocols having only a marginal or incomplete effect on a patient.

The term "ultrafiltrate" refers to fluid that is removed from a subject by convection through a permeable membrane during hemodialysis, hemofiltration, hemodiafiltration, or peritoneal dialysis. The term "ultrafiltrate," as used herein, can also refer to the fluid in a reservoir that collects fluid volume removed from the patient, but such a reservoir may also include fluids or collections of fluids that do not originate from the subject.

The term "ultrafiltration" refers to subjecting a fluid to filtration, where the filtered material is very small; typically, the fluid comprises colloidal, dissolved solutes or very fine solid materials, and the filter is a microporous, nanoporous, or semi-permeable medium. A typical medium is a membrane. During ultrafiltration, a "filtrate" or "ultrafiltrate" that passes through the filter medium is separated from a feed fluid. In certain instances, the use of the term "filtrate" can refer to the fluid generated during hemofiltration. In general, when transport across a membrane is predominantly diffusive as a result of a concentration driving force, the process is described herein as dialysis. When transport is primarily convective as a result of bulk flow across the membrane induced by a pressure driving force, the process is ultrafiltration or hemofiltration depending on the need for substitution solution as the membrane passes small solutes but rejects macromolecules. The term "ultrafiltration" can also refer to the fluid removal from blood during a dialysis or a hemofiltration process. That is, ultrafiltration refers to the process of passing fluid through a selective membrane, such as a dialysis or hemofiltration membrane, in dialysis, hemodiafiltration, or a filtration process.

The terms "unbuffered sodium bicarbonate" or "solution of unbuffered sodium bicarbonate" refer to a sodium bicarbonate composition that is not buffered with a conjugate acid or base in any amount, proportion or pH adjustment.

The term "upper position" and "lower position" are relative terms to each other wherein the upper position is at a higher elevation than the lower position.

The term "upstream" refers to a direction opposite to the direction of travel of a moving dialysate or other fluid within a conduit or flow path The term "urea sensor" refers to a device for measuring or allowing for the calculation of urea content of a solution. The "urea sensor" can include devices measuring urease breakdown of urea and measurement of the resulting ammonium concentration. The sensing methods can be based on any one of conductimetric, potentiometric, thermometric, magnetoinductic, optical methods, combinations thereof and other methods known to those of skill in the art.

The term "uremic wastes" refers to a milieu of substances found in patients with end-stage renal disease, including urea, creatinine, beta-2-microglobulin.

The term "user input surface" refers to a surface that incorporates a user interface incorporating one or more components such as a display screen, a keyboard, a mouse, a microphone, at least one speaker or a touch screen accessible by a human for communicating input data to an apparatus or a controller The term "user interface module" refers to a device that incorporates one or more components such as a display screen, a keyboard, a mouse, a microphone, speaker or a touch screen configured to facilitate communication between a human and an apparatus or a controller The term "vacuum" refers to an action that results from application of a pressure that is less than atmospheric pressure, or negative to the reference fluid or gas The term "vent" as referred to in relationship to a gas, refers to permitting the escape of a gas from a defined portion of the system, such as, for example, as would be found in the degassing module.

The term "void volume" refers to a specific volume that can be occupied by a fluid in a defined space such as a controlled compliant flow path of the invention including all components contained therein.

The term "waste fluid" refers to any fluid that does not have a present use in the operation of the system. Non-limiting examples of waste fluids include ultrafiltrate, or fluid volume that has been removed from a subject undergoing a treatment, and fluids that are drained or flushed from a reservoir, conduit or component of the system.

The term "waste species," "waste products" or "impurity species" refers to any molecular or ionic species originating from the patient or subject, including metabolic wastes, molecular or ionic species including nitrogen or sulfur atoms, mid-weight uremic wastes and nitrogenous waste. Waste species are kept within a specific homeostasis range by individuals with a healthy renal system.

The term "water source" refers to a source from which potable or not potable water can be obtained.

The term "water source connection" or "water feed" refers to a state of fluid communication that enables water to be obtained from a water source and connected or fed into a receiving source or flow path.

The term "within" when used in reference to the a sensor located "within" the sorbent cartridge refers to all or part of the electrode is located inside or encased by at least part of the inner chamber formed from the sorbent cartridge wall.

The term "working dialysate solution" refers to a dialysate solution that is undergoing active circulation or movement through a system including conduits, pathways, dialyzers and cartridges.

Modular Dialysis Systems with Jumpered Circuits

The therapy system and methods of the present invention can provide for dialysis therapy to be conducted remote from a high volume purified water source and drain infrastructure and can be configured into a mechanical package that will minimize the burden for system storage, transport, setup, operation, and routine maintenance. The present invention can further perform all functions necessary to conduct a dialysis session, as well as routine cleaning and disinfection maintenance with input of only a limited volume of potable tap, or bottled drinking water or other suitable types of water that can be used in any of hemodialysis, hemofiltration, hemodiafiltration and peritoneal dialysis.

In some embodiments, the consumables can be configured within an integrated therapy disposables and consumables cassette to simplify equipment setup for a therapy session. A therapy cassette can have at least one fluid pathway that is a part of a module or system for hemodialysis, hemodiafiltration, or hemofiltration. The cassette can have one or more fluid pathways wherein connection to the module or system completes a controlled compliance dialysate flow path. It will be understood that a therapy cassette can contain any one or combination of conduits for providing a flow path and fluid connection ports for connecting a therapy cassette to the module. A therapy cassette can also contain any number of concentrates, cartridges, sensor elements, reservoirs, filters, vents to assist in the operation of the system. The cassette can include dialyzers defined as "disposables" herein wherein a dialyzer can be made integral to the therapy cassette or made fully removable. A fully detachable dialyzer wherein all functional components are removed from the therapy cassette are also contemplated by the invention. A therapy cassette can contain consumable components as defined herein such as sodium and salts thereof, bicarbonates and salts thereof and other electrolytes and salts thereof. In certain embodiments, the inclusion of such consumable components is critical to the invention by providing all necessary components for dialysis therapy in one module. A therapy cassette can have one consumable component such as sodium or bicarbonate, or both. A therapy cassette may also contain any number of sensors, plumbing and connections necessary to complete a dialysate flow path between the therapy cassette and the base module or apparatus. In particular, a therapy cassette can be configured to interface with at least one other module of a dialysis apparatus such as a base module, to form at least one complete fluid circuit such as a controlled compliant flow path or a blood circuit for performing hemodialysis, hemodiafiltration, or hemofiltration.

In certain embodiments, the therapy disposable and consumable components can be advantageously configured into subgroupings to be installed on a base module, or even configured as individual components to be installed on a base module. When installed onto the base module, the flow paths contained within individual or subgrouped components combine with the base module to form a completed controlled compliance dialysate fluid circuit for hemodialysis, hemodiafiltration, or hemofiltration. Such configurations can be advantageous when it is desired to customize a therapy setup, for example, to use a particular dialyzer or acid concentrate solution; or where economic preference favors re-use of certain components, such as in the case of refilling of a bicarbonate consumables container.

The system prepares its own priming solution and conducts priming of the dialysate and extracorporeal flow paths automatically. A separate supply of packaged or prepared sterile saline is not required for priming, fluid bolus, or blood rinse back when using this system. In certain embodiments, normal saline is around 0.9% by weight and is commonly used for priming dialyzers and extracorporeal circuits is 154 mEq/L. Certain portions of the dialysate circuit are re-used and routine cleaning and disinfection maintenance of this fluid circuit is performed automatically with a simple cleaning manifold. The system can be configured so that the cleaning manifold is stored and transported in-situ and without opening the disinfected flow path. The system can also be configured with design features that enable it to fold into a small, self-protective form that may be readily transported by the user. In some embodiments, the space required for stowed transport or stationary storage is compatible with airline carry-on luggage size allowances. For example, in some, non-limiting embodiments, weights of less than 15 kilograms and stowed configurations of less 40 liters volume are contemplated by the present invention.

In the described controlled compliant flow path of the present invention, net passive movement of fluid volume across the dialysis membrane due to operational pressure changes is eliminated. The invention provides for the ability to accurately control net patient fluid removal, and/or diffusive clearance combined with increased clearance via convection, and/or active provisioning of extra fluid to a patient. The system allows priming of the controlled compliant flow path and extracorporeal flow path, a fluid bolus, or the return of blood from the system back to the patient without requirement to provide for additional fluids from a separate source. The invention can actively provide fluid to the patient when the patient becomes hypotensive or hypovolemic, and can displace the internal volume of a blood circuit with a physiological solution when a patient is taken off a system. The invention can also provide for actively enhanced convective clearance by alternately varying the rate and/or direction of the fluid balance control pump. Any combination of the above mentioned features is contemplated by the invention. The system can optionally account for an infusate volume, provide additional convective clearance, and/or provide control of the entire process. The controlled compliant flow path can have one or more means for selectively metering fluid into and out of the controlled compliant flow path. The means can be any one of control pump, a water pump, a salination pump, an acid concentrate pump, and combinations thereof and, in some cases, a replacement fluid pump. The described controlled compliant flow path also simplifies the entire system. Specifically, balance chambers, scales or gravimetric control methods are not required to balance fluid removal with fluid replacement.

FIG. 1 shows a system for circulating blood and a dialysate through a dialyzer 701. A shunt such as a needle or catheter is connected to a patient's vasculature to draw blood and circulate the patient's blood through an extracorporeal flow path 100. The portion of the extracorporeal flow path 100 that contains drawn blood from the patient can be referred to as the arterial line 102, which by convention is understood to mean a line for transporting blood from the patient regardless of whether blood is drawn from an artery or vein of the patient. Similarly, the portion that returns blood to the patient can be referred to as the venous line 105. In certain embodiments, the arterial line 102 and the venous line 105 connect with one or more veins of the patient. Locomotive power for moving the blood through the extracorporeal flow path 100 is provided by a blood pump 302, which is typically located along the arterial 102 line. Blood is typically conveyed through the extracorporeal flow path 100 at a rate of 50 to 600 mL/min and can be adjusted by a controller to any required rate suitable for a procedure performed by the invention. Blood pump 302 can be a peristaltic pump, although those skilled in the art will readily understand that other types of pumps can be used including diaphragm pumps, centrifugal pumps, and shuttle pumps. In certain embodiments, the blood pump 302 conveys blood through the dialyzer 701 where the blood is contacted with a blood side of a dialysis membrane 702. Blood enters the dialyzer 701 through a blood inlet 504 and exits through a blood outlet 505. The pressure of the blood prior to the blood pump 302 is measured by a pressure sensor 602 and post dialyzer 701 by a pressure sensor 604. The pressure at pressure sensor 602 provides an indication of the adequacy of the blood flow in the arterial line connected to the blood pump 302 inlet and a low or excessively negative pressure relative to atmosphere is an indication of a less adequate access flow that may cause the flow rate produced by blood pump 302 to be unacceptably below the set point flow rate. The pressure indication at pressure sensor 604 can serve to detect obstructions in the venous bloodline and to monitor transmembrane pressure within dialyzer 701. An air trap 707 is placed along the extracorporeal flow path 100 to prevent the introduction of air into the circulatory system of the patient. The air trap 707 is not limited to a particular design. Typical air traps can be drip chambers with an air space that employ a hydrophobic membrane that allows air to pass through the membrane while retaining water-based fluids. Alternatively the air trap 707 can be a chamber that is run full of fluid and which traps any air at a point of greatest elevation and exchanges air via a hydrophobic membrane, such that there is no direct air blood interface. Air-fluid detectors, or bubble detectors 601 and 603 are present to confirm that air is not present in the extracorporeal flow path 100. In some embodiments, air fluid detectors 601 and 603 can be ultrasonic sensors that can detect a change in solution density or scattering due the presence of air or air bubbles.

Valve 402 controls flow into or out of the arterial line 102 of extracorporeal flow path 100. Valve 401 controls flow into or out of the venous line 105 of extracorporeal flow path 100. Valves 401 and 402 may be pinch valves that control flow by non-invasively squeezing the exterior of the extracorporeal flow path to occlude the tubing to prevent flow. Occluding tubing in this manner refers to collapsing the tubing such that the inner lumen of the tubing is closed and flow is prevented from passing through collapsed portion. Other valves, such as diaphragm valves that cause a moving or flexible member to block a flow orifice can also serve this function.

Patient blood access sites are individualized; access types include catheters, grafts and fistulas; and blood access procedures may vary between patients. Any blood access type or method can be used and is non-specific to the present invention. Line 104 indicates the arterial or supply portion of a patient's blood access and could be a fistula needle or catheter. Line 103 indicates the venous, or return portion of the patient's blood access and could be a fistula needle or catheter.

The patient's arterial blood access line 104 is connected to the arterial line 102 of the extracorporeal flow path 100 at connection point 502. A non-limiting example of such a connector is a luer connector. Similarly, the patient's venous blood access line 103 is connected to the venous line 105 of extracorporeal flow path 100 at connection point 501.

Drawing of blood samples and administration of therapeutic substances via the extracorporeal flow path 100 is contemplated by this invention. Any therapeutic substances that can be administered via the blood through extracorporeal flow path 100 such as erythropoietin, iron, and vitamin D may be administered to the patient during dialysis therapy through venous port 503. Further, blood samples may be withdrawn from the extracorporeal flow path 100 at arterial port 525 or venous port 503. A non-limiting partial list of port designs may include capped luer, petcocks, button membranes, and pre-split needle-free wherein one of ordinary skill will understand that port designs in the art may be employed without departing from the scope of the invention.

During the course of conveyance of blood along the extracorporeal flow path 100, heparin or other anticoagulant is added to the blood to prevent clotting of blood within the dialyzer 701 or blood conveyance pathway/extracorporeal flow path 100. Heparin or another anticoagulant is added from an anticoagulant container such as a syringe at a metered rate using an anticoagulant pump 301. The anticoagulant pump 301 can be any pump capable of accurately metering the anticoagulant.

Water reservoir 202 holds a small volume of water that is used to create the solution used for system priming, dialysis therapy, provision of fluid bolus, blood rinse back and system cleaning and disinfection. The water reservoir 202 may be filled with potable tap water by the user. Alternatively, the water reservoir 202 may be filled with bottled drinking water if potable water or other suitable types of water are not available. Purified water may also be used. Further, water reservoir 202 may be the container of bottled drinking water itself. Other types of water suitable for use in dialysis systems including hemofiltration, hemodiafiltration and peritoneal dialysis are contemplated by the present invention. One of ordinary skill in the art will recognize that it is possible to bypass water reservoir 202 and connect a potable water source directly to port 510S as shown in FIG. 5C.

Degassing and De-Aeration of Water Supply

The water source used to supply water reservoir 202 may have significant amounts of dissolved gasses that could be released from solution inside the controlled compliant flow path 110 to create air pockets that degrade performance of the system. Dissolved gasses may include the gaseous constituents of air such as nitrogen, oxygen and carbon dioxide. As detailed in FIG. 1C, the invention has a water degassing, or de-aeration circuit that can optionally be employed to remove dissolved gasses from the water in reservoir 202 prior to mixing solution and priming the fluid circuits. The arrows in FIG. 1C depict the direction of flow during the de-aeration process. During de-aeration, fluid intake bypass valve 404 is positioned to allow pump 305 to withdraw fluid from water reservoir 202 through intake line 113 and flow restriction 408 and heater 708. De-aeration of the water can be accomplished without having heater 708 located in the de-aeration flow path and therefore heater 708 and heating of the fluid can be considered optional to de-aeration. Pump 304 is a positive displacement pump that is not operated during this phase of operation and no flow passes through pump 304. De-aeration bypass valve 405 is positioned or set to direct flow from the outlet of dialysate pump 305 through de-aeration bypass conduit 112 to line 114 and back into water reservoir 202. Flow restriction 408 is sized such that when the dialysate pump 305 is operated at a predetermined rate, the pressure of fluid flowing through the restriction 408 drops to a low absolute pressure causing dissolved air to be released from solution and form gas bubbles. Non-limiting examples of flow restrictions are orifices, venturis, or narrow tubes. Heater 708 can optionally be operated to increase the temperature of the fluid which further reduces the solubility of air in water, enhancing the de-aeration process. As the fluid is recirculated in the de-aeration loop shown in FIG. 1C, air bubbles are released from solution and returned to water reservoir 202 through lines 112 and 114, where they rise to the surface of the fluid in water reservoir 202 and are exhausted from water reservoir 202 through vent opening 512. The de-aeration process recirculates the water for a predetermined time sufficient to de-aerate the water and, optionally, until no more bubbles are detected in the water flowing past bubble detector 608.

Referring again to FIG. 1, dialysate within the system is conveyed through one of a first recirculating dialysate pathway or controlled compliant flow path 110 which carries dialysate from outlet port 507 of dialyzer 701 in a complete loop back to inlet port 506 of dialyzer 701, or a bypass flow path 111, which serves to bypass the dialyzer 701 during certain system functions. The controlled compliant flow path 110 can contain dialysate in certain embodiments, and be referred to as a solution conduit flow path. Bypass flow path 111 may be referred to as a priming or recirculation bypass in certain embodiments as described further herein. The controlled compliant flow path 110 and bypass flow path 111 have one or more conduits for conveying the dialysate. Flow is controlled to go through the controlled compliant flow path 110 or bypass flow path 111 by means of bypass valve 407. It is understood by one skilled in the art that three-way valve 407 can be replaced by two-way valves with the same result to control the flow through the dialyzer 701 or bypass flow path 111.

Dialysate that is conveyed through the dialyzer 701 on the dialysate side of the dialysis membrane 702 picks up waste products from the blood, including urea, by diffusion, ultrafiltration, hemofiltration or hemodiafiltration. Dialysate enters the dialyzer at a dialysate inlet end 506 and exits at an outlet end 507. The dialysate exiting the dialyzer 701 passes through a blood leak detector 605 that can determine the presence of blood in the dialysate indicating a breach in the dialysis membrane 702.

Valve 403 passes flow in only one direction such that fluid may not enter the dialyzer 701 through the outlet port 507, but may only enter the dialyzer through inlet port 506, having first flowed through microbial filter 706. In other embodiments, the valve 403 may be a 2-way valve under active control, or a 3-way valve under active control allowing fluid back to the dialyzer 701 and positioned at junction 526. Microbial filter 706 removes residual bacteria and endotoxin from the dialysate, such that dialyzer membrane 702 becomes a redundant microbial barrier between the dialysate and the blood. In other embodiments, the microbial filter 706 can be placed in any portion of a flow path (not shown) to minimize system contamination. Suitable microbial filters include commercially available hollow fiber ultrafilters having a membrane pore size sufficiently small to exclude passage of both microbes and endotoxins and other such suitable filters known to those of ordinary skill in the art.

The dialysate is conveyed through heater 708 to heat the dialysate to the prescribed dialysate temperature. Dialysate pump 305 provides the pumping action to cause the dialysate to flow through the controlled compliant flow path 110, which can re-circulate dialysate. Flow rate sensor 609 measures dialysate flow rate for closed loop control of dialysate pump 305 and/or measurement of dialysate flow rate to enable control of infusate metering at a controlled ratio to the dialysate flow. In certain embodiments dialysate pump 305 can be a positive displacement metering pump and flow rate sensor 609 can be an optional sensor. Pressure sensor 610 measures pressure of the dialysate before inlet port 513 of sorbent cartridge 703. The sorbent cartridge can be a disposable cartridge assembly that is disposed after use, a system of individual material containers, or a re-usable container that has contents that can be opened and the contents replaced as needed.

Sorbent cartridge 703 removes waste products from the dialysate before the dialysate is re-conveyed through the dialyzer 701. The dialysate enters the sorbent cartridge 703 at a dialysate inlet end 513 and exits at an outlet end 514.

In one non-limiting embodiment a static mixer 704 serves to ensure that concentrates added to the dialysate are thoroughly mixed before solution characteristics such as conductivity are measured. In any embodiment, if sufficient mixing of infusate and dialysate is obtained without employing a static mixer, then the static mixer 704 may be considered to be optional in that embodiment.

Degassing and De-Aeration During Priming

Figure 16:
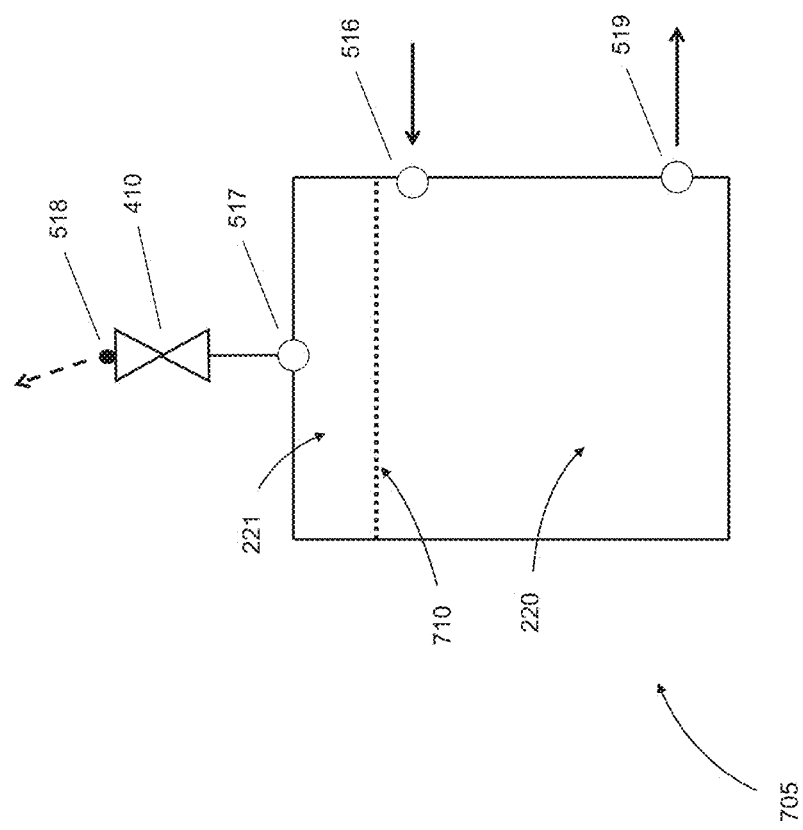
FIG. 16 shows a schematic of a degassing module in certain embodiments.

In certain embodiments, a degassing module 705 removes air during system priming as well as gasses, such as carbon dioxide, introduced into the dialysate by the sorbent cartridge 703. Referring to FIG. 16, a schematic of a degassing module 705 is shown having an upper port 516 that is a fluid inlet port, a lower port 519 that is a fluid outlet port, a hydrophobic vent membrane 710 separating a flow through chamber 220, and a space that is referred to as a gas collection chamber 221. Gas collection chamber 221 has a vent port 517 in communication with gas outlet port 518, which is in communication with the atmosphere. Vent control valve 410 can be operated to selectively permit gas to flow between gas collection chamber 221 and the atmosphere, and, when vent control valve 410 is open, the pressure in gas collection chamber 221 is equal to atmospheric pressure. When vent control valve 410 is open, direction of gas flow depends upon the relative pressure difference between chambers 220 and atmosphere. If valve 410 is open and chamber 220 has a pressure greater than atmospheric, any gas in chamber 220 that has risen to contact hydrophobic vent membrane 710 will be forced through hydrophobic vent membrane 710 and will be passed through gas collection chamber 221 and flow out to atmosphere through gas outlet port 518. Conversely, if valve 410 is open and flow through chamber 220 has a pressure less than atmospheric, air in contact with vent membrane 710 will be forced through hydrophobic vent membrane 710 and will enter flow through chamber 220. During normal operation, the degassing module can be operated with a fluid pressure in flow through chamber 220 that is greater than atmospheric to ensure that gas that has risen to contact hydrophobic vent membrane 710 will be exhausted from flow through chamber 220. Degassing module 705 can be located in the controlled compliant flow path 110 between pump 305 and dialyzer inlet port 506 as shown in embodiments depicted in FIGS. 1 and 1E, and between pump 305 and replacement fluid port 538 on the venous line 105 of extracorporeal circuit 100, as shown the embodiment depicted in FIG. 1D. Other positions are possible in the present invention suitable for the intended purposes of degassing the system. The system can be normally operated with fluid pressures at ports 506 and 538 that are greater than atmosphere and therefore the pressure inside degassing module 705 flow through chamber 220 will be greater than atmospheric also, thus causing any gas contacting hydrophobic vent membrane 710 to pass through hydrophobic vent membrane 710 to atmosphere. Fluid pressure at pressure sensor 606 in the case of the embodiments depicted in FIGS. 1 and 1E, or fluid pressure at pressure sensor 604 in the embodiment depicted in FIG. 1D can be monitored and, if the pressure drops to less than a predetermined amount greater than atmospheric, for example less than 25 mm mercury above atmospheric, vent control valve 410 can be closed to prevent air ingress to degassing module 705. In certain embodiments, a flow restriction 409 is present in bypass flow path 111, as needed, to ensure that sufficient back pressure remains in the main controlled compliant flow path 110 to maintain adequate pressure inside the degassing module 705 flow through chamber 220 relative to atmospheric pressure during operations where the dialysate flow is switched to bypass the dialyzer 701 through bypass flow path 111. Flow restriction 409 may be an orifice, a venture, tubing with sufficiently small inside diameter to create the necessary restriction, an actuated restrictor, such as a pinch valve that compresses the tubing to constrict the flow passing through bypass flow path 111, or any suitable element that sufficiently restricts the fluid flow to maintain the desired fluid pressure upstream of the restriction.

The dialysate flow inlet 516 in FIG. 16 is placed at a higher elevation than the dialysate outlet 519 so that the dialysate or fluid in the system flows in a downward direction through the module. It is a known phenomenon that gas bubbles rise rates in aqueous solutions increase as the diameter of the gas bubble increases wherein gas bubble rising rates are known in the published literature. This principle can be applied to separate the gas bubbles from the liquid to ensure that the bubbles do not pass out of flow through chamber 220 through fluid outlet port 519. The maximum fluid flow rate that will pass through the degassing module 705 flow through chamber 220 can be determined wherein the cross sectional area of the chamber is selected such that the downward flow velocity of the dialysate is less than the upward rise velocity of the smallest bubble that the module is intended to capture.

In one embodiment, the degassing module has a flow-through chamber 220 having a hydrophobic vent membrane 710 forming an upper portion of the flow chamber 220. The minimum elevation requirement for the location of the vent membrane is that it has an elevation greater than the fluid outlet port 519. The hydrophobic vent membrane 710 has a sufficient permeability and the surface area of hydrophobic vent membrane that is exposed to both chamber 220 and chamber 221 is sufficiently large to enable a flow of gas that is rising to the top of flow through chamber 220 to contact hydrophobic vent membrane 710 will be caused to flow through hydrophobic vent membrane 710 to gas collection chamber 221 by the pressure differential between the fluid in flow through chamber 220 and the atmosphere. The hydrophobic vent membrane 710 is further required to have a sufficient water break through pressure, for example greater than 2 bar, so that liquid water does not pass from flow through chamber 220 through hydrophobic vent membrane 710 to gas collection chamber 221. Persons of skill in the art will be able to determine the range of operating pressures for flow through chamber 220 and a desired rate of gas removal from flow through chamber 220 to determine a combination of membrane permeability and exposed membrane surface area that is required for a particular application. An example of a commercially available membrane that can be suitable for a degassing module is Pall Corporation 0.2 micron pore size Emflon® part number PTFE020LF0A.

Vent control valve 410 is opened to permit gas flow to atmosphere when the degassing module 705 is being operated to remove gas from the dialysate. Vent control valve 410 is closed to prevent air entry into the controlled compliant flow path through the hydrophobic vent membrane during certain operating functions of the system that may cause the dialysate pressure in the degassing module 705 to drop below atmospheric and undesirably pull air into the system. Vent control valve 410 is opened during other system functions where the dialysate pressure within degassing module 705 is below atmospheric pressure and it is desirable to allow air to enter the controlled compliant flow path through the hydrophobic vent membrane at gas outlet port 518, for example when fluid is being drained from the controlled compliant flow path.

Figure 17:
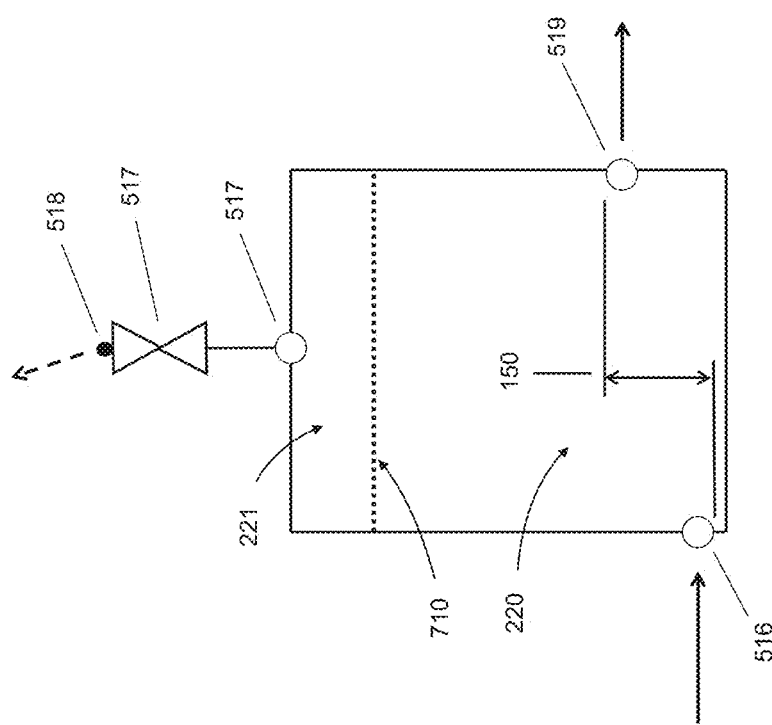
FIG. 17 shows another schematic of a degassing module in certain embodiments having fluid inlet and outlet ports at different elevations.

In FIG. 17, an embodiment of a degassing module 705 is shown that has fluid inlet port 516 at a lower elevation in flow through chamber 220 than fluid outlet port 519. The present design can be used if a flow cross section of the flow through chamber 220 is sufficiently large that, at a maximum fluid flow rate for the degassing module, a fluid transit time from fluid inlet port 516 to fluid outlet port 519 is sufficiently long so that the smallest bubble that the degassing module is intended to capture will rise at least by the amount of an elevation difference 150 and will rise above the elevation of fluid outlet port 519 during the elapsed fluid transit time from fluid inlet port 516 to fluid outlet port 519.

Figure 18:
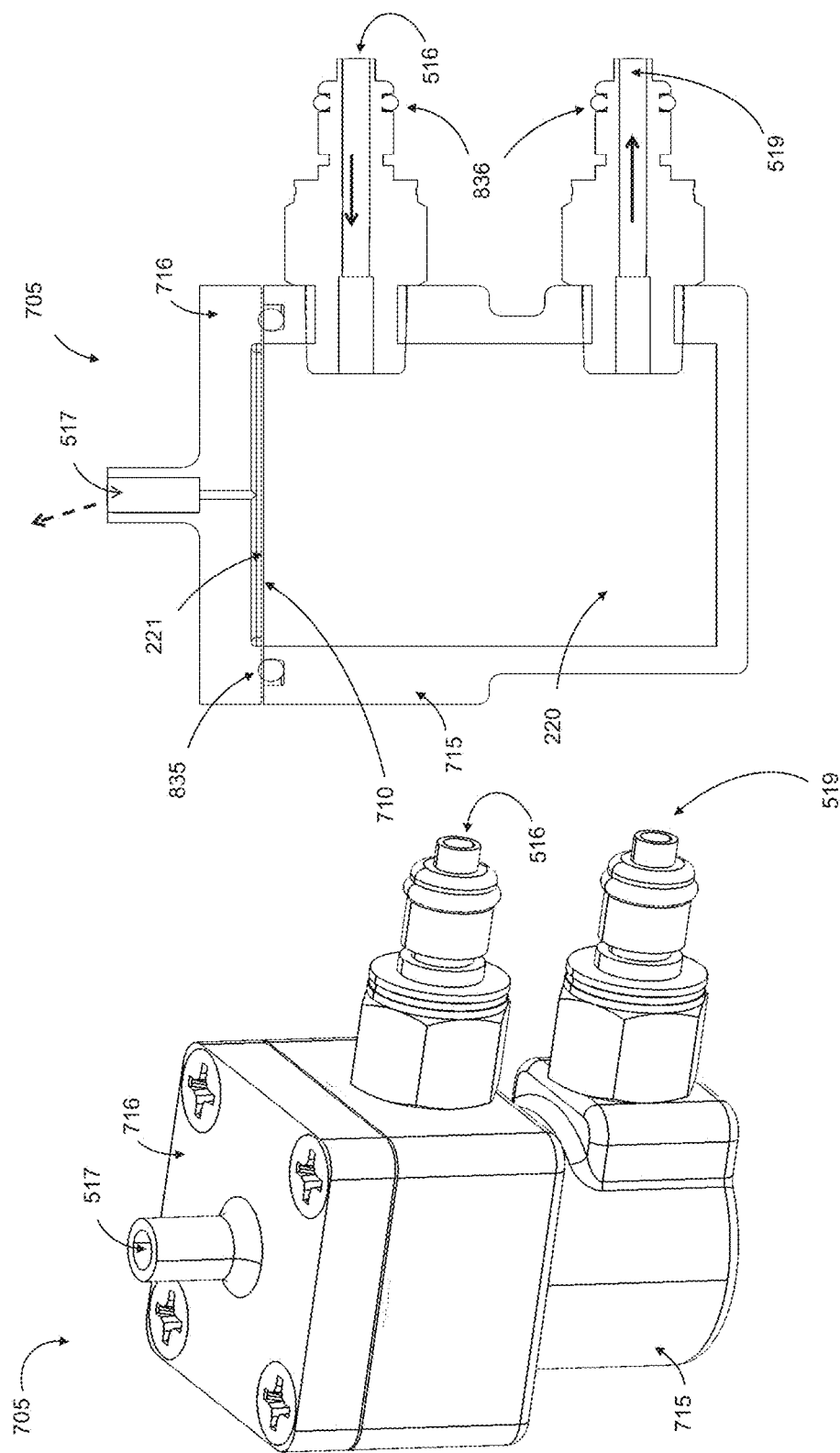
FIG. 18 shows an isometric view of the exterior of a degassing module.

FIG. 18 shows images from an embodiment of degassing module 705. The left hand view is an isometric view of the exterior of the degassing module. The right hand view is a section through a plane that passes through the axis of fluid inlet port 516 and the axis of fluid outlet port 519. The embodiment has a body 715 that houses the flow through chamber 220. The hydrophobic vent membrane 710 is shown in contact with the cover 716. The surface of cover 716 that contacts hydrophobic vent membrane 710 has a plurality of intersecting grooves that form gas collection chamber 221 and allow the gas to flow to vent port 517. Also shown is an o-ring seal 835 that serves to prevent fluid leakage from the seam between body 715 and cover 716. The methods of seal and attachment are exemplary and non-limiting, as those of skill in the art will recognize that there are many methods to attach cover 716 to body 715 and form a leak tight seal, for example adhesive bonding, ultrasonic bonding and overmolding. The shown o-ring seals 836 can provide fluid seals between fluid ports 516 and 519 and their mating ports of the base module. Again, the seal 836 and geometry of ports 516 and 519 are exemplary and non-limiting, as those of skill in the art will recognize that there are many suitable seals, for example Q-rings, double seals, lip seals and face seals, and many fluid port geometries, for example luer connectors, Hansen connectors, and push to connect tube fittings.

Other types of degassing modules may be employed, such as parallel or wound hollow fiber assemblies. With these devices, a vacuum may be applied to the gas side of the module to draw dissolved gas from solution in addition to removing gas bubbles. Non-limiting examples of dissolved gasses include nitrogen, oxygen and carbon dioxide. If the gas being removed is carbon dioxide, the pH of the dialysate can be increased without adding buffer, or by addition of less buffer.

Another type of degassing module that can be employed has a float that causes a seal to be pressed against an escape orifice when the chamber is full, or nearly full of liquid. When the chamber has trapped a quantity of gas sufficient to cause the liquid level to drop so that the float no longer presses the seal onto the orifice, gas is allowed to escape from the chamber. Microbial contamination of the fluid can be prevented by placing a microbial vent filter over the chamber outlet opening to atmosphere.

In one non-limiting embodiment, the dialysate can flow through or across the ammonia sensor 611 that detects a potentially hazardous condition where the ammonia byproduct of urea breakdown escapes from sorbent column 703. The ammonia sensor may use optical methods to detect a color change of ammonia and/or ammonium sensitive media contained within sensor 611. If ammonia and/or ammonium are detected, control action switches bypass valve 407 to direct dialysate flow to bypass flow path 111 and prevent out of tolerance dialysate from passing through the dialyzer 701. Further, one-way valve 403 prevents the ammonia and/or ammonium bearing dialysate from backing up into the dialyzer 701. As such, the dialysate can be circulated through the sorbent cartridge 703 while bypassing the dialyzer 701 and preventing contact with the patient's blood when required.

Temperature sensor 612 measures the temperature of the dialysate to verify that it is within the predetermined temperature limits before passing through dialyzer 701. If the temperature is out of tolerance, control action switches bypass valve 407 to direct dialysate flow to bypass flow path 111 and prevent out of tolerance dialysate from passing through the dialyzer 701 and further recirculated until the dialysate temperature is within acceptable limits. Temperature sensor 612 may also be used for closed loop control of dialysate temperature by action of the controller and heater. Refreshed dialysate exiting an outlet end of the sorbent cartridge 703 can be monitored by a conductivity sensor 613. The design of any conductivity sensor employed in embodiments described herein is not particularly limited; however, a typical conductivity sensor has two electrodes where a current between the two electrodes is monitored. The presence of sodium ions in the dialysate is the major contributor to the conductivity measured by conductivity sensor 613. Conductivity is continually monitored and reported to the controller to assess the quality and safety of the dialysate. When the conductivity of the dialysate falls within a predetermined range, the dialysate is directed by valve 407 to a dialysate inlet end 506 of the dialyzer 701; the valve 407 is located between an outlet end 514 of the sorbent cartridge 703 and the dialysate inlet end 506 of the dialyzer 701. In certain embodiments, the valve 407 is a three-way valve. The control action of valve 407 can also be accomplished by a pair of 2-way valves.

When the conductivity measured by conductivity sensor 613 is outside of the predetermined range, the valve 407 can direct the dialysate to be conveyed through the bypass flow path 111 and bypass the dialyzer 701. Further, one-way valve 403 prevents the dialysate from backing up into the dialyzer 701. As such, the dialysate can be circulated through the sorbent cartridge 703 while bypassing the dialyzer 701 and preventing contact with the patient's blood until the sodium has been adjusted by control action of the system. The system reduces sodium concentration within the controlled volume dialysate circuit by simultaneously operating water pump 304 to add water from water reservoir 202 while simultaneously operating fluid balance control pump 303 to remove an equal volume of dialysate by pumping it to solutions reservoir 201. If conductivity is low, the system can increase sodium concentration by switching salination valve 406 to direct flow through a sodium conduit flow path in fluid communication with sodium chloride cartridge 203 and pump saturated sodium solution into the dialysate by pumping and metering action of salination pump 307.

The dialysate is filtered through a microbial filter 706 before passing into dialyzer 701 through inlet 506. Sorbent cartridge 703 performs a high degree of bacterial and endotoxin removal from the solution and the microbial filter 706 further removes residual bacteria and endotoxin such that the resulting solution is capable of meeting the microbial purity standard for ultrapure dialysate and dialyzer membrane 702 becomes a redundant barrier to passage of bacteria from the dialysate compartment to the blood compartment by solution that is transferred across dialysis membrane 702.

Typically, the output of the sorbent cartridge in prior art sorbent systems meets the Association for the Advancement of Medical Instrumentation's (AAMI) Water for Hemodialysis standard but does not meet the AAMI standard for microbiologically ultrapure dialysate. It has been shown in the medical literature that ultrapure dialysate is desirable in reducing the inflammatory response in the ESRD patient. Desirable quality for ultrapure dialysate is less than about 0.1 colony forming unit (cfu)/mL where cfu is the number of viable cells per unit volume, and detectable endotoxins less than about 0.03 endotoxin unit (EU/mL). Suitable filters include ultrafilters and micro filters manufactured or supplied by Medica, however any known by those of ordinary skill for the intended purpose can be used.

The pressure of the dialysate entering the dialysate inlet end of the dialyzer 701 can be measured by a pressure sensor 606.

The components forming the controlled compliant flow path 110 can have a controlled compliant volume wherein the controlled compliant flow path 110 further incorporates a control pump such as fluid balance control pump 303 that can be operated bi-directionally to cause the net movement of fluid from an extracorporeal side of the dialyzer 701 into the controlled compliant flow path 110 or to cause net movement of fluid from the controlled compliant flow path 110 into the extracorporeal side of the dialyzer 701. In particular, the control pump 303 or any such similar pump can be operated in the efflux direction to cause the movement of fluid from the extracorporeal side of the dialyzer 701 into the controlled compliant flow path 110 and in the influx direction to cause the movement of fluid from the controlled compliant flow path 110 into the extracorporeal side of the dialyzer 701. In this manner, the net volume of fluid crossing the dialysate membrane 702 between the dialysate compartment and the blood compartment can be under direct control and can be accurately determined.

In certain embodiments, operation of the control pump 303 in the influx direction to drive liquid into the controlled compliant flow path 110 and subsequently cause movement of fluid from the controlled compliant flow path 110 to the extracorporeal side of the dialyzer 701. The control pump 303 can also be used for the movement of fluid in the opposite direction across the dialyzer 701 into the controlled compliant flow path 110. It is noted that the solution reservoir 201 or any other suitable reservoir attached to the controlled compliant flow path 110 can allow the system to adjust the patient fluid volume by withdrawing fluid and storing the desired amount in the respective reservoir and/or by providing rebalanced fluids to the patient and removing waste products. For example, the fluid stored in a solution reservoir 201 attached to the controlled compliant flow path can be used to store a volume of fluid equal to the ultrafiltrate volume removed from the patient during ultrafiltration (UF). Alternatively, the fluid stored in any fluid reservoir attached to the controlled compliant flow path 110 can contain a desired infusate. In certain embodiments, the delivered fluid can contain a therapeutic component deliverable across the dialyzer 701 and into the patient's bloodstream. Additionally, the volume of the controlled compliant flow path 110 can be actively controlled by the user or a programmed controller.

In certain embodiments, the control pump 303 can allow for fluid to move from the controlled compliant flow path 110 to the extracorporeal side without creating a vacuum, wherein the operation of the control pump 303 is controlled as described herein. Likewise, the control pump 303 can allow for fluid to move from the extracorporeal side, and hence the patient's body via the action of the pumps. The net movement of fluid between the extracorporeal side of the dialyzer 701 and the controlled compliant flow path 110 can be accurately controlled and metered using the removed fluid in certain embodiments. In other embodiments, the removed fluid can be transferred back to the patient through controlled compliant flow path 110 using the solution stored in solution reservoir 201. In some embodiments, the solution reservoir 201 can be prefilled with water, dialysate or other fluid for addition to the controlled compliant flow path 110.

As such, embodiments of the invention can have a controlled compliance controlled compliant flow path 110 that is accurately controlled to precisely remove or add fluid to the extracorporeal side of the dialyzer 701. Due to the substantially inflexible void volume of the components and connecting conduits of the controlled compliant flow path 110, net movement of fluid or water is prevented from moving in either direction across the membrane 702 between the extracorporeal flow path 100 of the dialyzer 701 and the controlled compliant flow path 110 of the dialyzer 701. Specifically, due to the controlled compliance feature of the void volume of the controlled compliant flow path 110, water cannot passively move in either direction between the extracorporeal side and the dialysate side through the dialysis membrane 702. In the event of factors that tend to increase pressure on the extracorporeal side of the dialysis membrane, such as increased blood flow rate or blood viscosity, pressure across the membrane will automatically be equalized due to the limited volume of the controlled compliant flow path 110 and the non-compressible nature of the dialysate. In the event of factors that tend to increase pressure on the dialysate side of the dialysis membrane 702, such as increased dialysate flow rate, net movement of water from the controlled compliant flow path 110 to the extracorporeal flow path 100 is prevented by a vacuum that would form in the controlled compliant flow path 110 in the event of such a movement. This capability can further be used to enhance the convective clearance of the system for uremic impurities while controlling the net fluid removed from the patient, for example, creating periods of fluid movement across the membrane with occasional reversal of direction. In certain embodiments, an ultrafiltrate can be used as described herein. However, the present invention is not limited to a controlled compliance flow path wherein the controlled compliant flow path 110 in certain embodiments is not a controlled compliance flow path and may include one or more open reservoirs for storing or accumulating dialysate.

Since the dialyzer can be a high-flux type there is some fluid flux back and forth across the dialyzer membrane due to the pressure differential on the blood and dialysate sides of the membrane. This is a localized phenomenon due to the low pressure required to move solution across the membrane and is called back-filtration, however results in no net fluid gain or loss by the patient.

The fixed volume controlled compliant flow path, as described, enables the fluid balance control pump 303 to be operated in concert with the water pump 304 and acid concentrate pump 306 such that net fluid removal or subtraction from the controlled compliant flow path 110, and thus the extracorporeal flow path 100 can be precisely determined and controlled according to a simple volumetric control algorithm that is expressed by as sum of the volumes in following formula.

Patient Fluid Balance+Fluid Balance Control Pump+
Water Pump+Acid Conc. Pump+$\Sigma_{i=0}^{n} X_i = 0$ The term "Patient Fluid Balance" refers to the volume of fluid added to or removed from the patient by net movement of fluid across the dialyzer membrane 702. The algebraic sign of each term of the above formula is determined by whether the flow is efflux or influx to the controlled compliant flow path 110. The term X refers to the volumetric flow rate of a pump where the number of pumps can range for n from 0 to 20. The term "n from 0 to 20" means any integer value of 0, 1, 2, 3, 4, 5, 6, 7, 8, 9, 10, 11, 12, 13, 14, 15, 16, 17, 18, 19, or 20. The formula applies to an instantaneous rate of fluid removal. The instantaneous net fluid removal rate can also be integrated over the time course of therapy to determine the net fluid removal during the elapsed therapy time. Thus, the system can operate the aforementioned pumps to selectively meter in and meter out fluid from the flow loop to accomplish a predetermined patient fluid balance at any time throughout the course of a therapy delivery session.

In certain embodiments, any one of the control pumps of the invention can be a peristaltic pump, a volumetric metering pump, diaphragm pump, or a syringe style pump. Hence, the controlled compliant flow path 110 has a substantially inflexible volume that can deliver controlled changes in volume modulated by the control pump 303 and optionally any other pump(s) that add or remove fluid to and from the controlled compliant flow path 110. The contents of U.S. patent application Ser. No. 13/565,733 filed on Aug. 2, 2012 are incorporated herein by references in their totality.

In certain embodiments, the controlled compliant flow path 110 can have a total void volume from about 0.15 L to about 0.5 L. In other embodiments, the controlled compliant flow path 110 can have a void volume from about 0.2 L to about 0.4 L or from 0.2 L to about 0.35 L. Other volumes can be envisioned by those of ordinary skill in the art depending on parameters such as patient weight, size, and health condition. The system can be designed to be a portable system, a desktop system or a large system suitable for heavy use in a clinical setting. Hence, both large volumes greater than 0.5 L to about 5 L, and micro-volumes from as small as 0.1 L to about 0.5 L such as 0.1 L to 0.2 L, 0.1 L to 0.3 L, 0.1 L to 0.4 L, 0.2 L to 0.3 L, 0.3 L to 0.4 L, or 0.3 L, 0.5 L, or greater volumes of about 1 L, 2 L, 3 L, 4 L, or 5 L are contemplated by the invention.

Infusates such as sodium chloride and sodium bicarbonate which have aqueous solubility limits greater than their concentration in dialysate can be produced on line by reconstituting a saturated solution from a container having a mass of solute greater than the amount of solute required for a therapy session, such that a reserve of solute persists and the solution in the container remains saturated. Although solubility does vary with temperature, the circulating dialysate temperature is controlled by heater 708 and the temperate of the solution exiting the containers may be optionally measured by temperature sensor 614 located near the outlet of the containers such that actual concentration of infusate can be determined from empirical temperature-solubility curves.

Salination valve 406 directs the saturated solution flow path through either sodium chloride cartridge 203 having an excess of the solute sodium chloride, or through a buffer conduit flow path in fluid communication with sodium bicarbonate cartridge 204 having an excess of the solute sodium bicarbonate. The excess amount of solute can be an amount of solute greater than a predetermined amount of the solute that may be consumed during the course of normal operation of the system, such that some undissolved solute remains in the cartridge or container. The excess undissolved solute can result in solution exiting the cartridge or container that can be maintained in an essentially saturated state by virtue of the excess solute that remains available to dissolve into solution. It is readily apparent to one skilled in the art that the function of 3-way valve 406 could be replaced by two 2-way valves to accomplish the same fluid circuit functionality. Other valve arrangements whether 2-way, 3-way or more having different configurations to achieve the same effect is contemplated by the present invention.

Figure 19:
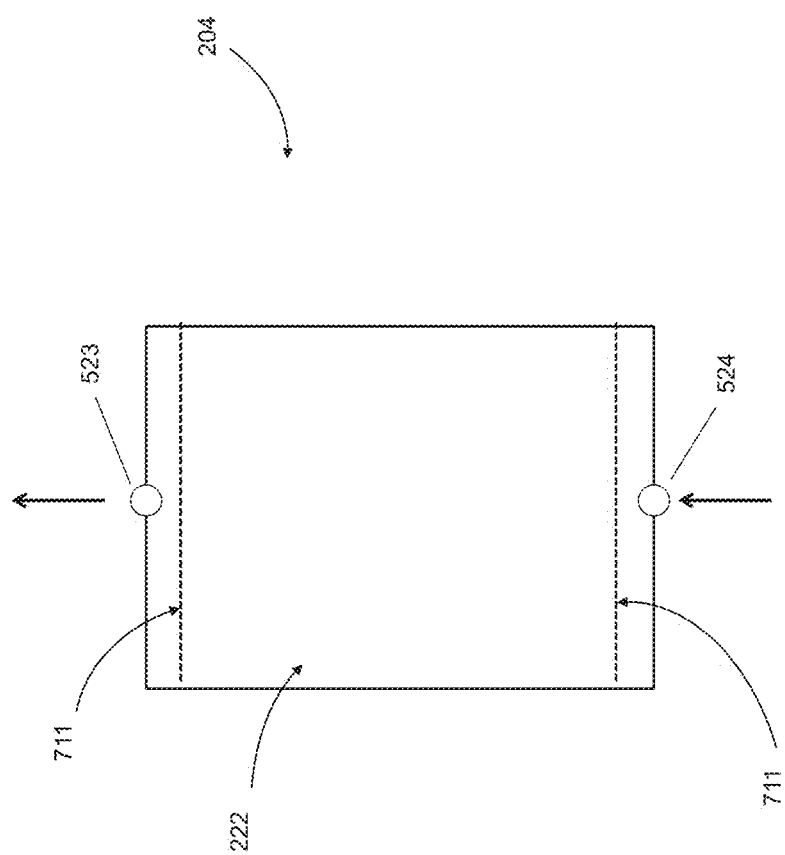
FIG. 19 shows a fluid flow through a bicarbonate cartridge in accordance with certain embodiments.

In a preferred embodiment, sodium chloride cartridge 203 and bicarbonate cartridge 204 are supplied in dry form and then hydrated to produce a saturated aqueous solution during the water intake and priming steps of system operation. This eliminates microbial growth that is possible with bicarbonate that is supplied as an aqueous solution and also reduces the transportation weight of the supplies. In FIG. 19, a fluid flow through bicarbonate cartridge 204 can reconstitute a saturated aqueous solution from a dry sodium bicarbonate as shown. Fluid can enter through port 524, pass through a first proximal layer of filter material 711, through flow through chamber 222, then pass through a second distal layer of filter material 711, and then out through fluid outlet port 523. The function of the filter material 711 can be to retain the sodium bicarbonate inside chamber 222 during storage and transport and also to prevent undissolved sodium bicarbonate particles from passing out of chamber 222 when fluid is flowing through chamber 222. Blown or spun depth filter media are preferred for filter material 711. An amount of dry sodium bicarbonate that is greater than the amount that will be consumed during operation of the system is contained in flow through chamber 222. The fluid flowing through chamber 222 can dissolve the sodium bicarbonate until a saturated solution is produced. The fluid passing out of bicarbonate cartridge 204 at fluid outlet port 523 can remain saturated as long as an amount of undissolved sodium bicarbonate remains in flow through chamber 222. Saturation concentration of sodium bicarbonate is well known, including its variation with temperature. Temperature sensor 614 can measure the temperature of the solution exiting through fluid outlet port 523 to enable a controller to determine the sodium bicarbonate concentration of the fluid exiting the bicarbonate cartridge 204. It should be further noted that the solution that is metered from flow path 100 through the bicarbonate cartridge 204 by action of pump 307 can contain other solutes, principally sodium and chloride, that these solutes affect the saturation concentration of bicarbonate in bicarbonate cartridge 204, and the effect of these solutes, whose concentrations are also controlled by the system, can be taken into account when determining the bicarbonate concentration in the saturated bicarbonate cartridge 204. The rate of salination pump 307 can be adjusted accordingly by a controller to maintain the desired rate of sodium bicarbonate infusion from conditioning conduit flow path 115 to the controlled compliant flow path 110 and filtrate regeneration circuit 120.

Figure 20:
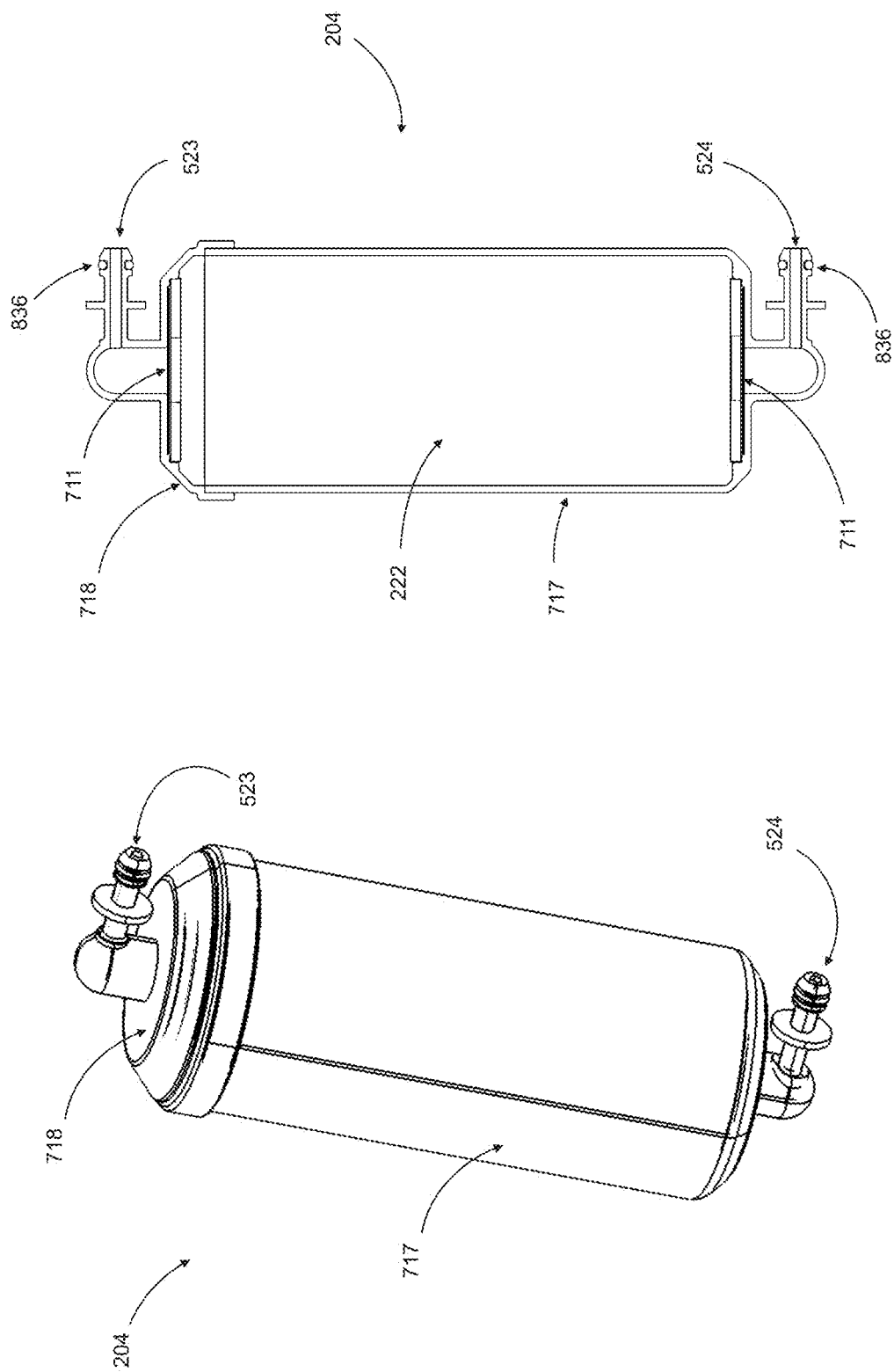
FIG. 20 shows two views of a bicarbonate cartridge in certain embodiments.

In FIG. 20 an embodiment of a bicarbonate cartridge 204 is shown. Fluid can enter through fluid inlet port 524, and can pass through a first proximal filter layer 711, then through flow through chamber 222 containing an amount of sodium bicarbonate in excess of the amount that will be consumed by operation of the system, through a second distal filter layer 711, and then exits through fluid outlet port 523. The enclosure of the bicarbonate cartridge is formed by base 717 and cover 718. In the embodiment shown, there can be a lap joint positioned between base 717 and cover 718. The lap joint configuration is a non-limiting example of an embodiment of the invention wherein those of skill in the art will recognize that many suitable methods of attachment and sealing of the cover 718 to body 717, for example adhesive bonding, snaps with elastomeric seals, threads, spin welding, ultrasonic welding and press fitting are available. Also shown are o-ring seals 836 that provide fluid seals between fluid ports 524 and 523 and their mating ports of the base module. The seals 835 and the geometry of ports 524 and 523 are exemplary and non-limiting, as those of skill in the art will recognize that there are many suitable seals, for example Q-rings, double seals, lip seals and face seals, and many fluid port geometries, for example luer connectors, Hansen connectors, and push to connect tube fittings, any of which can be used in the present invention.

As shown in FIG. 1, the dialysate is recirculated through the controlled compliant flow path 110 by a dialysate pump 305. When the fluid balance control pump 303, water pump 304, salination pump 307, and acid concentrate pump 306 are not operating, fluid along the length of the controlled compliant flow path 110 flows into and out of the dialyzer 701 at a rate determined solely by the action of the dialysate pump 305. In some embodiments, the dialysate pump can be operated at a rate from about 50 to about 800 mL/min. The dialysate pump 305 can be a positive displacement pump such as a reciprocating metering pump, a diaphragm pump, or peristaltic roller pump. The dialysate pump 305 selection is not limited to positive displacement pumps and may be a gear pump, vane pump, or centrifugal pump. In one embodiment, a gear pump can be used in the controlled compliant flow path 110. In the extracorporeal path 100, a peristaltic pump can be used. However, it will be understood that many other types of pumps known to those of skill in the art can be used.

In preferred embodiments, fluid balance control pump 303 can operate bi-directionally to meter fluid between solution reservoir 201 and the controlled compliant flow path 110 and the fluid balance control pump 303 is a positive displacement pump. Non-limiting examples of positive displacement pumps include fixed volume, reciprocating piston pumps, diaphragm pumps or peristaltic roller pumps.

Water pump 304 is normally operated in an influx direction to meter water from water reservoir 202 into the controlled compliant flow path 110. Water pump 304 is a positive displacement pump. Non-limiting examples of positive displacement pumps include fixed volume, reciprocating piston pumps, diaphragm pumps or peristaltic roller pumps.

Salination pump 307 is operated to meter fluid from the controlled compliant flow path 110 through cartridges within a conditioning flow path 115 containing an amount of solute greater than the aqueous solubility of the solute such that saturated solutions of an infusate such as sodium chloride or sodium bicarbonate are metered back into the controlled compliant flow path 110 to enable the concentration of one or more solutes in the dialysate to be increased in the dialysate. Salination pump 307 is a positive displacement pump. Non-limiting examples of positive displacement pumps include fixed volume, reciprocating piston pumps, diaphragm pumps or peristaltic roller pumps.

In FIG. 1, the salination pump 307 can pull dialysate after the outlet of the sorbent cartridge 703 and returns the fluid to the controlled compliant flow path 110 at a point upstream of the dialysate pump inlet. The configuration shown in FIG. 1 is one non-limiting example where one of ordinary skill can envision other points on the controlled compliant flow path 110 for returning fluid either pre, or post sorbent cartridge 703. Specifically, and with reference to FIG. 1, the function of salination pump 307 is to meter a controlled volume of fluid from the controlled compliant flow path 110 through a conditioning flow path 115 containing a saturated solution cartridge and return to the controlled compliant flow path 110 an equal volume of saturated solution. The fluid can be returned to the controlled compliant flow path 110 at a range of points between bypass junction 526 and conductivity sensor 613. Referencing FIG. 1C, it is further noted that the salination pump 307 can intake fluid at a range of points from bypass junction 526 and conductivity sensor 613, with the preference that the inlet to pump 307 is located at a point on the controlled compliant flow path 110 that is not immediately downstream from the outflow of concentrated solution passing from valve 406 back to the controlled compliant flow path 110.

Electrolyte concentrate, or acid concentrate pump 306 is normally operated in an influx direction to meter a concentrate containing electrolytes such as $K^+$, $Mg^{++}$, $Ca^{++}$ and other substances constituting the dialysate prescription from the acid concentrate reservoir 205. Acid concentrate pump 306 is a positive displacement pump. Non-limiting examples of positive displacement pumps include fixed volume, reciprocating piston pumps, diaphragm pumps or peristaltic roller pumps.

Due to the substantially inflexible void volume of the circuit components and connecting conduits that constitute the controlled compliant flow path 110, the net movement of fluid over any time interval across the dialysis membrane 702 can be accurately controlled by precisely removing or adding fluid volume to the controlled compliant flow path by coordinated action of one or more of the pumps 303, 304 and 306. Thus a means to accurately introduce or remove fluid from the patient is provided.

Figure 1A:
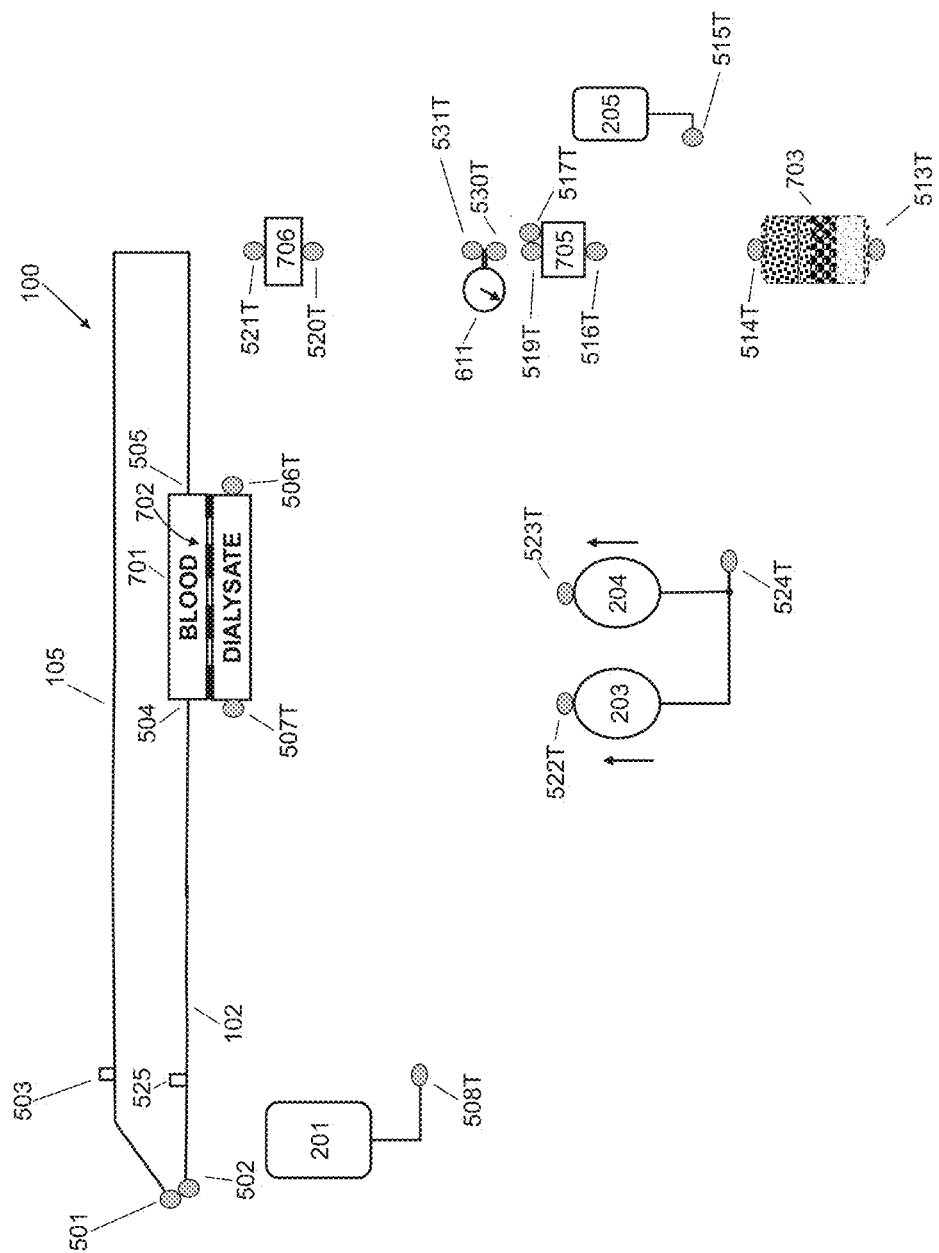
FIG. 1A shows components of a controlled compliant flow path that may be disposable or consumable, together with jumpered ports in accordance with certain embodiments.
Figure 1B:
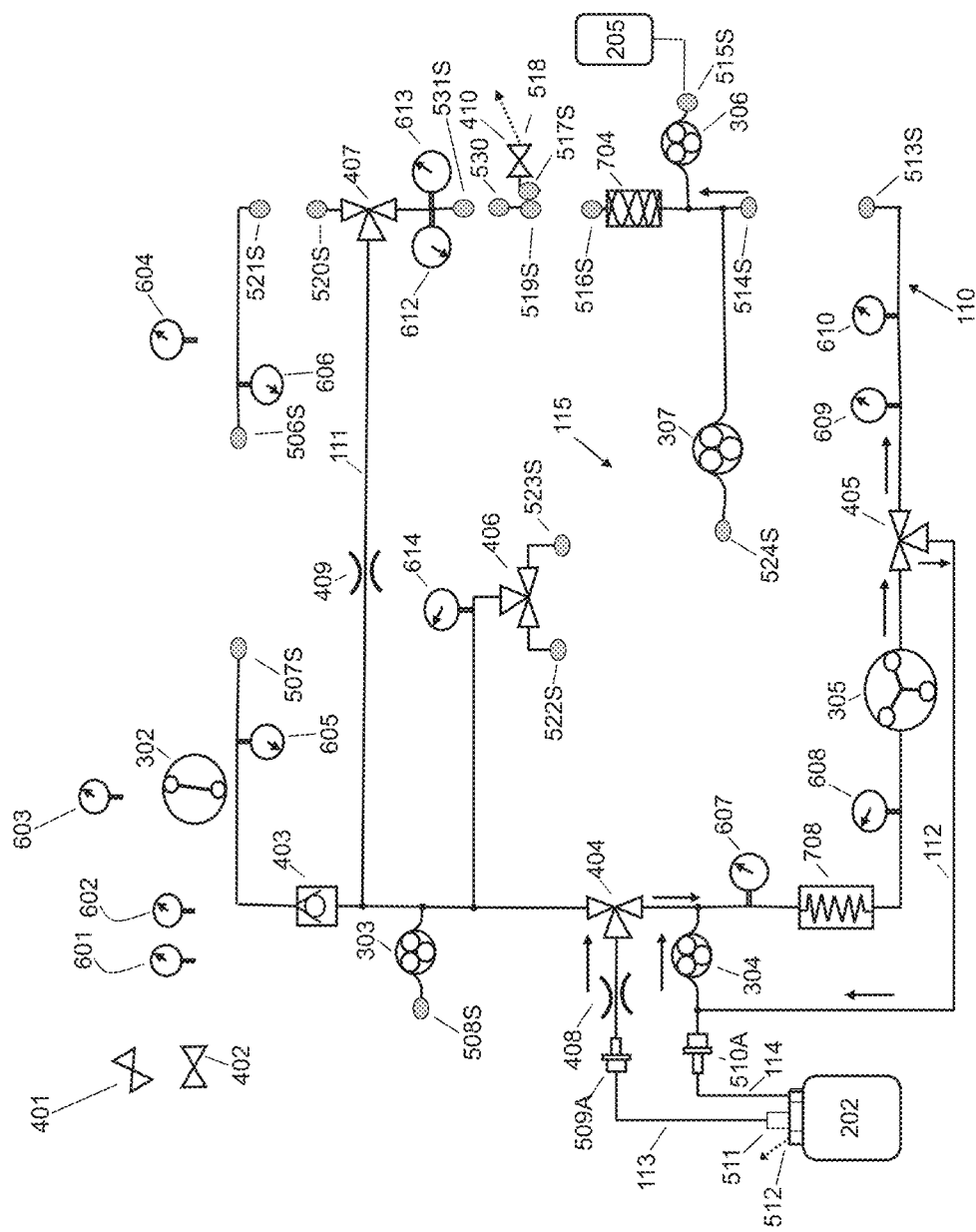
FIG. 1B shows a base module portion of a controlled compliant flow path and jumpered ports of a hemodialysis device having a range of positions where the salination inflow can be drawn from the main controlled compliant flow path.
Figure 1C:
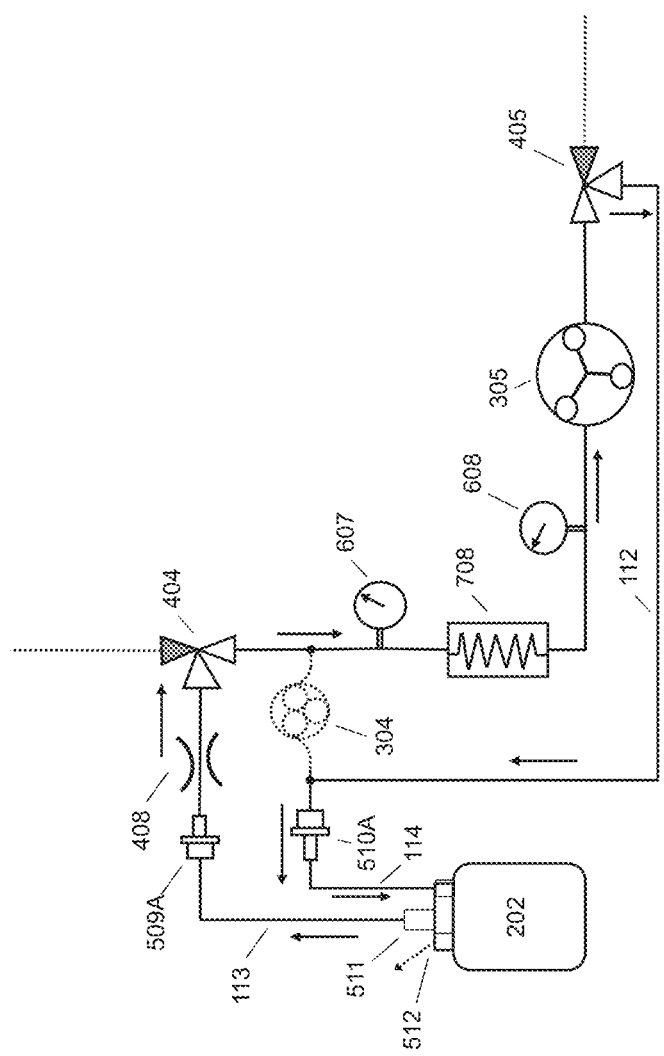
FIG. 1C shows the active portion of a fluid circuit for a hemodialysis device having a controlled compliant flow path during de-aeration of water contained in a water supply reservoir.
Figure 1D:
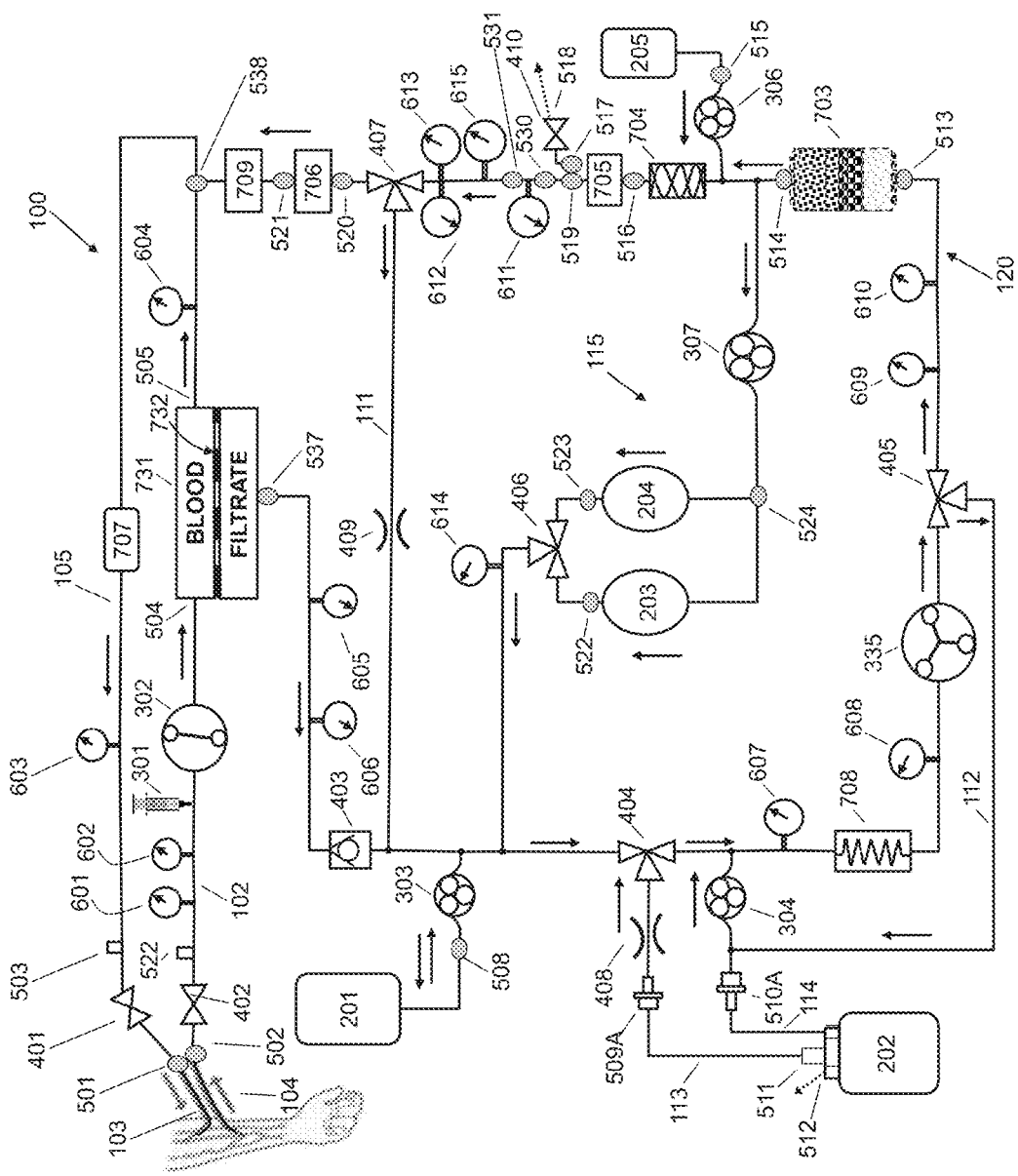
FIG. 1D shows a hemofiltration device having a controlled compliance filtrate regeneration circuit and jumpered ports in accordance with certain embodiments.

FIG. 1D shows an embodiment employing a hemofiltration approach. The components shown in FIG. 1D are comparable to FIG. 1 where the same reference numbers refer to like elements. During hemofiltration, filtrate from the blood is drawn across membrane 732 through filtrate pump 335 and waste species are removed from the blood by the action of solvent drag as the filtrate passes through membrane 732. The pumping rate of filtrate pump 335 determines the rate of convective filtration. As such, a dialysate is not circulated through hemofilter 731. Rather, a filtrate fluid is removed from blood at hemofilter 731 and a replacement fluid is regenerated for reintroduction to the patient via the venous line 105 at port 538 to prevent hypovolemia that would occur due to excessive fluid removal in the absence of replacement fluid return.

The components and conduits that comprise a filtrate regeneration circuit 120 and bypass flow path 111 are substantially inflexible such that a controlled compliance filtrate regeneration circuit is created and, as described for FIG. 1, pumps 303, 304 and 306 can be operated to precisely control net fluid removal or addition to a subject receiving therapy. As such, the fluid balance control pump 303 can be operated in concert with the water pump 304 and acid concentrate pump 306 such that net fluid removal or subtraction from the filtrate regeneration circuit 120, and thus the extracorporeal flow path 100 can be precisely determined and controlled according to a simple volumetric control algorithm that is expressed by as sum of the volumes in given in the following formula. Filtrate regeneration circuit 120 can also be referred to as a solution conduit flow path.

$$\text{Patient Fluid Balance} + \text{Fluid Balance Control Pump} + \text{Water Pump} + \text{Acid Conc. Pump} + \Sigma_{i=0}^{n} X_i = 0$$

"Patient Fluid Balance" refers to the volume of fluid added to or removed from the patient by net movement of fluid removed as filtrate through hemofilter membrane 732 and returned as replacement fluid through port 538 of the extracorporeal flow path 100. The algebraic sign of each term of the above formula is determined by whether the flow is efflux or influx to the filtrate regeneration circuit 120. The term X refers to the volumetric flow rate of a pump where the number of pumps can range for n from 0 to 20. The term "n from 0 to 20" means any integer value of 0, 1, 2, 3, 4, 5, 6, 7, 8, 9, 10, 11, 12, 13, 14, 15, 16, 17, 18, 19, or 20. The formula applies to an instantaneous rate of fluid removal. The instantaneous net fluid removal rate can also be integrated over the time course of therapy to determine the net fluid removal during the elapsed therapy time. Thus, the system can operate the aforementioned pumps to selectively meter in and meter out fluid from the flow loop to accomplish a predetermined patient fluid balance at any time throughout the course of a therapy delivery session.

In some embodiments, the amount of replacement fluid returned to the subject is substantially the same as the volume removed through the hemofilter 731. In other embodiments, the volume of replacement fluid infused into the subject is less than the volume removed through the hemofilter 731 to affect a net fluid removal from the subject.

Filtrate can be removed from the hemofilter 731 through outlet 537 and the pressure of the removed fluid (i.e. filtrate fluid) is monitored by pressure sensor 615. Blood leak detector 605 monitors the filtrate for presence of blood in the filtrate that would indicate a breach of hemofilter membrane 732. FIG. 1 describes the use of system components to modify the composition of a dialysate to maintain physiological compatibility. Similar system components can be used to modify the composition of the regenerated filtrate to produce a replacement fluid for reinfusion to the venous line 105 via port 538.

Prior to the initiation of hemofiltration treatment, the conduits of the system must be primed with a physiologically compatible solution. As described for FIG. 1, water from reservoir 202 is optionally de-aerated and then drawn into filtrate regeneration circuit 120 by action of pump 304. As described, sodium cartridge 203 and bicarbonate cartridge 204, in conjunction with salination valve 406 and pump 307, can be used to generate an predetermined level of sodium ion and buffer to generate a physiologically compatible priming solution. The solution produced can then be circulated through bypass flow path 111, which functions as a priming and recirculation loop, by action of valve 407. In general, the steps for controlling generation the physiologically compatible solution are as follows: (1) H20 pump=Control Pump; (2) Salination pump rate=((solution target/NaCl conc.))×H20 pump rate)+((delta conductivity/NaCl conc.)×solution conduit flow rate).

As described for FIG. 1, the physiological priming solution is moved into the therapy solution reservoir 201 by action of control pump 303 and the process continues until a predetermined amount of physiologically compatible solution sufficient for priming, fluid bolus, and blood rinse-back has been produced and reserved in reservoir 201.

Figure 4B:
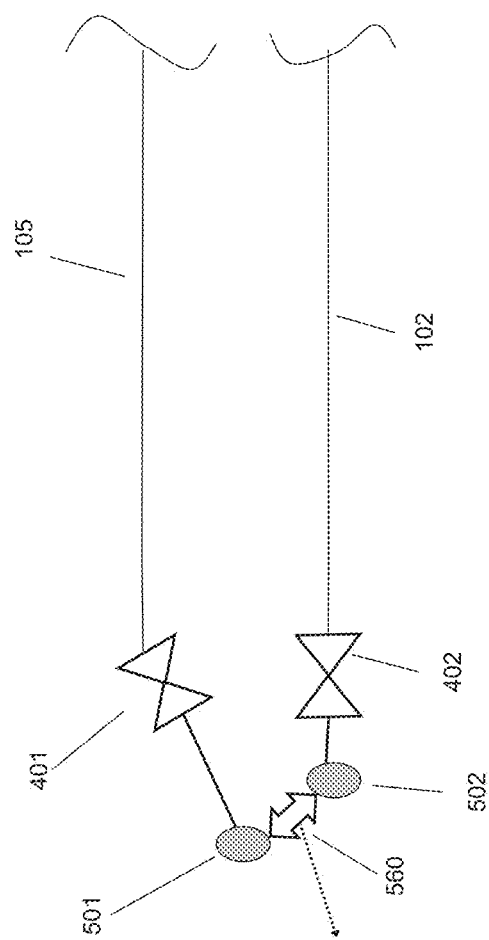
FIG. 4B shows the patient blood access connector ends of the extracorporeal flow path joined at a hydrophobic vent for release of air during priming in accordance with certain embodiments.

Once the predetermined volume of physiologically compatible solution has been produced and moved to the therapy solution reservoir 201, pump 303 can be reversed to begin moving a portion of the prepared solution volume contained in reservoir 201 back to the filtrate circuit and valve 407 is now positioned to allow the solution volume to pass through microbial filters 706 and 709 and into the extracorporeal flow path at port 538. Priming of the extracorporeal flow path continues as described for FIG. 1, except that the physiologically compatible priming solution enters the extracorporeal circuit at port 538 instead of across dialyzer 701 membrane 702, and air in the extracorporeal flow path is moved to a hydrophobic vent 560 located at the terminal ends of extracorporeal flow path 100 as shown in FIG. 4B or into priming over flow reservoir 210 as shown in the examples of FIG. 4A and FIG. 4C. Additionally, as the extracorporeal flow path fills with the priming solution, fluid passes across the hemofilter membrane 732, exiting hemofilter 731 through port 537, returning to the filtrate regeneration circuit 120. Any air passed into filtrate regeneration circuit 120 with the fluid exiting hemofilter 731 at port 537 is exhausted by action of degassing module 705 located in filtrate regeneration circuit 120 before the solution is circulated back to the extracorporeal flow path. During this process, infusates can be added from concentrate reservoir 205 by action of pump 306 to add additional cations and components (e.g. potassium ions, magnesium ions, calcium ions, etc.) to the solution.

Upon initiation of hemofiltration treatment, waste species are removed from the filtration fluid by sorbent cartridge 703. Infusates can be added from concentrate reservoir 205 by action of pump 306 to add necessary cations and components (e.g. potassium ions, magnesium ions, calcium ions, etc.) to regenerate a replacement fluid solution. The treated filtrate is then passed through the degas module 705, microbial filters 706 and 709 to complete preparation of the replacement fluid solution prior to its introduction to the venous line 105 at port 538 for infusion into the patient. The replacement fluid solution may be necessary for preventing hypovolemia, and can replace at least a portion of the fluid volume removed as filtrate from the blood of the subject. Replacement fluid can also be referred to as a substitution fluid wherein such terms are used interchangeably in the present invention. As in FIG. 1, ammonia sensor 611, temperature sensor 612, and conductivity sensor 613 monitor the replacement fluid to verify that it remains within predetermined limits. If the solution composition is outside of predetermined limits, valve 407 diverts the solution through bypass flow path 111, functioning as a priming and recirculation loop, until the fluid has been corrected. Those skilled in the art will understand that the composition of the filtrate (e.g. sodium ion concentration, conductivity) may not always match a desired composition for a replacement fluid. As such, the sodium cartridge 203 and the bicarbonate cartridge 204 can be used to modify the composition of the filtrate as necessary to allow a suitable replacement fluid to be generated. For example, conductivity of the filtrate fluid can be increased using the conditioning pathway 115 by operating pump 307 and valve 406. Similarly, conductivity can be lowered through addition of water from reservoir 202 by action of pump 304 and excess fluid can be removed through operation of pump 303. A additional pressure sensors can be added in the replacement fluid pathway before microbial filter 706 and between microbial filters 706 and 709 to monitor condition of the filters independently. As described for FIG. 1, a fluid bolus can be provided to the subject by delivering additional solution volume from reservoir 201 to the filtrate regeneration circuit 120 via action of pump 303, except that the bolus fluid volume enters the extracorporeal circuit at port 538 instead of passing across dialyzer 701 membrane 702.

Figure 1E:
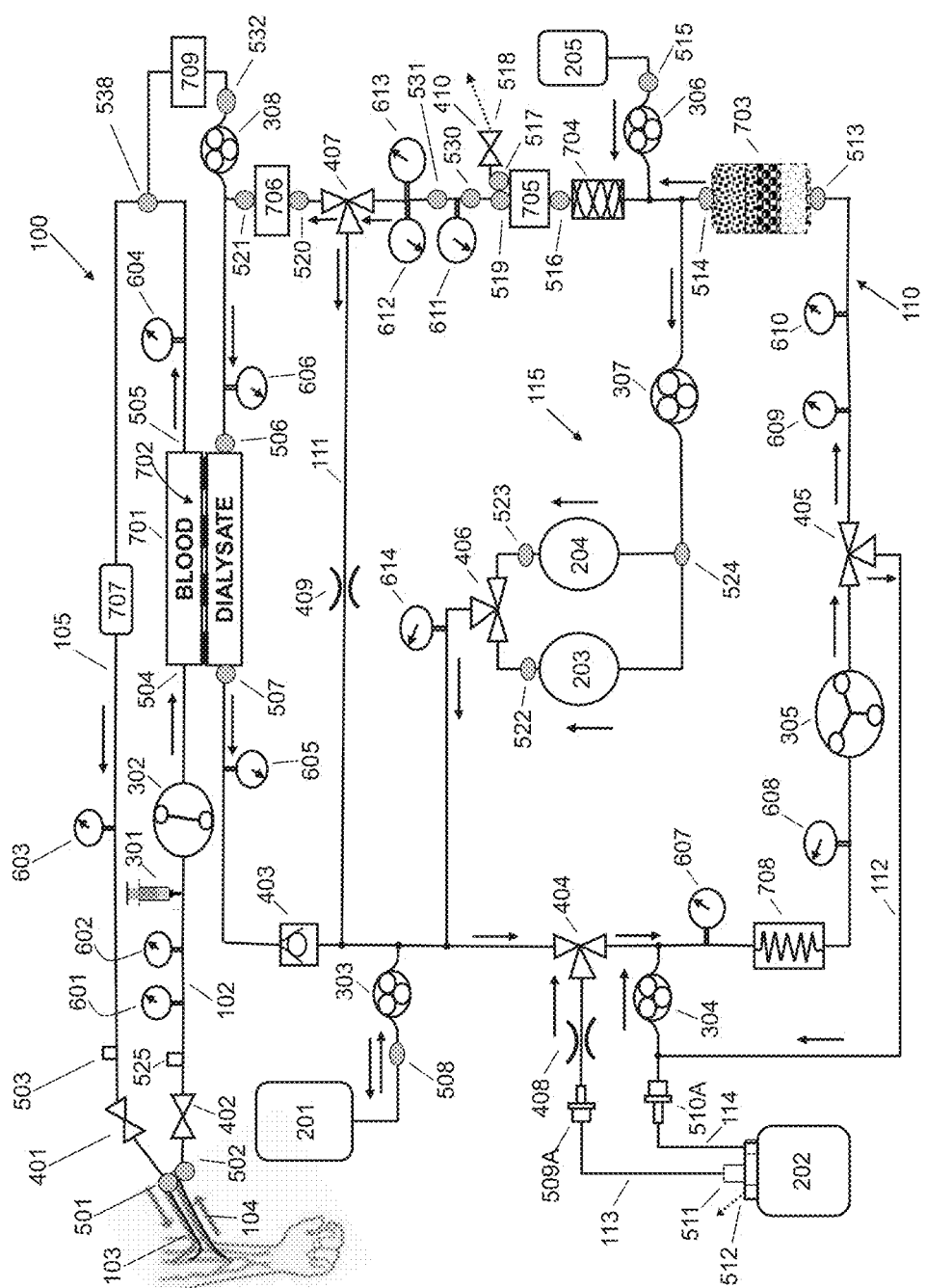
FIG. 1E shows a hemodiafiltration device having a controlled compliance dialysate and replacement fluid circuit and jumpered ports in accordance with certain embodiments.

FIG. 1E shows an embodiment to perform hemodiafiltration therapy. This system is the same as the hemodialysis system shown in FIG. 1, except that a replacement fluid metering pump 308 and a redundant microbial filter 709 have been added to the circuit wherein effluent dialysate exits the dialyzer 701 via outlet 507 and returns via inlet 506. The replacement fluid metering pump 308 may be a reciprocating type piston pump, or a diaphragm pump, or a peristaltic pump. Microbial filter 709 may be an individual microbial filter, or multiple redundant microbial filters in series. Because the controlled compliant flow path 110, also referred to as a solution conduit flow path, has a controlled compliant volume, operation of replacement fluid metering pump 308 causes additional filtrate to be pulled from the blood across membrane 702 into the dialysate compartment for enhanced clearance by convection across the dialysis membrane. This filtrate is combined into the effluent stream passing through dialyzer outlet 507 returning to the sorbent cartridge 703 where impurities are removed. The combined dialysate and filtrate stream is then reinfused with cations from concentrate reservoir 205 and continues toward the dialyzer inlet 506. Prior to reaching dialyzer inlet 506, replacement fluid metering pump 308 redirects a portion of the regenerated fluid through microbial filter 709 as replacement fluid solution into the venous line 105 of the extracorporeal flow path at port 538.

Because of the controlled compliance of the controlled compliant flow path 110, net fluid removal from the subject can be determined by calculating the algebraic sum of the flow rates of control pump 303, water pump 304, electrolyte pump 306 and replacement fluid metering pump 308 per unit time according to the following formula.

$$\text{Patient Fluid Balance} + \text{Fluid Balance Control Pump} + \text{Water Pump} + \text{Acid Conc. Pump} + \text{Replacement Fluid Pump} + \Sigma_{i=0}^{n} X_i = 0$$

The term "Patient Fluid Balance" refers to the volume of fluid added to or removed from the patient by net movement of fluid across the dialyzer membrane 702 and into the extracorporeal flow path 105 at port 538. The algebraic sign of each term of the above formula is determined by whether the flow is efflux or influx to the controlled compliant flow path 110. The formula applies to an instantaneous rate of fluid removal. The instantaneous net fluid removal rate can also be integrated over the time course of therapy to determine the net fluid removal during the elapsed therapy time. The term X denotes the volumetric flow rates of other possible pumps where n can range from 0 to 20. It will be understood that many possible permutations of numbers and types of pumps and reservoirs can be used together in the above described formula without departing from the scope of the invention.

Each of control pump 303, water pump 304, acid concentrate pump 306 and replacement fluid metering pump 308 can be operated under coordinated active control where volumetric pumping rates can be independently adjusted and one or more can be turned on or off as required to achieve a prescribed fluid composition and a prescribed fluid removal from the subject undergoing therapy.

Figure 2:
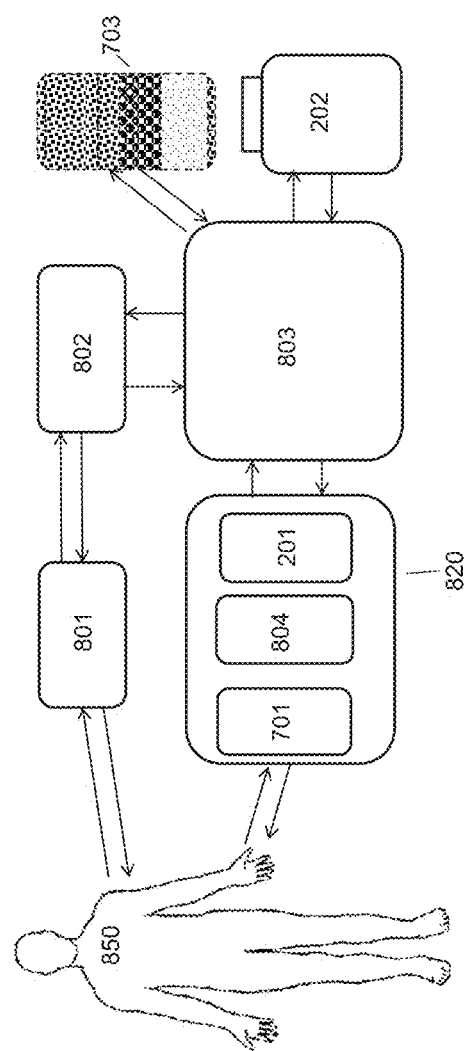
FIG. 2 shows a hemodialysis device having a controlled compliant flow path comprising a user interface, a controller, a base module, a therapy cassette, a sorbent cartridge, and a water reservoir.

FIG. 2 shows an embodiment in which base module 803 is in fluid communication with the controlled compliant flow path components of an optional therapy cassette 820. Therapy cassette 820 can contain consumable and disposable items required for therapy and can be detachably mounted on the base module 803. Therapy cassette 820 can contain a dialyzer 701, one or more infusates 804 and one or more solution reservoir 201. The infusates can be in the form of dry materials or solutions. In some embodiments, the therapy cassette 820 can contain a dialyzer and one or more infusate reservoirs wherein the dialyzer or infusate containers 804 may or may not be fully detachable from the therapy cassette (not shown). In other embodiments, the therapy cassette can contain the dialyzer and one or more solutions reservoir 201 wherein either may or may not be fully detachable from the therapy cassette (not shown). During therapy, the blood circulation of subject 850 is in fluid communication with dialyzer 701 contained in therapy cassette 820. In certain embodiments, connected water reservoir 202 can be detachably connected to the system or formed integrally with one more system components such as the base module 803. During operation, the water reservoir 202 is in fluid communication with the base module. Sorbent cartridge 703 is also in fluid communication with the base module 803. The actions of the base module are controlled by controller 802. Control module 802 sends messages to and receives commands from the user through user interface 801. Whether combined into the optional therapy cassette 820, or individually mounted on base module 803, in any embodiment the dialyzer 701, infusates 804, solution reservoir 201, sorbent cartridge 703 and water reservoir 202 are in fluid communication with the jumpered ports (not shown) of base module 803 to complete a controlled compliant dialysis flow path for purposes of delivering therapy to a subject.

Figure 3:
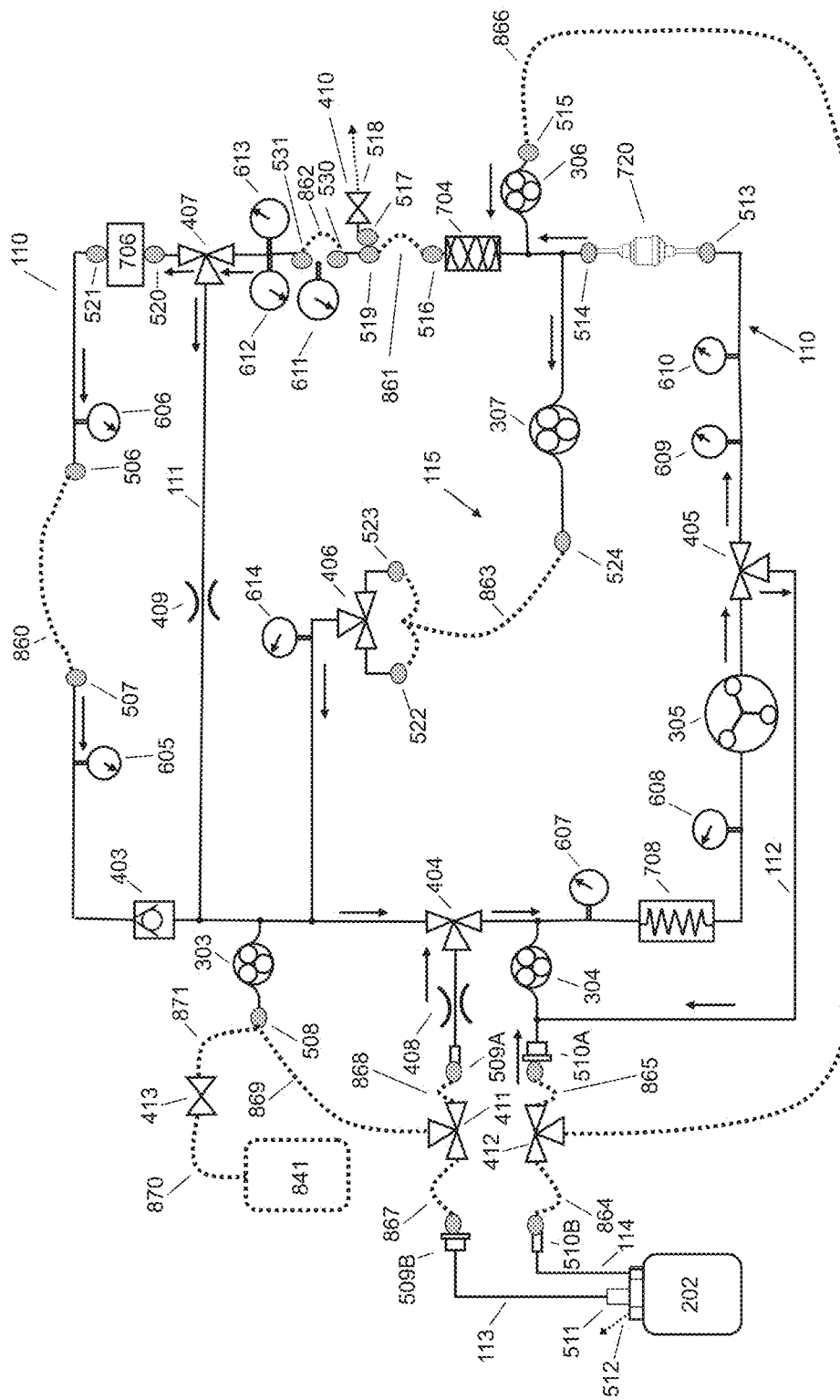
FIG. 3 shows a hemodialysis device having a controlled compliant flow path and jumpered ports in a configuration for cleaning and/or disinfection of the controlled compliant flow path in accordance with certain embodiments.

FIG. 3 shows the re-usable fluid path components and ports of the controlled compliant flow path 110 of FIG. 1 contained within base module 803 of FIG. 2. Dotted lines added to the fluid circuit diagram indicate fluid path connections that are established by jumper pathways 860-871 contained within a cleaning manifold 840 shown in FIG. 6A. The jumpers contained in cleaning manifold 840 complete the fluid circuit segments that were opened by removal of the disposable and consumable components upon therapy completion prior to the cleaning and/or disinfection process. The jumpers create completed fluid circuits to enable fluid to be flushed and recirculated through the re-usable components contained in base module 803 for purposes of cleaning and/or disinfection. The dotted lines shown in FIG. 3 provide a single, non-limiting example of a configuration to jumper the fluid ports. Alternative jumpered port combinations are contemplated by this invention and those skilled in the art will recognize that other combinations of jumpered ports can be employed to create completed fluid circuit pathways for purposes of flushing fluids and recirculation of a cleaning and/or disinfection fluid throughout the re-usable portions of the controlled compliance dialysate fluid circuit.

Figure 5D:
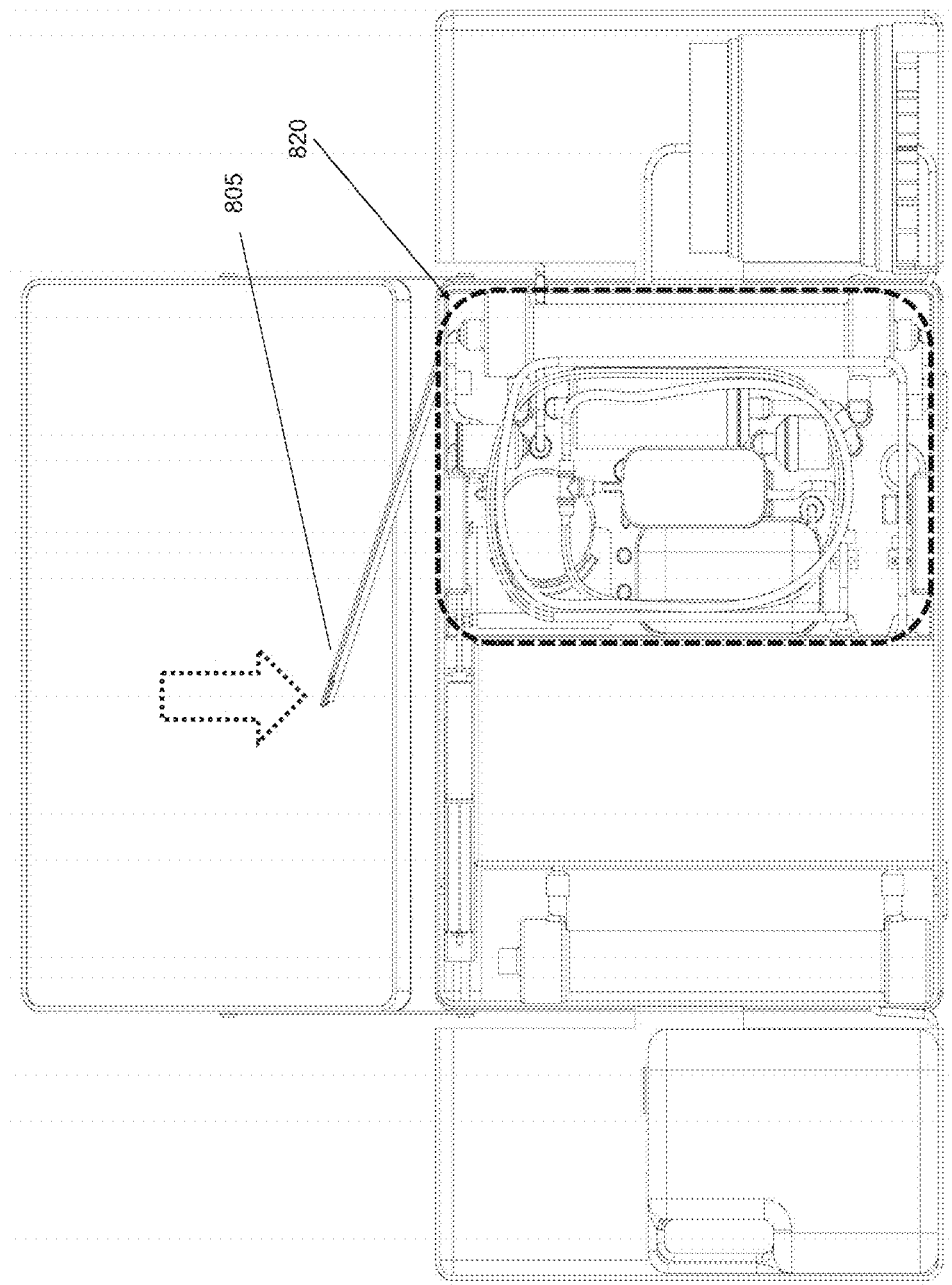
FIG. 5D shows an example of an integrated therapy disposables and consumables cassette, sorbent cartridge, and water supply reservoir installed on a hemodialysis device with a cassette latching mechanism in accordance with certain embodiments.
Figure 6A:
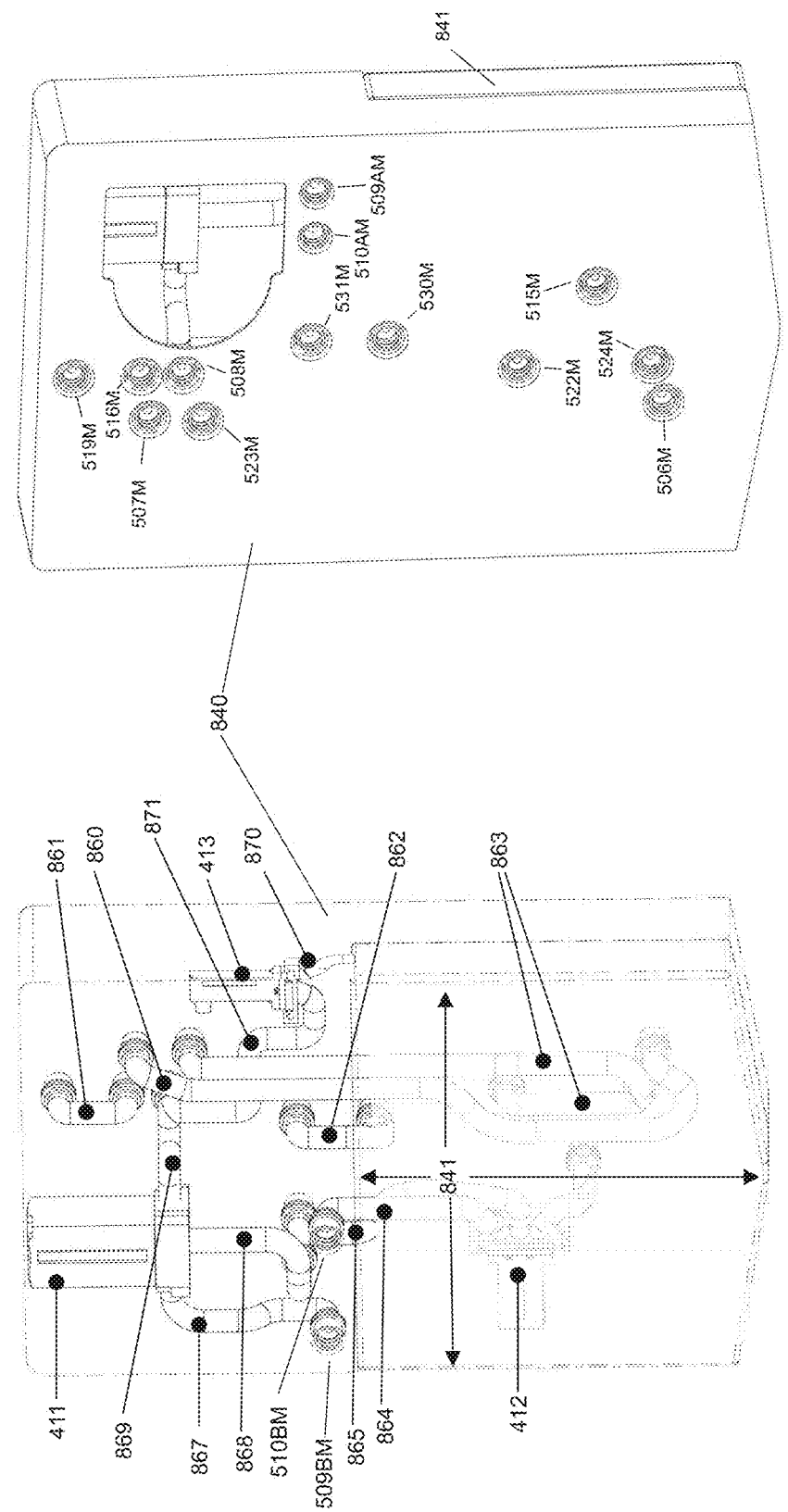
FIG. 6A shows a front and back side of a cleaning manifold with an integrated flush fluid reservoir, fluid circuit jumpers, control valves, and fluid connection ports for use with the hemodialysis device in accordance with certain embodiments.

A cleaning manifold 840 having the fluid circuit jumpers and ports of FIG. 3 is shown in FIG. 6A. The circuit jumpers, or fluid port jumpers, connect to the fluid ports of the base module 803 to complete the fluid circuit where the disposable and consumable components of the controlled compliance controlled compliant flow path have been removed upon completion of therapy. When cleaning manifold 840 is installed on base module 803, the cleaning manifold fluid ports 506M, 507M, 508M, 509AM, 510AM, 515M, 516M, 519M, 522M, 523M, 524M, 530M, and 531M shown in FIG. 6A engage the corresponding fluid ports 506S, 507S, 508S, 509S, 510S, 515S, 516S, 517S, 519S, 522S, 523S, 524S, 530S, and 531S of base module 803 shown in FIG. 5C. FIG. 6A also shows fluid ports 509BM and 510BM that connect to lines 113 and 114 of FIG. 3, respectively, to enable fluid communication between cleaning manifold 840 and reservoir 202. One of ordinary skill in the art will recognize that water reservoir 202 can be bypassed by connecting a suitable water source directly to fluid port 510BM of cleaning manifold 840 if the water source will not require deaeration by the system before use in the cleaning and/or disinfection process.

During cleaning and disinfection a volume of water may be first de-aerated as necessary by the method described earlier. During de-aeration valves 411 and 412, which are contained in cleaning manifold 840, are operated to allow water to flow from water reservoir 202 through line 113, valve 411, valve 404, optionally heater 708, dialysate pump 305, and valve 405 to return to water reservoir 202 through de-aeration bypass conduit 112, valve 412 and line 114.

Before removing sorbent cartridge 703 shown in FIG. 1 from the jumpered flow path shown in FIG. 3, the jumpered circuit is filled with water and a predetermined excess volume of water may optionally be flushed through the jumpered flow path 110. To accomplish this, water is metered into the jumpered flow path 110 by water pump 304, purified by sorbent cartridge 703, circulated through the various flow paths, pumps, and valves of the jumpered flow path 110 shown in FIG. 3 and then passed through flush control valve 413 into flush reservoir 841 that is contained within cleaning manifold 840. In an alternative embodiment, a drain connection can be substituted for flush reservoir 841. Those skilled in the art will recognize that the sorbent cartridge may be removed prior to this step if provisions are made to complete the fluid circuit, such as by jumpering ports 514 and 513 for the flushing step, and if the source water is sufficiently clean such that no further filtration for use as a flushing fluid or if filtration is provided within the cleaning manifold such as at water inlet ports 509BM and 510BM. Next, the sorbent cartridge is disconnected from jumpered controlled compliant flow path 110 and cleaning and/or disinfection concentrate cartridge 720 is connected at ports 514 and 513. Valves 411 and 412 are positioned to prevent flow through water reservoir 202, while allowing flow through base module 803 water intake connection ports 509S and 510S in the recirculating flow path so they can be cleaned and disinfected. Next all pumps shown in FIG. 3 are started and all valves except 413 and 410 are cycled to direct the recirculation fluid through all pathways and distribute the cleaning and/or disinfection concentrate from cartridge 720. Heater 708 is employed to increase the fluid temperature to a temperature that aids disinfection. During the disinfection process the temperature of the heated cleaning and/or disinfection solution is monitored by sensors such as 607, 612 and 614 to verify that the fluid temperature remains within predetermined limits for cleaning and/or disinfection. Additional temperature sensors and temperature sensor locations are contemplated by the invention and those skilled in the art will recognize that the specific location and number of temperature sensors can be tailored to the requirements of individual embodiments.

Disinfection is controlled by a 4-way interaction between fluid temperature, type of disinfectant chemical, disinfectant chemical concentration, and disinfection time. In one, non-limiting preferred embodiment citric acid is employed as the cleaning and disinfectant chemical at a concentration of approximately 2% by weight. Citric acid is effective to remove mineral scale, is relatively non-toxic and biocompatible, and readily reconstituted from a dry chemical form. In one, non-limiting preferred embodiment, the cleaning and disinfection fluid temperature is 80° C. to 90° C., and the disinfection time at temperature is less than 1 hour. In another, non-limiting embodiment, the cleaning and disinfection fluid temperature is around 85° C. and the disinfection time is around 20 minutes. One of ordinary skill will understand that specific temperature and time parameters will be dependent upon the specific embodiment.

At the conclusion of the cleaning and/or disinfection process, the system shuts down and the cleaning manifold 840, disinfectant cartridge 720, and disinfectant fluid are left in place for convenience and to keep the fluid pathways closed to contaminant entry. FIG. 6C shows a cutaway of a base module door 802, revealing that the cleaning and disinfection module 840 may remain in-situ in the stowed configuration.

Figure 5G:
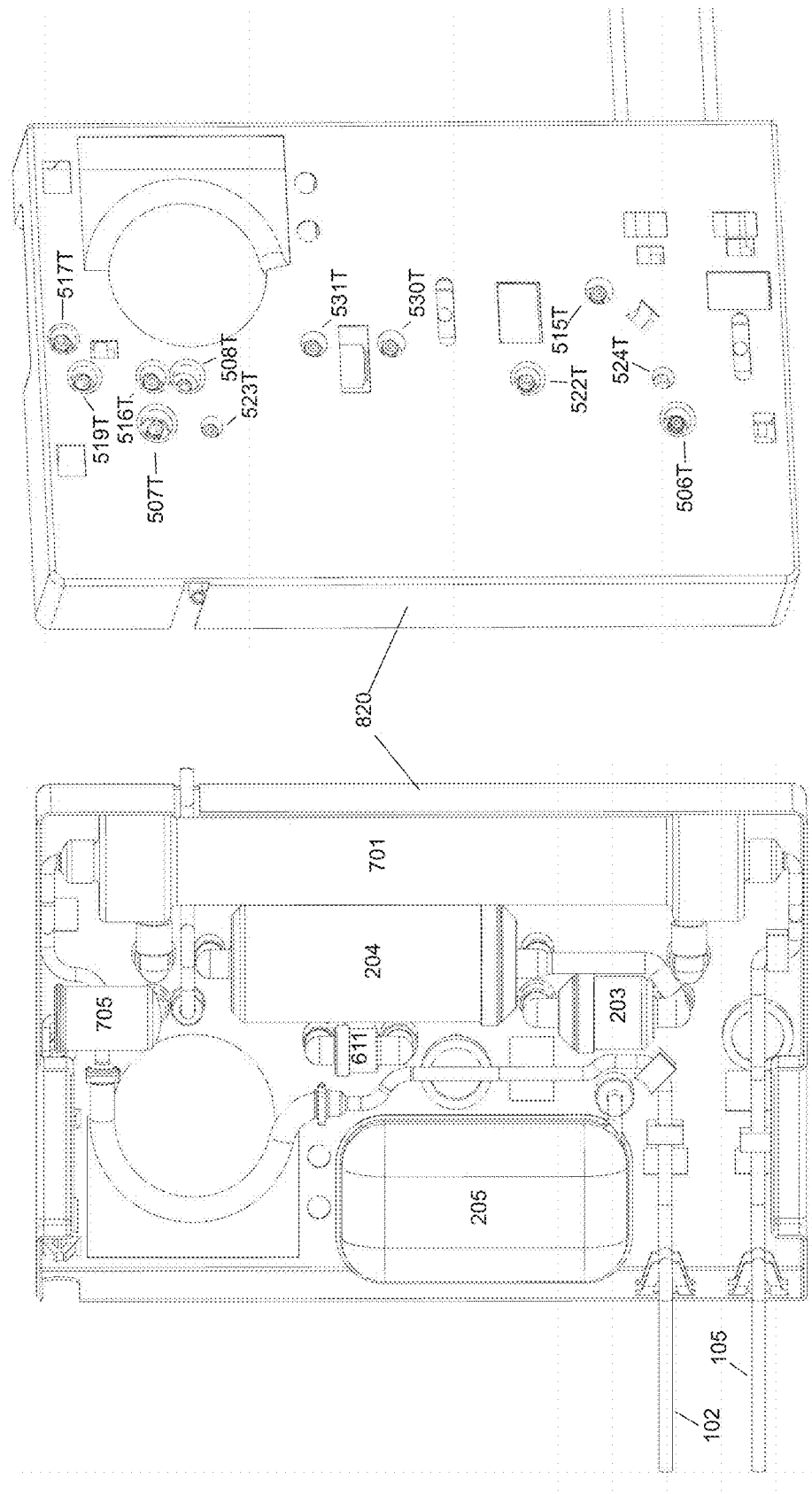
FIG. 5G shows a front and back side of an arrangement of disposables and consumables into an integrated therapy cassette with fluid connection ports in accordance with certain embodiments.

As illustrated herein, for example in FIGS. 1, 5C and 5G, a base module 803 having fluid connection ports 506S, 507S, 508S, 509S, 510S, 515S, 516S, 519S, 522S, 523S, 524S, 530S, and 531S is connected to the disposable and consumable components, optionally organized into the therapy cassette 820, to complete the controlled compliant flow path 110. That is, connections can be made to the base module 803 between a disposable therapy cassette 820, reservoirs such as water reservoir 202, and sorbent cartridge 703 to form a completed jumpered controlled compliant flow path for preparation of a physiologically compatible dialysate. As illustrated herein, for example FIGS. 3, 5C, 6A, a cleaning manifold 840 can be attached to the base module 803 to clean and disinfect reusable portions of the jumpered controlled compliant flow path 110 separate from other portions of the jumpered controlled compliant flow path 110 that may be replaced between uses of the system. In other embodiments, a therapy cassette can contain any combination of one or more disposable or consumable therapy components such as dialyzer 701, extracorporeal flow path 100, cartridges 203 and 204, concentrate reservoir 205, control reservoir 201, sensors such as ammonia sensor 611, and sorbent cartridge 703.

With reference to FIGS. 1, 1D, 1E and 3, the fluid circuitry of the therapy system may be divided into a number of segments that can be combined to form a completed controlled compliance flow path. Segments can be selected from the group consisting of: a first segment having a sorbent cartridge 703 or a cleaning and/or disinfection concentrate cartridge 720 in fluid communication with the controlled compliant flow path 110; a second segment having a concentrate pump 306 in fluid communication with both a reservoir for addition of a concentrate solution 205 and a conduit of the controlled compliant flow path 110; a third segment containing a degassing module 705 in fluid communication with the controlled compliant flow path 110, and a vent control valve 410 in fluid communication with a vent port 517 of a degassing module 705; a fourth segment having at least one salination pump 307 or at least one salination valve 406, and a bypass pathway 115 for conveyance of fluid through a sodium chloride cartridge 203 or a bicarbonate cartridge 204 to a sorbent cartridge 703 without conveyance through a dialyzer 701; a fifth segment having a dialyzer 701 with a blood inlet port 504 and blood outlet port 505 in fluid communication with an extracorporeal flow path 100 and dialysate inlet port 506 in fluid communication with a first microbial filter 706 and dialysate outlet port 507 in fluid communication with a one-way valve 403; a sixth segment that is a bypass flow path 111, functioning as priming and recirculation loop, for conveying fluid from the sorbent cartridge 703 without contacting the dialyzer 701 or passing through a sodium chloride cartridge 203 or a bicarbonate cartridge 204; a seventh segment having a control pump 303 in fluid communication with both a control reservoir 201 and a conduit of the controlled compliant flow path 110; an eighth segment having a water pump 304 in fluid communication with both a water reservoir 202 and a conduit of the controlled compliant flow path 110; a ninth segment having a pump 305 in fluid communication with the controlled compliant flow path 110, a de-aeration bypass conduit 112 in fluid communication with at least a conduit of the controlled compliant flow path 110 and an air vent 512, and a fluid intake bypass valve 404 to direct or to cause fluid movement of fluid from a port 509 of a water reservoir 202 through a flow restriction 408 and pump 305 to de-aerate a fluid; a tenth segment in fluid communication with both a flush reservoir 841 and a pump 303, 304, 306, or 307 in fluid communication with a conduit of the controlled compliant flow path 110; an eleventh segment in fluid communication with at least a port 509 of a water reservoir 202, a flow restriction 408 and a fluid intake bypass valve 404; a twelfth segment in fluid communication with a port 510 of a water reservoir 202, a deaeration bypass valve 405 and a pump 305 in fluid communication with a conduit of the controlled compliant flow path 110; a thirteenth segment having a hemofilter 731 with blood inlet port 504 and blood outlet port 505 in fluid communication with an extracorporeal flow path 100 and a filtrate port 537 in fluid communication with a one-way valve 403; a fourteenth segment having a second microbial filter 709 in fluid communication with a conduit of an extracorporeal flow path 100 and a first microbial filter 706; a fifteenth segment having a second microbial filter 709 in fluid communication with a conduit of an extracorporeal flow path 100 and a replacement fluid pump 308, the replacement fluid pump 308 being in fluid communication with a first microbial filter 706 and a dialysate inlet port 506 of a dialyzer 701.

During priming of the system and treatment of a subject, connection of the disposable and consumable components, optionally organized into therapy cassette 820, to the base module 803 connects the second segment, the third segment, the fourth segment, the fifth segment and the seventh segment to the controlled compliant flow path 110 in order to complete portions of the controlled compliant flow path 110. Installation and connection of sorbent cartridge 703 at ports 513 and 514 completes the first segment. The fourth segment is provided to allow for the presence of sodium cartridge 203 and bicarbonate cartridge 204 to allow for the generation of a physiological compatible dialysate from water provided from reservoir 202.

Attachment of the cleaning manifold 840 in place of the removable disposable and consumable therapy components allows for the re-useable portions of the controlled compliant flow path 110 of base module 803 to be connected into a completed fluid circuit to allow for generation and circulation of a cleaning and/or disinfection fluid. The connections formed by the cleaning manifold 840 are shown by jumpers 860-871 in FIG. 3. In particular, a connection can be made between ports 516 and 519 in lieu of the degas module 705, between ports 506 and 507 in lieu of the dialyzer 701, between ports 522, 523 and 524 in lieu of the sodium chloride cartridge 203 and bicarbonate cartridge 204. Additional connections can be made by cleaning manifold 840 to complete a tenth segment connecting a flush reservoir 841 and a fluid port of the base module pump in fluid communication with controlled compliant flow path 110, for example port 508 and pump 303, of the base module; an eleventh segment connecting water reservoir 202 port 509 to base module port 509S, and hence to flow restriction 408 and fluid intake bypass valve 404 of the base module; and a twelfth segment connecting water reservoir 202 port 510 to base module fluid connection port 510S, and hence to bypass conduit 112 and water pump 304 of the base module. The cleaning manifold 840 attached to the base module 803 completes a jumpered controlled compliant flow path 110 wherein connection of the cleaning manifold 840 to the base module 803 completes or connects the second segment, the third segment, the fourth segment, the fifth segment, the tenth segment, the eleventh segment and the twelfth segment to form the controlled compliant flow path 110.

The use of the base module 803 and the various fluid connection ports are described in Table 1 below in conjunction with the cleaning manifold 840, the disposable and consumable components optionally arranged into therapy cassette 820, and various jumpered connections that can be made between the fluid connection ports. Each fluid connection port can be located on or connected to one or more of the base module 803, the cleaning manifold 840, or the disposable and consumable components optionally arranged into therapy cassette 820. Table 1 states each fluid port as located on the base module 803 or on another system component. If a fluid connection port is part of the base module 803 as shown in, for example, FIGS. 5C and 5G, the ports location as part of the main controlled compliant flow path 110 or the nearest component of the base module fluid circuit is indicated under the "Base Module" column. For example, the sodium cartridge outlet 522 is indicated to make a connection local to the salination valve 406 rather than part of the main controlled compliant flow path 110. Each port located on the base module 803 is used for one or more connections to the cleaning manifold 840 and/or components of therapy cassette 820 or to another system component such as sorbent inlet 513 and outlet 514, where connection to the cleaning manifold 840 and/or component of therapy cassette 820 is not indicated. As described above, sorbent inlet 513 and outlet 514 form connections with the sorbent cartridge 703 or cleaning and/or disinfection concentrate cartridge 720.

The connection of any fluid connection port of the base module 803 to the cleaning manifold 840 or therapy cassette 820 is also indicated under the appropriate column. It should be noted that many fluid connection ports of the base module 803 are used for connection of both the cleaning manifold 840 and the therapy cassette 820. For example, a dialyzer is not used during operation of the cleaning manifold 840. Nevertheless, the dialyzer inlet 506 and outlet 507 ports of the base module 803 are in use regardless of whether the cleaning manifold 840 or therapy cassette 820 is placed. When the components of therapy cassette 820 are placed on the base module 803, appropriate connection is made to the dialyzer, as indicated. When the cleaning manifold 840 is placed on the base module 803, ports 506 and 507 are still required to complete a flow path for the cleaning solution. As indicated in Table 1, ports 506 and 507 both attach to the cleaning manifold 840 and are connected by jumper 860 of the cleaning manifold 840. Ports sharing the same numbered jumper indicate ports that are directly connected by a jumper during placement of the cleaning manifold 840.

It is noted that not all ports indicated in Table 1 are located on the base module 803. For those ports, "no" is indicated under the "Base Module" column, the relevant connection to the cleaning manifold 840 and the therapy cassette 820 is indicated. For example, the patient's venous blood access 501 is connected to the venous line 105 of the extracorporeal flow path 100.

Finally, it should be noted that the port and jumper combinations for the cleaning manifold are a non-limiting exemplary embodiment and other combinations are contemplated by the invention. Those skilled in the art will recognize alternate port and jumper combinations that will enable a cleaning manifold to form a complete jumpered fluid circuit to flush fluids and circulate a cleaning and/or disinfection fluid through the re-usable components of base module 803.

TABLE 1

Connection and Description of Fluid Connection Ports

| Connection or Port | Connection Function | Base Module "S" | Therapy Cassette "T" | Cleaning Manifold "M" | Cleaning Manifold Jumper |
|---|---|---|---|---|---|
| 501 | Patient's venous blood access | No | Venous Line 105 | No | No |
| 502 | Patient's arterial blood access | No | Arterial Line 102 | No | No |
| 506 | Dialysate inlet of dialyzer | Main Controlled compliant flow path 110 | Dialyzer 701 Inlet | Yes | 860 |
| 507 | Dialysate outlet of dialyzer | Main Controlled compliant flow path 110 | Dialyzer 701 Outlet | Yes | 860 |
| 508 | Solution & flush reservoirs | Fluid Balance Control Pump 303 | Solution Reservoir 201 | Flush valve 413 | 869, 871 |
| 509A | Base module de-aeration circuit water inlet | Flow Restriction 408 | No | No | No |
| 509B | Cleaning manifold de-aeration circuit water inlet | No | No | Valve 411 | 867, 868 |
| 510A | Base module water inlet and de-aeration circuit water return | Water Pump 304 or de-aeration bypass 112 | No | No | No |
| 510B | Cleaning manifold water inlet and de-aeration circuit water return | No | No | Valve 412 | 864, 865 |
| 513 | Sorbent inlet, cleaning and/or disinfection concentrate inlet | Main Controlled compliant flow path 110 | No | No | No |
| 514 | Sorbent outlet, cleaning and/or disinfection concentrate outlet | Main Controlled compliant flow path 110 | No | No | No |
| 515 | Cation infusate | Acid concentrate pump 306 | Cation Infusate | Yes | 866 |

TABLE 1-continued

Connection and Description of Fluid Connection Ports

| Connection or Port | Connection Function | Base Module "S" | Therapy Cassette "T" | Cleaning Manifold "M" | Cleaning Manifold Jumper |
|---|---|---|---|---|---|
| 516 | Degas module fluid inlet | Main Controlled compliant flow path 110 | Degas Module 705 Fluid Inlet | Yes | 861 |
| 517 | Degas module gas vent outlet | Vent control valve 410 | Degas Module 705 Vent | No | No |
| 519 | Degas module fluid outlet | Main Controlled compliant flow path 110 | Degas Module 705 Fluid Outlet | Yes | 861 |
| 520 | Microbial filter inlet | Main Controlled compliant flow path 110 | No | No | No |
| 521 | Microbial filter outlet | Main Controlled compliant flow path 110 | No | No | No |
| 522 | Sodium Chloride (NaCl) cartridge outlet | Salination Valve 406 | NaCl Cartridge 203 Outlet | Yes | 863 |
| 523 | Sodium bicarbonate (NaHCO$_3$) cartridge outlet | Salination Valve 406 | NaHCO$_3$ Cartridge 204 Outlet | Yes | 863 |
| 524 | NaCl and NaHCO$_3$ cartridge inlets | Salination pump 307 | NaCl and NaHCO$_3$ Cartridge Inlets | Yes | 863 |
| 530 | Ammonia sensor inlet | Main Controlled compliant flow path 110 | Ammonia Sensor 611 Inlet | Yes | 862 |
| 531 | Ammonia sensor outlet | Main Controlled compliant flow path 110 | Ammonia Sensor 611 Outlet | Yes | 862 |

In FIG. 5A shows an example of the device in a compact configuration that can be used when the device is out of use, stowed or stored. The shelf doors 802 have been closed to provide a protective exterior surface that can protect interior components of the system while also contributing to a transport and storage configuration that has a compact size and may have a smooth exterior surface. User interface 801 is configured in a stowed position, having been nested into an exterior recess in the device such that the potentially fragile side of the interface is protected against the main body of the base unit, leaving only the protective back and side surfaces of user interface 801 exposed, yet positioned flush to the device exterior. This configuration enables a transport and stowage size that can be made compatible with airline carryon luggage size requirements.

In FIG. 5B a retractable handle 803 has been extended and integral wheels 804 are shown that facilitate system transport.

In FIG. 5C hinged shelf doors 802 have been opened to create access to the fluid connection ports 506S, 507S, 508S, 509S, 510S, 515S, 516S, 517S, 519S, 522S, 523S, 524S, 530S, and 531S that are located on the main body of the base module and user interface 801 has been deployed to ready the system for setup. Shelf doors 802 create mounting surfaces for the water reservoir 202 and sorbent cartridge 703.

In FIG. 5D, disposable and consumable therapy components, optionally organized into integrated therapy cassette 820, have been installed on the therapy system after first raising locking lever 805 to allow the system to accept the cassette. A simple straight-on translation perpendicular to the view plane of FIG. 5D has placed the cassette on the system. Locking lever 805 will be pushed down in the direction of the dotted arrow to engage the stator of the peristaltic roller blood pump and at the same time actuate the locking mechanism to lock the cassette 820 in place on the system. The lever 805 shown in FIG. 5D is a non-limiting example and those skilled in the art can readily envision other mechanisms to engage a peristaltic blood pump stator while simultaneously locking the cassette 820 in place.

In FIG. 5E cassette 820 is locked in place. Water reservoir 202 has been filled with water and placed in position on a shelf door 802. Water intake line 113 is connected to base module port 509S and water line 114 is connected to base module port 510S. Sorbent cartridge 703 is shown in position on a shelf door 802 and connected to the controlled compliant flow path at ports 513 and 514. Arterial line 102 and venous line 105 are arranged within the therapy cassette 820 and are joined in fluid communication to priming overflow reservoir 210 by reversible connections.

In FIG. 5F solution reservoir 201 has been unfolded from the therapy cassette and mounted on the rear of the therapy system base module 803. The protective exterior surfaces of shelf doors 802 and the protective back surface of user interface 801 are shown.

In FIG. 5G, the fluid connection ports 506T, 507T, 508T, 515T, 516T, 517T, 519T, 522T, 523T, 524T, 530T, and 531T of the disposable and consumable therapy components that connect to the base module are shown, as optionally organized into a therapy cassette. The therapy cassette features a dialyzer 701, a degassing module 705, a cation concentrate reservoir 205, an ammonia sensing module 611, a dry bicarbonate cartridge 204, and a dry sodium chloride cartridge 203. Arterial line 102 and venous line 105 extend from the cassette.

In FIG. 6A the integrated flush fluid storage reservoir 841 of cleaning manifold 840 that accepts and holds fluids flushed during the cleaning and/or disinfection process is shown. A plurality of jumpers 860-871 create fluid pathways that complete the fluid pathways where the disposable and consumable components of integrated therapy cassette 820 have been removed from the fluid circuit prior to cleaning and disinfection operations. Flush control valve 413 controls flush fluid egress from the jumpered fluid circuit to the integrated flush reservoir 841. The flush control valve 413 can be computer or mechanically operated. One of ordinary skill in the art will understand that any suitable valves for use in fluid lines for dialysis may be used. The valves may be one-, two-, three-, or more-way depending on the desired direction of flow. Again, it will be understood that the present configuration described here is non-limiting wherein many more valve and flow configurations can be designed without departing from the scope of the invention. In the described embodiment, valves 411 and 412 allow fluid to be flushed through the connection ports 509S and 510S (not shown) on the base module 803 for thorough cleaning and/or disinfection. A plurality of ports 506M, 507M, 508M, 509AM, 510AM, 515M, 516M, 519M, 522M, 523M, 524M, 530M, and 531M having integral fluid seals connect to corresponding ports of the base module 803 when the cleaning manifold 840 is placed on the base module after the therapy cassette 820 has been removed.

Figure 6B:
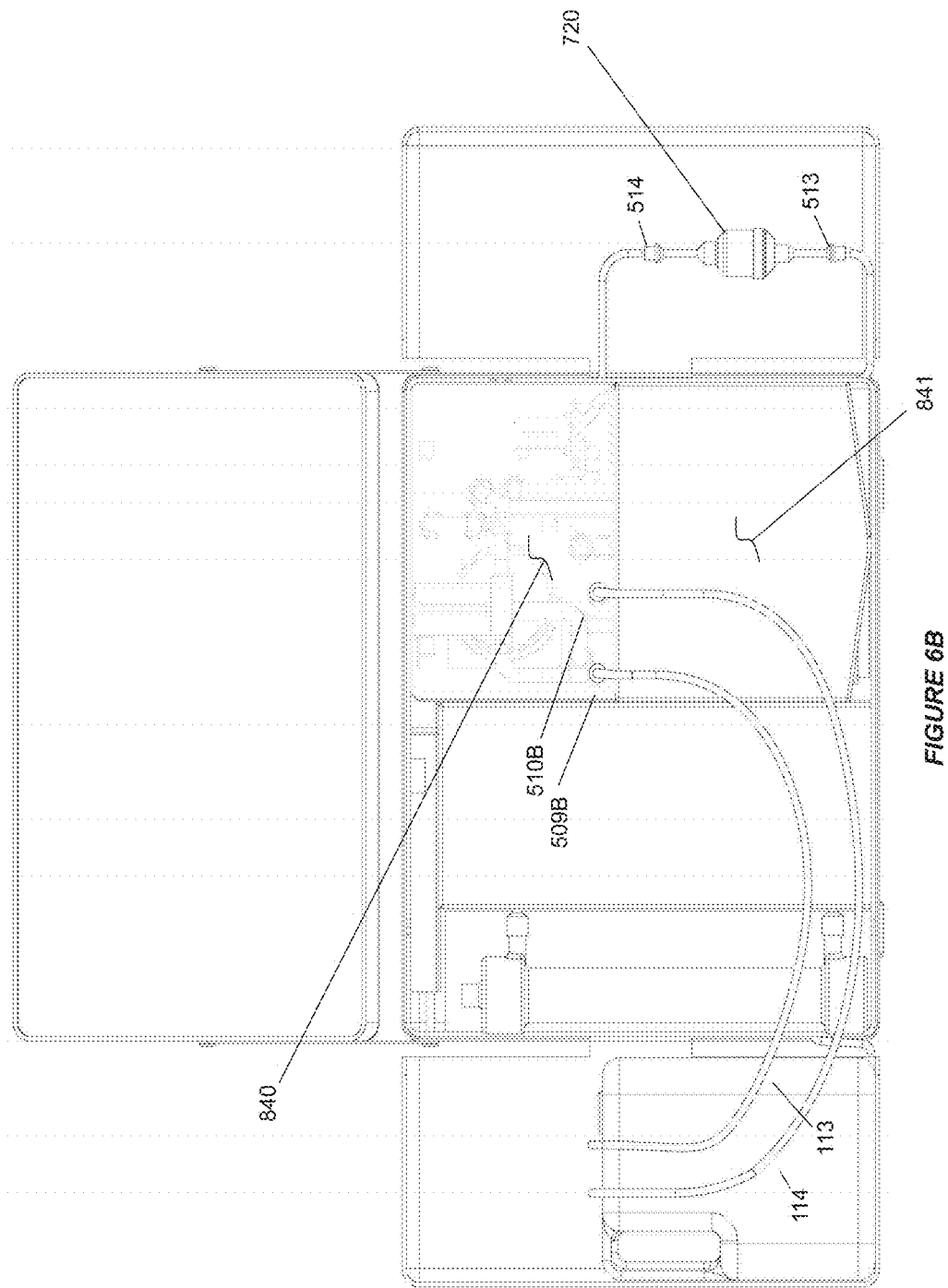
FIG. 6B shows a water reservoir, a cleaning and disinfection manifold, and a cartridge containing cleaning and/or disinfection agent installed on a hemodialysis device in accordance with certain embodiments.
Figure 6C:
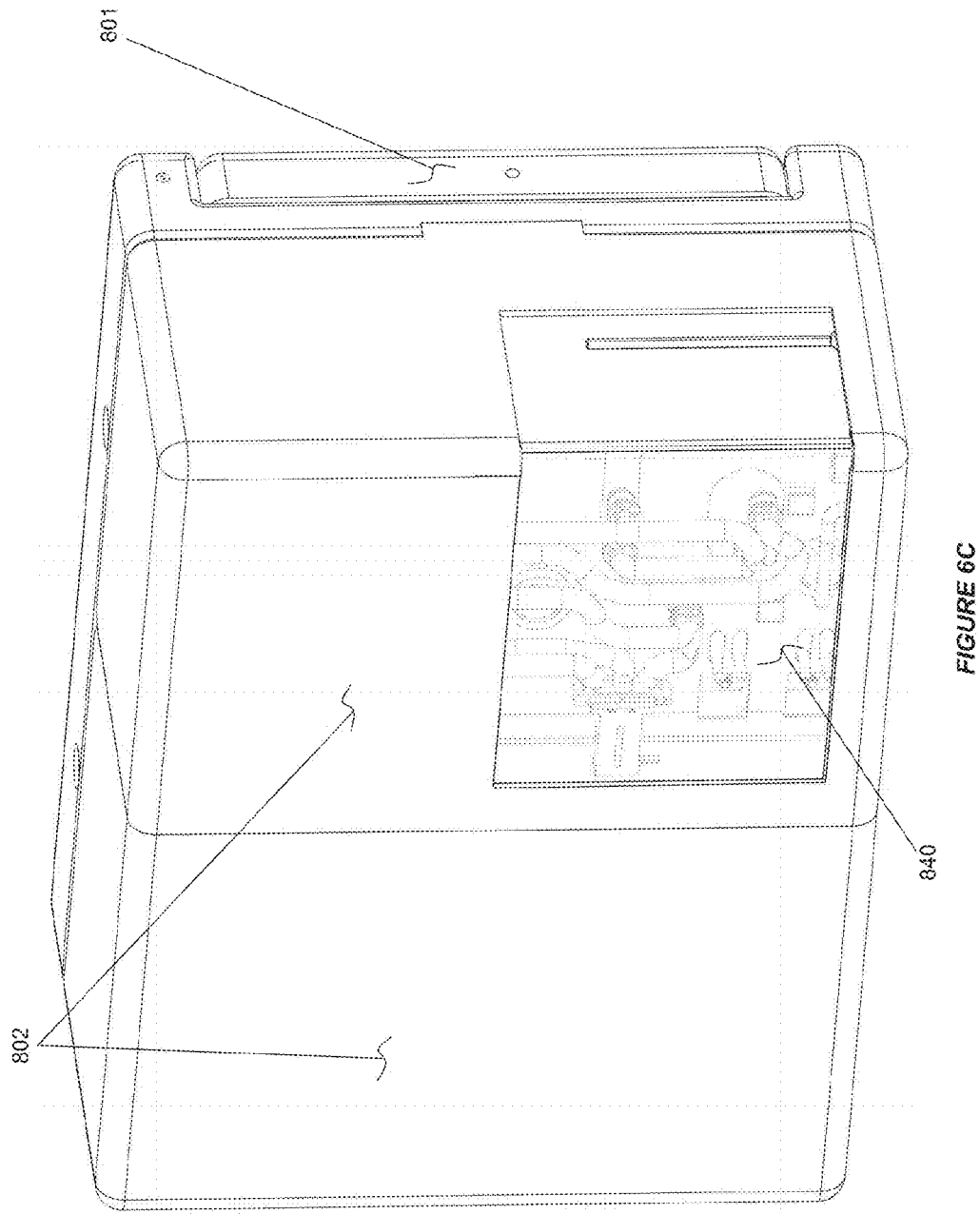
FIG. 6C shows a hemodialysis device folded into storage and stowed transport configuration yet having a cleaning manifold remain in place in accordance with certain embodiments.

In FIG. 6B, a cleaning manifold 840 with integral jumpers 860-871, flush control valves 411-413 and integral flushed fluid reservoir 841 is shown in place on the therapy system. Cleaning and/or disinfection concentrate cartridge 720 is shown connected at ports 513 and 514 to the controlled compliant flow path in place of sorbent cartridge 703 (not shown in this figure).

FIG. 6C shows an exterior view of the system after cleaning and/or disinfection has been completed. A portion of shelf door 802 is cut away to reveal that the cleaning manifold 840 remains in place on the system and the cleaning and/or disinfection fluid remains in the fluid circuit. Shelf doors 802 have been closed and user interface 801 stowed.

Figure 7A:
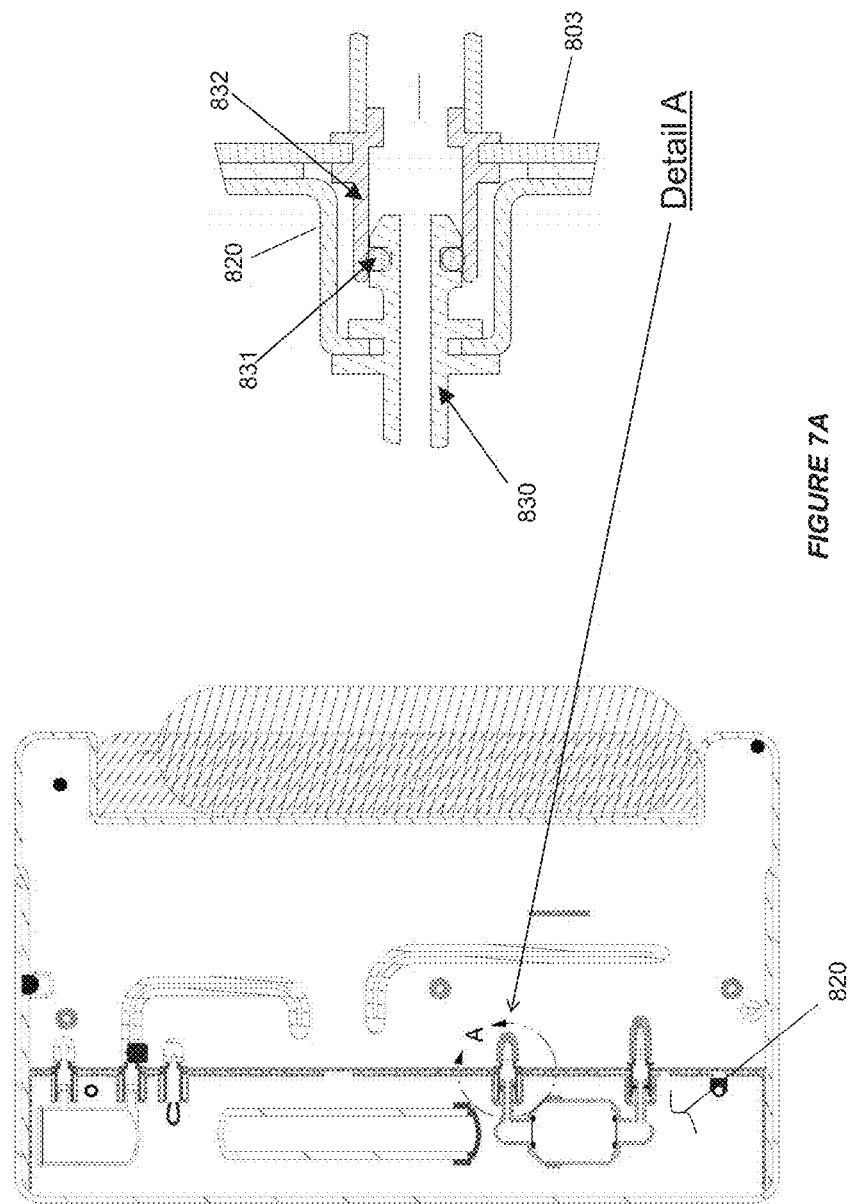
FIG. 7A shows a mating fluid connection port configuration for fluid communication between a fluid pathway of a base module and a fluid pathway of a therapy cassette.

FIG. 7A shows one possible section detail for a mating fluid port connection between a removable disposable or consumable therapy component arranged in a therapy cassette 820 and a fluid pathway of the system base module 803. The mating fluid port connection utilizes a male into female configuration such that the removable therapy component portion of the connection 830 is male and has an integral seal 831 that seals against the internal surface of the female port 832 that forms system base module 803 portion of the fluid interconnect. Connection ports 830 and 832 respectively have male and female configurations that do not limit the configurations to having only round cross sections. One of ordinary skill in the art will understand that other shapes such as oval cross sections can be configured to fit together as a male and female connection wherein such alternative configurations are contemplated by the present invention. Additionally, other sealing configurations known to those of ordinary skill in the art can be used. For example, sealing systems containing one or more O-rings, X-rings, Quad rings, lip seals, spring energized seals can be used. Moreover, one of ordinary skill can use replacements for the removable therapy component portion of the connection 830 using any suitable sealing systems and/or methods known by those of ordinary skill in the art. To provide for a secure seal, a fresh set of seals can be provided by the removable therapy component conduit portion 830 each time a new disposable or consumable component is installed onto the base module 803. It is further contemplated by the invention that check valves known to those of ordinary skill in the art (not shown) can be added to either the male or female half of the connection port to prevent fluid flow when the port is disconnected.

In FIG. 7B, one possible female fluid connection port 843 of the cleaning and disinfection manifold 840 is shown in place on the base module 803 port 832. The base module 803 portion of the fluid connection is 832 and is male and fits inside the female port 843 of cleaning manifold 840. Connection ports 843 and 832 respectively have female and male configurations that do not limit them to having only round cross sections. For example, one of ordinary skill in the art can envision other shapes, such as oval cross sections that can be configured to fit together as a male and female connections for use in the present invention. The seals 845 for this connection are provided on the cleaning manifold port 843. Various configurations and materials for the seals 845 are contemplated by the invention. The double seals 845 are intended to be illustrative in nature and not intended to limit the scope of the present invention. Those of ordinary skill in the art can envision other possible seal configurations such as O-rings, X-Rings, Quad-rings, lip seals and spring energized seals.

It will be recognized by one skilled in the art that the port configurations shown in FIGS. 7A and 7B are complimentary and work in combination to ensure that all fluid port surfaces that may contact the therapy solution, or dialysate will always be reliably exposed to the cleaning and/or disinfection fluid. Further, the external end surfaces of the base module 803 fluid port tubes 832 are also exposed to the cleaning and/or disinfection fluid, which ensures that microbial growth is not allowed to be present at the ends of the base module 803 fluid connection port tubes 832 and become transferred to the therapy solution contacting end surfaces of the removable therapy component male connector 830. The specific placement of the ports need not exactly conform to those depicted where other configurations for achieving the intended purposes of the invention can be used and many alternative configurations can be envisioned without departing from the scope of the invention.

Figure 8:
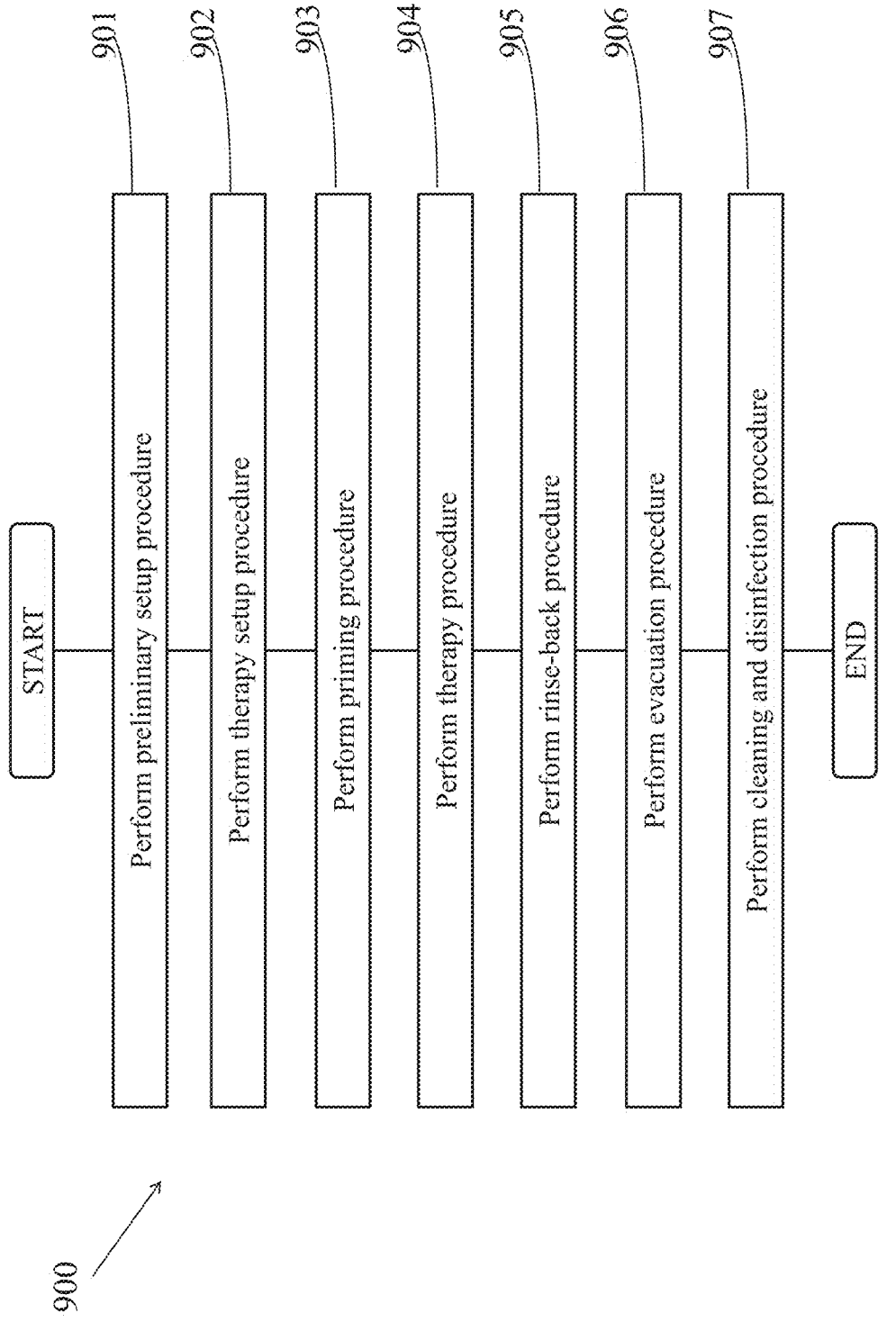
FIG. 8 shows a method of operating a hemodialysis device in accordance with certain embodiments.

A method of circulating blood and a dialysate through a dialyzer using a hemodialysis device having a controlled compliance flow path and having a range of positions where the conditioning pathway 115 outflow can be infused into the main controlled compliant flow path is shown in FIG. 8, for example, using the hemodialysis device illustrated in FIG. 1A representing one embodiment of the disposable and consumable therapy components only connected in fluid communication with one segment of a dialysate flow path. As shown in FIG. 1A, the fluid connection ports 506T, 507T, 508T, 522T, 523T, 524T, 514T, 513T, 515T, 516T, 517T, 519T, 530T, 531T, 520T, and 521T can connect to the corresponding fluid ports of a base module. The removable disposable and consumable therapy components in the present, non-limiting examples include a degassing module 705, an ammonia sensing module 611, a dry bicarbonate cartridge 204, a dry sodium chloride cartridge 203, a cation concentrate reservoir 205, a solution reservoir 201, a dialyzer 701, and an extracorporeal flow path 100. However, additional permutations or groupings of components are contemplated, such as the dialyzer and dry bicarbonate cartridge.

With reference to FIG. 8, in the first step of the method of circulating blood and a dialysate through a dialyzer 900 a preliminary setup procedure 901 can be performed to change the configuration of the hemodialysis device from a stowed or transport configuration to an open and ready configuration. In the next step, a therapy setup procedure can be performed 902 to further prepare the hemodialysis device for a hemodialysis therapy session by attaching the components and materials required to perform therapy. Next, a priming procedure can be performed 903 to initially fill a controlled compliance flow path and extracorporeal circuit with a physiologically compatible solution, such as a dialysate. Then, a therapy procedure is performed 904 to circulate blood and the dialysate through a dialyzer. When the therapy has been completed, a rinse-back procedure can be performed 905 to return the blood from the extracorporeal flow path. Then, an evacuation procedure can be performed 906 to remove fluid from the extracorporeal flow path and controlled compliant flow path. Finally, a cleaning and disinfection procedure can be performed 907 to prepare the hemodialysis device for storage before a future dialysis session.

The solutions or fluids required for a hemodialysis therapy session can include a fluid to prime the dialysate flow path, a fluid to prime a dialyzer and extracorporeal flow path, a fluid to provide a bolus infusion to a subject receiving therapy, and a fluid to rinse blood contained in the dialyzer and extracorporeal flow path back to the subject at completion of therapy. The solutions or fluids required for a hemofiltration therapy session can include a fluid to prime the filtrate flow path, a fluid to prime a hemofilter and extracorporeal flow path, a fluid to provide a bolus infusion to a subject receiving therapy, a replacement fluid, and a fluid to rinse blood contained in the hemofilter and extracorporeal flow path back to the subject at completion of therapy. The solutions or fluids required for a hemodiafiltration therapy session can include a fluid to prime the dialysate flow path, a fluid to prime a dialyzer and extracorporeal flow path, a fluid to provide a bolus infusion to a subject receiving therapy, a replacement fluid, and a fluid to rinse blood contained in the dialyzer and extracorporeal flow path back to the subject at completion of therapy. The procedures of method 900 will describe the steps to produce fluids that are physiologically compatible in terms of chemistry and having microbiological purity for these uses.

Figure 9:
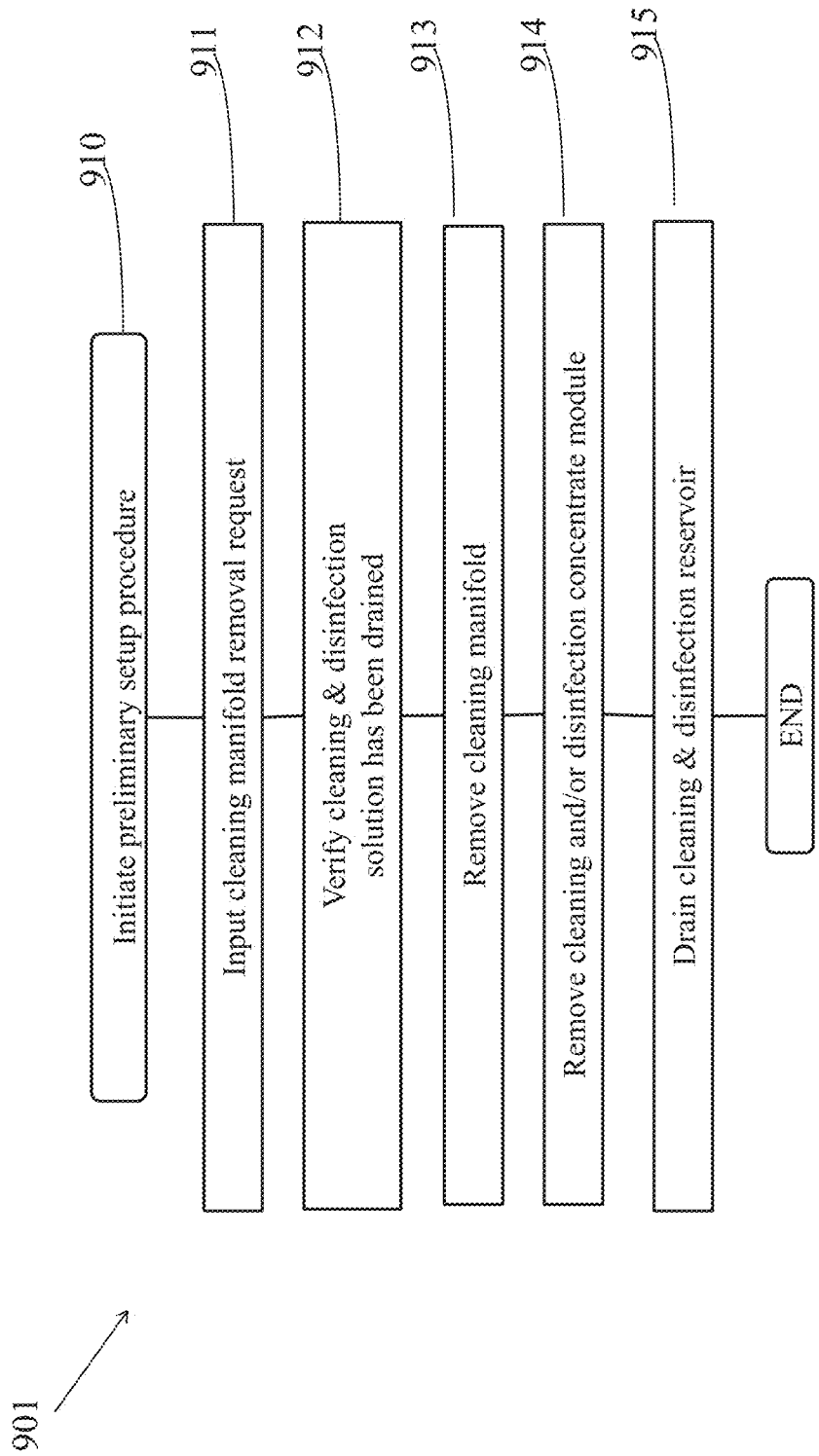
FIG. 9 shows a method of setting up a hemodialysis device in accordance with certain embodiments.

Further, a detailed sequence of steps will be disclosed for each of the individual steps of the method 900. With reference to FIG. 9, the preliminary setup procedure 901 to configure the hemodialysis device equipment can be performed by a user in conjunction with simultaneous monitoring by the hemodialysis system to verify and confirm correct setup of the equipment. In some embodiments the user can be a therapy subject.

Referring to FIG. 9, at initiation of system setup for the next therapy session, the user can enter a request to remove the input cleaning manifold 911, which generally remains installed on the base module between therapy sessions to ensure the fluid pathways remain free of contamination. For example, in an embodiment shown in FIGS. 2 and 5C, a user can initiate the preliminary setup procedure by turning on system power and selecting Setup Mode via user interface 801. The user further can enter a request through user interface 801 to remove cleaning manifold 840 and start the setup process for a therapy session. The system or device then can cycle the pumps and valves in sequence to drain the cleaning and/or disinfection solution from the fluid pathways and components of controlled compliant flow path 110, conditioning flow path 115 through pump 307 and valve 406, bypass flow path 111, metering pumps 303, 304 and 306 the cleaning and/or disinfection concentrate cartridge, and the cleaning manifold jumper lumens. The drained fluid is collected in integrated reservoir 841 contained in cleaning manifold 840. Optionally, in some embodiments, water reservoir 202 can be filled with water and connected to cleaning manifold ports 509BM and 510BM to allow fresh water flushing of the cleaning and/or disinfection solution as a first part of the fluid draining step.

In the next step, the user verifies that the cleaning and/or disinfection solution has been drained from a cleaning and/or disinfection cartridge and a cleaning manifold 912 in FIG. 9. Alternatively, in any embodiment the system can return a message to the user via user interface 801 in FIGS. 2 and 5C that the user may now remove cleaning manifold 840 and cleaning and/or disinfection concentrate cartridge 720. For example, and throughout operation, the system may intermittently activate sensors to confirm removal or correct loading of components and materials. In any embodiment, the hemodialysis device can communicate through visual, audible, or tactile signals to the user during the process to confirm successful completion of setup tasks, or to provide corrective feedback to complete the task.

In the next step, the user removes the cleaning manifold 913 and removes cleaning and/or disinfection concentrate cartridge 914. The user can drain the contents of cleaning manifold reservoir 915, for example, by gravity, into a suitable disposal and the cleaning manifold 840 can be retained for re-use at completion of the next therapy session.

Figure 10:
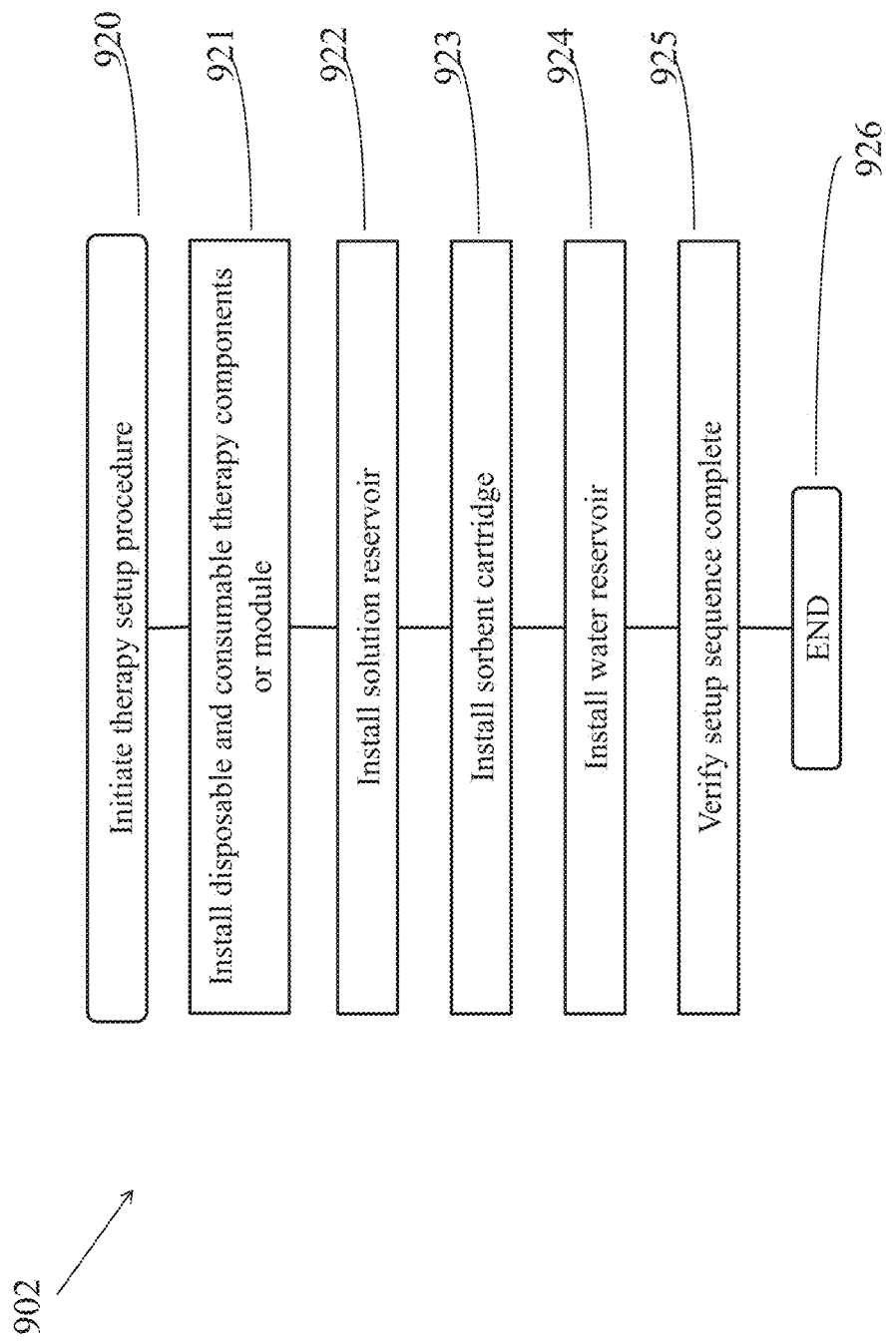
FIG. 10 shows a method of setting up a hemodialysis device in accordance with certain embodiments.

Referring now to FIG. 10, therapy setup procedure 902 begins in step 920 and the user can install a the disposable and consumable therapy components 921. For example, referring to FIG. 1, arterial pinch valve 402 and venous pinch valve 401 can be opened so that blood lines 102 and 105 of extracorporeal flow path 100 can be inserted. With reference to FIGS. 5C and 5D, the user can place disposable and consumable components that are optionally arranged as therapy cassette 820 onto the invention and engage latch mechanism 805 wherein the arterial pinch valve 402 and venous pinch valve 401 are reset to the normally closed position. In any embodiment, sensors may be used to confirm that the disposable and consumable components or therapy cassette 820 are properly engaged and user interface 801 can signal to user that task is successfully completed, or provide corrective feedback to complete the task.

The user then can install the solution reservoir 922. Referring to FIGS. 1 and 5E, if a solution reservoir 201 has been included in a cassette such as 820, user can re-position solution reservoir 201 from therapy cassette 820 and place it in the operating position on system. In any embodiment, optional sensors may be used to confirm the solution reservoir is properly placed and the user interface can signal to the user that the solution reservoir installation task is successfully completed, or can provide corrective feedback to complete the task.

Next, the user can install the sorbent cartridge 923 as shown in FIG. 10. In an embodiment shown in FIGS. 1 and 5E, the user can install the sorbent cartridge 703 on system and connect the sorbent cartridge 703 inlet and outlet ports 513, 514 to the controlled compliant flow path connectors, respectively. In any embodiment, sensors may be used to confirm the sorbent cartridge has been properly engaged and signals sent to user that task is successfully completed such that the sensors can provide corrective feedback to complete the task.

Then, the user can install the water reservoir 924 as shown in FIG. 10. In an embodiment illustrated in FIGS. 1 and 5D, the user can fill water reservoir 202 with potable water or other types of water suitable for use in the present invention, place it on the therapy system, and connect it to the fluid intake ports 509S and 510S of the system. In any embodiment, the user can transport water including potable water to the water reservoir 202 and fill it in place on the system. In any embodiment, sensors may be used to confirm that the water reservoir 202 is properly filled and engaged wherein the user interface signals to user that the water reservoir installation task is successfully completed, or provides corrective feedback to complete the task.

In the next step, the user can verify that the setup sequence is complete 925. In any embodiment, the user interface can display a message that the setup sequence has been successfully completed and prompt the user for authorization to initiate a system priming sequence.

Figure 11:
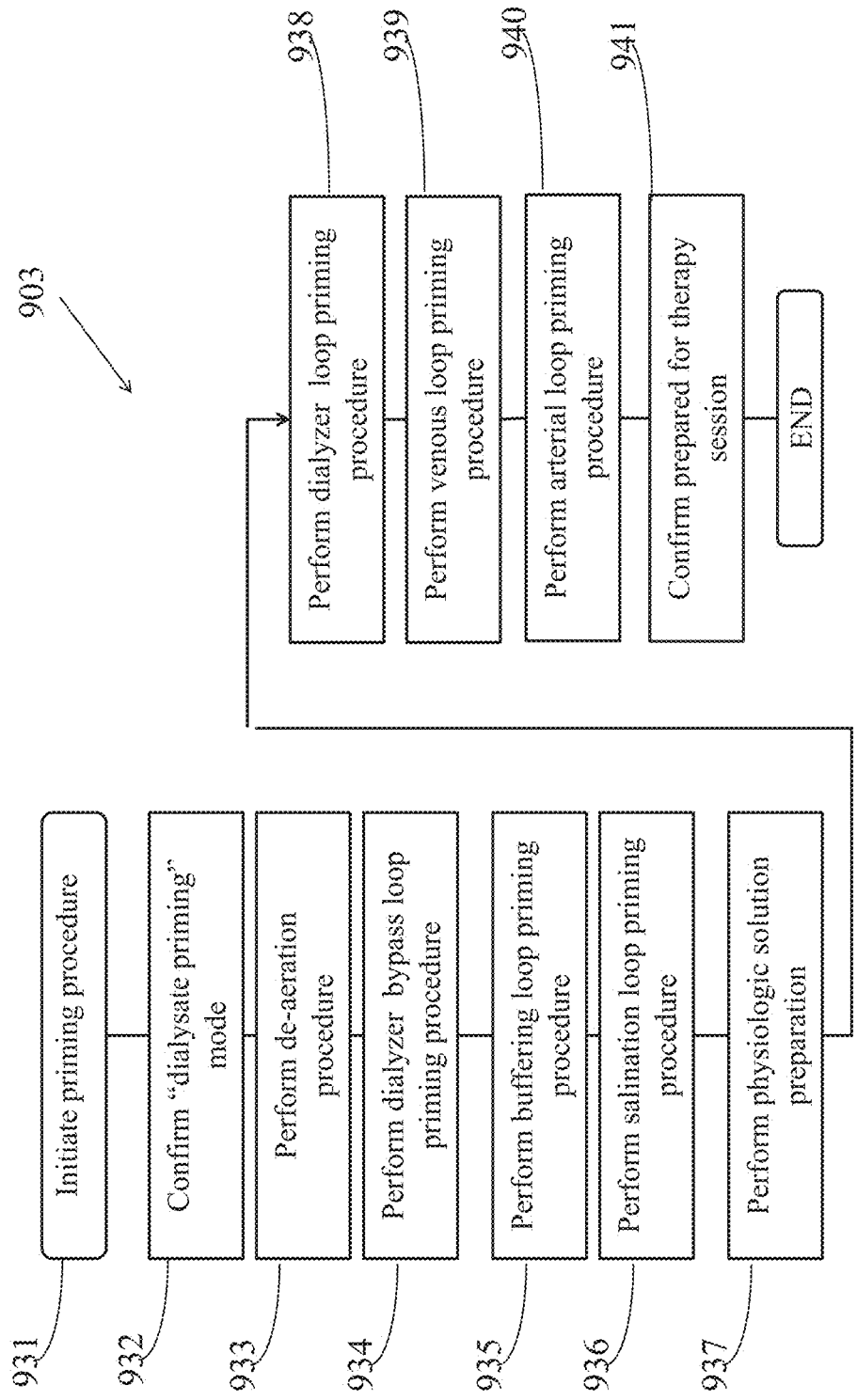
FIG. 11 shows a method of priming a hemodialysis device in certain embodiments.

A detailed priming procedure is shown in FIG. 11. First, the user can initiate the priming procedure 931 to fill and prime a hemodialysis device dialysate flow path and extracorporeal flow path. In any embodiment, the filling and priming process can be automatically performed by the hemodialysis device. For example, in an embodiment shown in FIGS. 2 and 5E, the user can initiate the priming sequence through a user interface and the fluid circuit priming sequence can proceed automatically under control of a controller. Next, the device can confirm it has entered the dialysate priming mode 932, for example, by displaying a message on the user interface.

In the next step, a de-aeration procedure can be performed 933. For example, in an embodiment corresponding to FIG. 1C, the valves states can be switched or positioned to create a de-aeration recirculation fluid circuit loop. Fluid intake bypass valve 404 can open a flow path connecting water intake line 113 to the controlled compliant flow path in the direction of the heater 708 only, and de-aeration bypass valve 405 can open a flow path from the dialysate pump 305 to the de-aeration bypass conduit 112 only. In this example, the water intake pump 304 is not operated, thus causing any flow through de-aeration bypass conduit 112 to be directed back to the water reservoir 202 through water line 114.

Further, the dialysate pump 305 can be operated to pull water into the circuit from water reservoir 202 through flow restriction 408 at a flow rate such that the absolute pressure of the fluid is reduced sufficiently, by the, within the restriction to release a majority of the dissolved air from solution and convert it to air bubbles that can be vented from the circuit through vent opening 512 in water reservoir 202 as the water returns to water reservoir 202. At the same time, optionally, heater 708 can be operated to heat the water flowing through the recirculating de-aeration loop to a predetermined temperature, further reducing the solubility of air in water and enhancing the de-aeration process. Optionally, the water can be circulated and heated in the de-aeration loop for a pre-determined time period sufficient to de-aerate the water. In certain embodiments, an optional air bubble detector 608 can be positioned in the de-aeration fluid loop to monitor and confirm that the air is sufficiently removed from the water. When air bubbles are no longer observed passing a bubble detector after a predetermined time, the water is sufficiently degassed to continue to the next step of the process.

In the next step, a dialyzer bypass loop priming procedure can be performed 934 to mix a physiologic solution and store the solution in a reservoir. For example, in an embodiment corresponding to FIG. 1, the valve states can be set to create the mixing and filling fluid circuit. Fluid intake bypass valve 404 closes the water inlet path through flow restrictor 408 and opens the controlled compliant flow path between pumps 303 and 304. De-aeration bypass valve 405 closes the de-aeration bypass conduit 112 and opens the controlled compliant flow path from dialysate pump 305 through sorbent cartridge 703, and dialyzer bypass valve 407 is set to direct flow from the outlet port 519 of degassing module 705 to the bypass flow path 111. Passing water through the materials contained in the sorbent cartridge can purify the water by removing organic, inorganic and microbial contamination from the water as the water passes through the sorbent cartridge.

With reference to FIG. 1, the dialysate loop can initially be filled as water intake pump 304 and dialysate pump 305 begin pumping to intake water and recirculate it through the bypass flow path 111. Water pump 304 can be operated until the fluid pressure measured at pressure sensor 610 rises to a predetermined level. The rate of water pump 304 is then controlled to maintain the fluid pressure within a predetermined range by pumping in additional fluid as air is exhausted from the fluid circuit through degassing module 705. Bubble detector 608 can be monitored and the recirculation continued until no more air is detected in the line. In any embodiment, air from the operating portion of the controlled compliant flow path can be trapped in degas module 705 and exhausted through vent port 517 and vent control valve 410 during this sequence.

In the next step, a buffering loop priming procedure can be performed 935. For example, in an embodiment in accordance with FIG. 1, in order to prime the dry sodium bicarbonate cartridge 204, salination valve 406 can open a flow path through outlet port 523 of bicarbonate cartridge 204 to the junction with the controlled compliant flow path between pump 303 and pump 304, and the salination pump 307 can be started while water intake pump 304 and dialysate pump 305 continue to operate as per the previous sequence. The buffering loop priming procedure is concluded when the air bubbles have passed bubble detector 608 and a conductivity increase is observed at conductivity sensor 613. In any embodiment, air from the bicarbonate cartridge 204 is moved to degas module 705, trapped, and exhausted from the fluid circuit at vent port 517 through vent control valve 410 during this sequence.

Continuing to the next step, a salination loop priming procedure can be performed 936. For example, in an embodiment shown in FIG. 1, in order to prime the dry sodium chloride cartridge 203, salination valve 406 can open a flow path through outlet port 522 of sodium chloride cartridge 203 to the junction with the controlled compliant flow path between pump 303 and pump 304, and the water intake pump 304 and the dialysate pump 305 continue to operate according to the previously described sequence. The salination loop priming procedure is concluded when the air bubbles have passed bubble detector 608 and the conductivity reading observed at conductivity sensor 613 indicates that the desired physiologic sodium concentration level in the solution has been reached. In any embodiment, air from the sodium chloride cartridge 203 can be removed by the degassing module 705, trapped, and exhausted from the fluid circuit through vent port 517 and vent control valve 410 during this sequence.

In the next step, a physiologic solution preparation can be performed 937. For example, the system can add a concentration of approximately 0.9% by weight of sodium chloride to the water that has been first purified by passing through the sorbent cartridge to produce a physiologically compatible solution for priming a hemodialysis system. A solution of this composition will be recognized by those of skill in the art as a physiologically compatible solution for contacting blood as part of a renal replacement therapy delivery process and is a solution commonly employed for priming a dialyzer and extracorporeal circuit and also as a solution for blood rinse back to a subject from the extracorporeal circuit at completion of a therapy session. For example, in an embodiment in accordance with FIG. 1, in order to mix a physiologic priming solution and store the physiologic solution in solution reservoir 201, fluid balance control pump 303 can be operated to move fluid from the fluid circuit to solution reservoir 201 while operating water intake pump 304 to pull water into the circuit at the same rate. The salination valve 406 can direct flow through the sodium chloride cartridge 203, and the salination pump 307 rate can be adjusted to a predetermined proportion of the water intake pump 304 rate to produce the desired solution sodium concentration while monitoring the conductivity of the mixed solution at conductivity sensor 613.

The rate of salination pump 307 can be adjusted according to the conductivity readings to maintain the desired solution sodium concentration, wherein the salination pump rate is the volumetric flow rate of fluid passing through the conditioning conduit flow path 115. In any embodiment, during this sequence the salination valve 406 can be periodically switched or positioned to direct flow through bicarbonate cartridge 204 to infuse a desired amount of bicarbonate buffer into the solution. The physiologic solution preparation can be continued until a predetermined volume of solution has been produced and reserved in solution reservoir 201. For example, the total volume of required physiologic solution can be determined as the sum of the priming volume of dialyzer 701, the priming volume of the extracorporeal flow path 100, and a blood rinse-back reserve volume to be used at the end of the therapy session, and a predetermined fluid bolus reserve volume. The fluid bolus reserve volume can be held in reserve as a physiological-compatible fluid bolus infusion reserve volume to return to the subject if needed during therapy, such as for treatment of episodic intradialytic hypotension. Optionally, an additional predetermined volume can be prepared and reserved as a flushing fluid for a dialyzer and/or an extracorporeal flow path in reservoir 201 if a volume for additional rinsing of a dialyzer or an extracorporeal flow path is needed, such as in the case where a contaminant such as residual sterilant from the dialyzer manufacturing process is to be rinsed from a dialyzer and/or extracorporeal circuit or flow path.

Then, a dialyzer loop priming procedure can be performed 938. For example, with reference to FIG. 1, in order to prime the remainder of the controlled compliant flow path and dialyzer, the water intake pump 304 and salination pump 307 can be stopped while bypass valve 407 is set to direct flow through the dialyzer and fluid balance control pump 303 operates to add solution volume from solution reservoir 201 back to the controlled compliant flow path 110 while dialysate pump 305 continues to operate. The trans-membrane pressure monitored by dialysate pressure sensors 606 and venous pressure 604 and fluid balance control pump 303 rate is controlled to ensure that the hollow fibers in the dialyzer 701 are not collapsed or damaged by exceeding their pressure capacity.

In any embodiment, the therapy solution can be infused during this process with bicarbonate and electrolytes (for example, potassium, magnesium, glucose or calcium) per a dialysate prescription by switching salination valve 406 to bicarbonate cartridge 204 flow path and operating the salination pump 307 to infuse bicarbonate from cartridge 204, and operating acid concentrate pump 306 to infuse electrolytes from cation concentrate reservoir 205 to the priming solution per the desired dialysate prescription. In any embodiment, sorbent cartridge 703 can remove the majority of bacteria and endotoxin from the solution as it passes through the sorbent cartridge. Residual bacterial and endotoxin are removed from the solution prior to entering the dialyzer by first passing through endotoxin retentive microbial filter 706 located in the fluid circuit prior to the dialyzer inlet 506. Air from the remainder of the controlled compliant flow path and dialyzer is trapped in degas module 705 and exhausted through vent port 517 and vent control valve 410 during this sequence. The dialyzer priming procedure can continue for a predetermined time and until air bubbles are not observed at bubble detector 608, indicating that the controlled compliant flow path is completely filled.

In the next step, a venous loop priming procedure can be performed 939. The physiologically compatible solution that has been passed into the dialyzer by the preceding steps can first be purified by passing the fluid through the sorbent cartridge wherein a physiologically compatible level of at least sodium chloride, for example approximately 0.9% by weight, has been added to the purified water. The solution can then be passed through a microbial filter 706 for removal of residual microbial contamination from the solution. When the solution flows through the dialyzer membrane to the blood, the dialyzer membrane 702 can serve as a final, redundant microbial filter. Thus, a physiologically compatible solution for contacting blood having a necessary microbiological purity is unexpectedly provided from potable or tap water by the present invention. For example, in an embodiment in accordance with FIG. 1, the pumps and valves in the dialysate loop can continue to operate as described in the previous sequence moving solution from the solution reservoir 201 to the controlled compliant volume fluid path of controlled compliant flow path 110 which is now filled, thus causing the solution to further back filter across the dialysis membrane 702 from the dialysate compartment to the blood compartment. In any embodiment, the dialyzer membrane 702 provides a redundant barrier to prevent bacteria and endotoxin from entering the blood compartment during priming of the extracorporeal flow path.

As the pumps and valves of the dialysate loop continue to operate in the manner described, arterial pinch valve 402 remains closed and venous pinch valve 401 is opened. Referring also to FIG. 4A, this action allows solution to fill the lumen of venous line 105 and displace the air out through venous connector 501 to an overflow bag 210 attached through a tee fitting 550 at the junction between arterial line connector 502 and venous line connector 501. In the case of the alternative configuration shown in FIG. 4B, this action allows solution to fill the lumen of venous line 105 and displace air out of a hydrophobic vent membrane 560 at the junction of arterial line connector 502 and venous line connector 501. In the further case of alternative configuration shown in FIG. 4C, this action allows solution to fill the lumen of venous line 105 and displace air out through connector 501 into overflow bag 210. This process continues until a volume of fluid sufficient to displace the internal volume of venous line 105 and any desired additional flush volume has been pumped and no further bubbles are being detected at air-fluid (bubble) detector 603. Then venous pinch valve 401 is closed. Alternatively, in the example shown in FIG. 4, the operation can be continued until the pressure reading increase at venous pressure sensor 604 indicates that the venous line 105 has been filled and no further air is detected by venous bubble detector 603.

Next, an arterial loop priming procedure can be performed 940 as described in FIG. 11. For example, in an embodiment corresponding to FIG. 1, as the dialysate loop pumps and valves continue to operate in the manner described in the previous step, arterial pinch valve 402 is now opened and blood pump 302 is operated in reverse first to complete filling of the dialyzer blood compartment and finally arterial line 102. Referring also to FIG. 4A, this action allows solution to fill the lumen of arterial line 102 and displace the air out through arterial connector 502 to an overflow bag 210 attached through a tee fitting 550 at the junction between arterial line connector 502 and venous line connector 501. In the case of the alternative configuration shown in FIG. 4B, this action allows solution to fill the lumen of arterial line 102 and displace air out of a hydrophobic vent membrane 560 at the junction of arterial line connector 502 and venous line connector 501. In the further case of alternative configuration shown in FIG. 4C, this action allows solution to fill the lumen of arterial line 102 and displace air out through connector 502 into overflow bag 210.

Blood pump 302 continues to operate until the desired volume of fluid has been pumped through arterial line 102 and no further bubbles are detected at arterial bubble detector 601. Then the arterial pinch valve 402 is closed. Alternatively, in any embodiment blood pump 302 can be operated until the pressure reading increase at arterial pressure sensor 602 indicates that the arterial line 102 has been filled and no further air is detected by arterial bubble detector 601, at which time the system stops all pumps and maintains arterial pinch valve 402 and venous pinch valve 401 in the closed position.

In an alternative configuration shown in FIG. 4C, blood pump 302 can be operated to recirculate the solution that has filled extracorporeal circuit 100 by the actions of steps 938, 939 and 940 for a predetermined time through the dialyzer and extracorporeal circuit to rinse contaminants from the dialyzer and extracorporeal circuit such as residual sterilant or particulate residue that can be present in certain commercially available dialyzers and extracorporeal circuits. Following a predetermined recirculation, a volume for additional rinsing of a dialyzer or an extracorporeal flow path can be conveyed from reservoir 201 through the controlled compliant flow path to flush the contaminants and contaminated solution to overflow bag 210.

Then, the system can confirm that the hemodialysis device is prepared for a therapy session 941. For example, the user interface can display a message to notify the user that priming is complete and system is ready for a therapy session.

During steps 938, 939 and 940 the minimum volume of solution required to fill the blood compartment of the dialyzer and the extracorporeal circuit 100 can be referred to as the void volume or a priming volume of the extracorporeal flow path.

Figure 12:
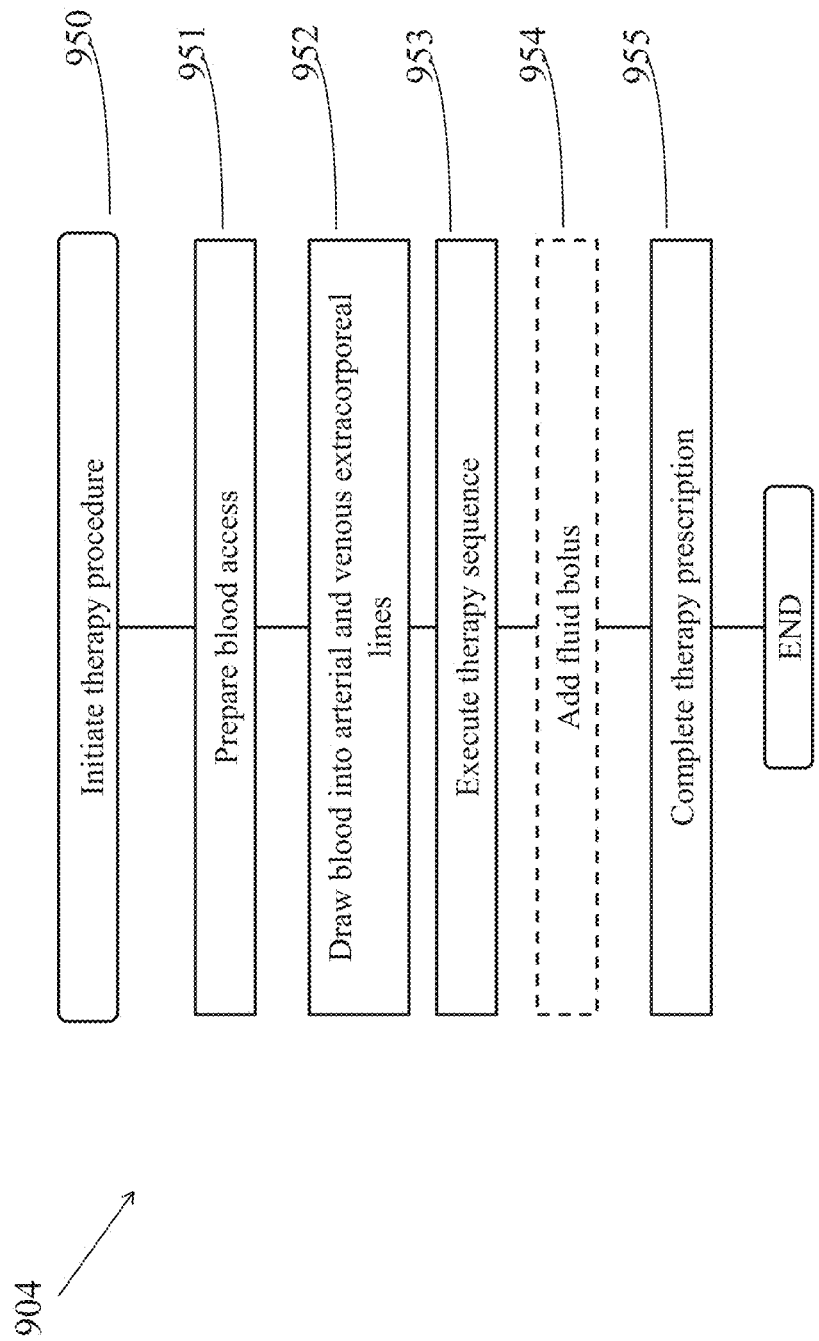
FIG. 12 shows a method of performing therapy using a hemodialysis device in certain embodiments.

FIG. 12 shows a therapy procedure 904 in accordance with the invention. The user can initiate the therapy procedure 950 by preparing blood access 951 per the patient's normal blood access preparation procedure. Then, blood can be drawn into the arterial and venous lines of an extracorporeal flow path 952. For example, in an embodiment shown in FIGS. 1, and 4A, 4B or 4C, the user can separate the arterial line connector 502 from the priming connection and connects arterial line 102 of the extracorporeal flow path 100 to the arterial blood access 104 at arterial line connector 502. The user can then prompt the hemodialysis device through user interface 801 to start blood flow.

Blood pump 302 can be operated with the arterial pinch valve 402 and venous pinch valve 401 open. Blood displaces the priming solution in extracorporeal flow path 100, first through arterial line 102, next through dialyzer 701, and then out through the venous line at 501 into overflow reservoir 210. Blood pump 302 stops when a volume of fluid approximately equal to the internal volume of the extracorporeal flow path has been displaced into priming overflow reservoir 210 by the pumped blood. Alternatively, the displaced priming solution can be discharged into a suitable container or a drain. The user can connect venous line 105 of extracorporeal flow path 100 to the patient's venous blood access line 103 at connector 501.

Alternatively, in any embodiment all of the priming solution can be retained in the system without requiring an overflow bag or discharge into a collection container. For example, the user can separate venous line 105 of extracorporeal flow path 100 from tee fitting 550 of the priming overflow reservoir 210 or, in some embodiments, from hydrophobic vent 560, and connects patient's venous blood access 103 at connector 501. The user further can prompt the system through the user interface to start venous blood flow. The system can open venous pinch valve 401 and switches valve 407 to bypass mode or, in some embodiments, close degassing vent control valve 410 to prevent air from being drawn into the system by sub-atmospheric pressure in controlled compliant flow path 110 through port 517 and the hydrophobic vent membrane of degassing module 705. Fluid balance control pump 303 can be operated to pull the priming solution across dialysis membrane 702 from the blood compartment to the dialysate compartment and into solution reservoir 201. Fluid control pump 303 continues to operate until a predetermined volume of solution approximately equal to the internal volume of venous line 105 has pumped across dialysis membrane 702 to solution reservoir 201. Then fluid control pump 303 stops and venous pinch valve 401 closes.

Next in any embodiment wherein all of the priming solution can be retained in the system without requiring an overflow bag or discharge into a collection container, the user interface 801 can prompt the user to connect arterial line 102 of extracorporeal flow path 100 to the arterial line 104 of the patient's blood access at connector 502, and the user can connect arterial line 102 of extracorporeal flow path 100 to the arterial connector of the patient's blood access line 104 at connector 502. In any embodiment, the user can confirm through user interface 801 that the arterial blood access is connected. The system can open arterial pinch valve 402 and start blood pump 302 and fluid balance control pump 303 at equal pumping rates to displace a volume of solution approximately equal to the sum of the internal volumes of arterial line 102 and dialyzer 701 blood compartment across dialysis membrane 702 and into the solution reservoir 201. Then the fluid balance control pump 303 can be stopped and venous pinch valve 401 opened to allow blood pump 302 to pump blood through the complete extracorporeal flow path and back to the subject through venous blood access line 103.

In the next step, a therapy sequence can be executed 953. For example, a therapy process control algorithm can be executed to accomplish the dialysis prescription as follows:

The dialysate pump 305, the blood pump 302 and the heparin pump 301 each can be operated at their respective prescribed flow rates. Dialysate temperature can be controlled by heater 708 in closed loop with temperature measurements from a temperature sensor, such as sensor 612, or any appropriate location in controlled compliant flow path 110. In certain embodiments, the acid concentrate pump 306 can be operated at a controlled ratio to the dialysate flow rate to infuse the dialysate with the proper concentration of cations, such as $K^+$, $Mg^{++}$, $Ca^{++}$ from cation concentrate reservoir 205. Other solutes, for example glucose and/or acetic acid, may also be included in the cation concentrate in reservoir 205 as per the dialysis prescription, and thereby added at the prescribed concentration to the dialysate by this means, and salination valve 406 can be operated to direct flow through bicarbonate cartridge 204 and the salination pump 307 is operated at a controlled rate to infuse the dialysate with the prescribed level of bicarbonate buffer. Control of the dialysate sodium level can be accomplished by sensing conductivity at conductivity sensor 613 and operating water pump 304 to add water to reduce sodium level or, alternatively, switching salination valve 406 to direct flow through sodium chloride cartridge 203 and operating salination pump 307 to infuse sodium chloride concentrate into the dialysate to increase the sodium level, while control of the patient fluid removal rate is accomplished by controlling the fluid balance control pump 303. When the control pump 303 withdraws fluid volume from the controlled volume controlled compliant flow path 110 to the solution reservoir 201 in excess of the volumes added by pumps 304 and 306 a volume of fluid equal to the excess amount is drawn from the patient's blood across dialysis membrane 702 to controlled compliant flow path 110.

Because the controlled compliant flow path 110 has a fixed volume, net fluid removal is controlled and determined according to the following formula:

Patient Fluid Balance+Fluid Balance Control Pump+
Water Pump+Acid Conc. pump $\Sigma_{i=0}^{n} X_i = 0$ One skilled in the art will recognize that both constant and varying profiles of patient ultrafiltration rate and dialysate sodium levels can be accomplished through this algorithm. As provided herein, the term X refers to the volumetric flow rate of a pump where the number of pumps can range for n from 0 to 20. The term "n from 0 to 20" means any integer value of 0, 1, 2, 3, 4, 5, 6, 7, 8, 9, 10, 11, 12, 13, 14, 15, 16, 17, 18, 19, or 20.

In any embodiment, a fluid bolus can optionally be added 955. For example, in an embodiment in accordance with FIG. 1, the user may request a fluid bolus through user interface 801. Fluid bolus is provided to the subject at a controlled rate and to a controlled total volume by changing the rate of fluid balance control pump 303 such that net fluid is added to controlled compliant flow path 110 from control reservoir 201 according to the preceding formula. Because controlled compliant flow path 110 has a substantially inflexible void volume, any net fluid added to controlled compliant flow path 110 will be passed across dialysis membrane 702 to the blood compartment and the patient. Check valve 403 ensures that any fluid added to controlled compliant flow path 110 cannot enter the dialyzer through port 507, but rather, the bolus solution is forced to travel only toward the sorbent cartridge 703 and is purified by first flowing through sorbent cartridge 703, gas bubbles are removed by flowing through degassing module 705 and then through microbial filter 706 before passing into the dialyzer. Finally, the fluid can first pass through the dialyzer membrane before contacting the blood, with the dialyzer membrane serving as a redundant filtration step to ensure microbial purity of the fluid volume passing to the blood.

In other embodiments, such as the system for hemofiltration shown in FIG. 1D and the system for hemodiafiltration shown in FIG. 1E, a physiologically compatible solution for infusion to a subject is produced by passing the fluid exiting microbial filter 706 through an additional microbial filter 709 that can act as a redundant filtration step to ensure microbial purity of the fluid before it enters extracorporeal circuit 100 at port 538 and is passed to the subject.

The sodium level can be assessed by monitoring conductivity at sensor 613 and if the sodium level of the bolus solution deviates from the desired value, the solution is sent through bypass flow path 111 by valve 407 and circulated until the sodium level is adjusted by either adding water from reservoir 202 through water pump 304 to lower sodium concentration in the bolus solution by dilution, or by infusing sodium through sodium chloride cartridge 203 to increase sodium concentration in the bolus solution. In any embodiment, the bolus fluid can be re-infused with electrolytes by cation concentrate from reservoir 205 metered by acid concentrate pump 306. The solution is further filtered through microbial filter 706 to remove residual microorganisms and endotoxin, and next across dialysis membrane 702 to the blood compartment and to the patient. In any embodiment, dialysis membrane 702 provides a redundant microbiological barrier between the dialysate compartment and the blood compartment.

The therapy process continues until the dialysis prescription is completed 955. Alternatively, the user can request to end the therapy process. If therapy is successfully completed per the dialysis prescription, the system can provide notification through user interface 801 that the therapy session is completed.

Figure 13:
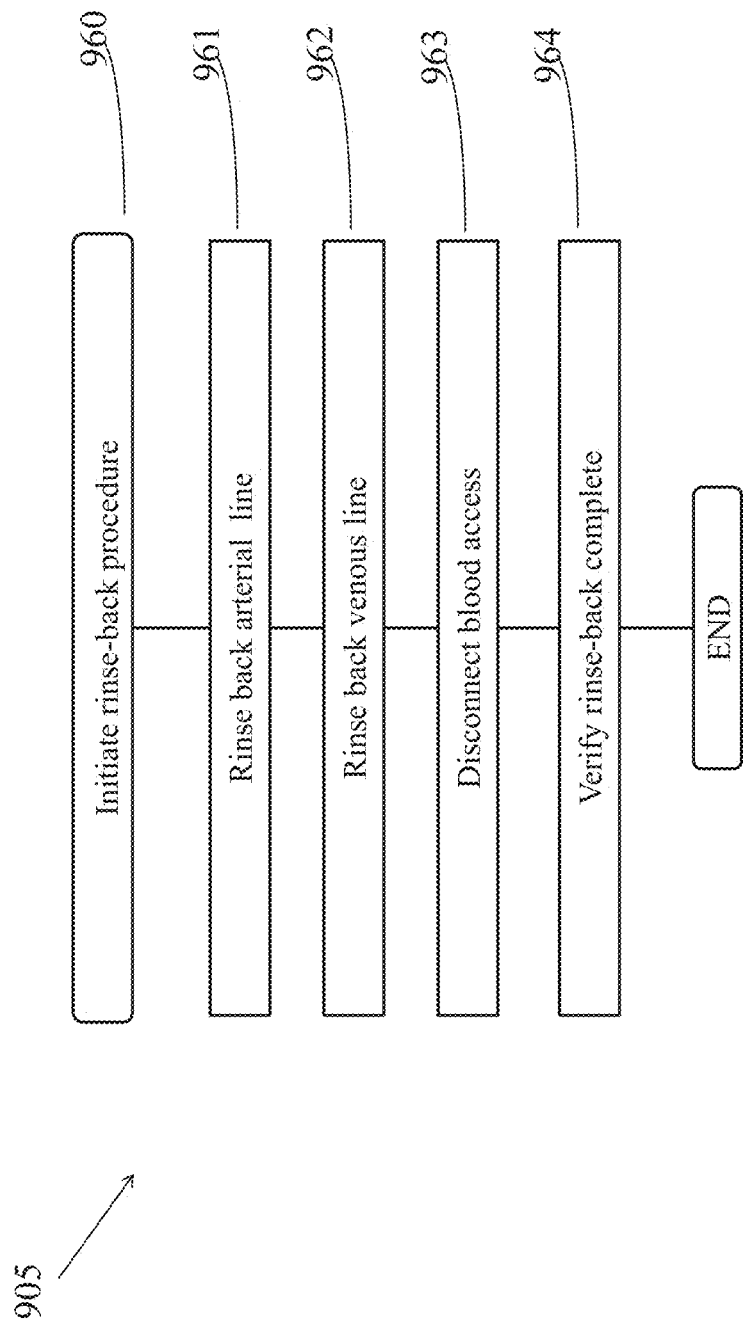
FIG. 13 shows a method of rinsing blood back using a hemodialysis device in accordance with certain embodiments.

FIG. 13 shows a blood rinse-back procedure 905 in accordance with the invention. The user can initiate the rinse-back procedure 960, for example, by entering a request through the user interface for blood rinse back or blood rinse back can begin automatically at the conclusion of a therapy session. Through operations as described in preceding steps, the fluid in the controlled compliant flow loop 110 and reservoir 201 can be comprised of filtrate from the blood of the subject and a physiologically compatible solution that has been has been first purified by passing through the sorbent cartridge that has a physiologically compatible level of at least sodium chloride, for example approximately 140 mEq/L. Before entering the dialyzer, the fluid is further passed through microbial filter 706 for removal of residual microbial contamination from the fluid. When the solution is further passed through the dialyzer membrane to the blood, the dialyzer membrane serves as a final, redundant microbial filter. Thus, a physiologically compatible solution for blood rinse back to a subject can be provided with necessary microbiological purity. In any embodiment, the user can control the sequence of arterial line 102 and venous line 105 rinse back by selecting through user interface 801 which line to rinse back first. Then, the arterial line can be rinsed back 961. For example, in an embodiment corresponding to FIGS. 1 and 2, blood can be rinsed back to the patient from arterial line 102 by operating the fluid control pump 303 to add fluid back to controlled compliant flow path 110 from solution reservoir 201 to cause solution to move from the controlled compliant flow path 110 across dialysis membrane 702 to the blood compartment. Venous pinch valve 401 can be closed and blood pump 302 is operated in reverse direction at the same rate as fluid control pump 303 is adding solution to controlled compliant flow path 110. In this manner, a solution volume sufficient to rinse the volume of blood from the blood compartment of dialyzer 701 and arterial line 102 back to the patient is pumped and then fluid balance control pump 303 and blood pump 302 are stopped. In any embodiment, the user can prompt through the user interface to return an additional increment of fluid for further rinse back of arterial line 102, or acknowledge that arterial line 102 is sufficiently rinsed back. When the user confirms through user interface 801 that arterial line 102 is sufficiently rinsed back, arterial pinch valve 402 closes to prevent further fluid ingress or egress through arterial blood access line 104.

Next, the venous line can be rinsed back 962 as described in FIG. 13. Blood can be rinsed back to the patient from the venous line by operating fluid balance control pump 303 in an embodiment corresponding to FIGS. 1 and 2 to add solution back to controlled compliant flow path 110 from solution reservoir 201 to cause solution to move from the controlled compliant flow path 110 across dialysis membrane 702 to the blood compartment. Venous pinch valve 401 is opened to allow the solution to push the blood out of the venous line 105 to the patient. Fluid balance control pump 303 continues to operate until a fluid volume sufficient to rinse the blood volume from venous line 105 back to the patient has been pumped and then fluid balance control pump 303 is stopped. In any embodiment, the user can enter prompts through user interface 801 to return additional increments of solution for further rinse back of venous line 105, or acknowledge that venous line 105 is sufficiently rinsed back. When the user acknowledges that venous line 105 is sufficiently rinsed back, venous pinch valve 401 closes to prevent further fluid ingress or egress through venous blood access line 103.

In the next step, the user can disconnect the blood access 963, for example by disconnecting patient blood access lines 103 and 104 from connection ports 501 and 502 of extracorporeal flow path 100 per the patient's normal blood access procedures. Then, the user can verify the rinse-back is complete 964. For example, in any embodiment the user can communicate via user interface 801 that patient's blood access disconnection has been completed.

Figure 14:
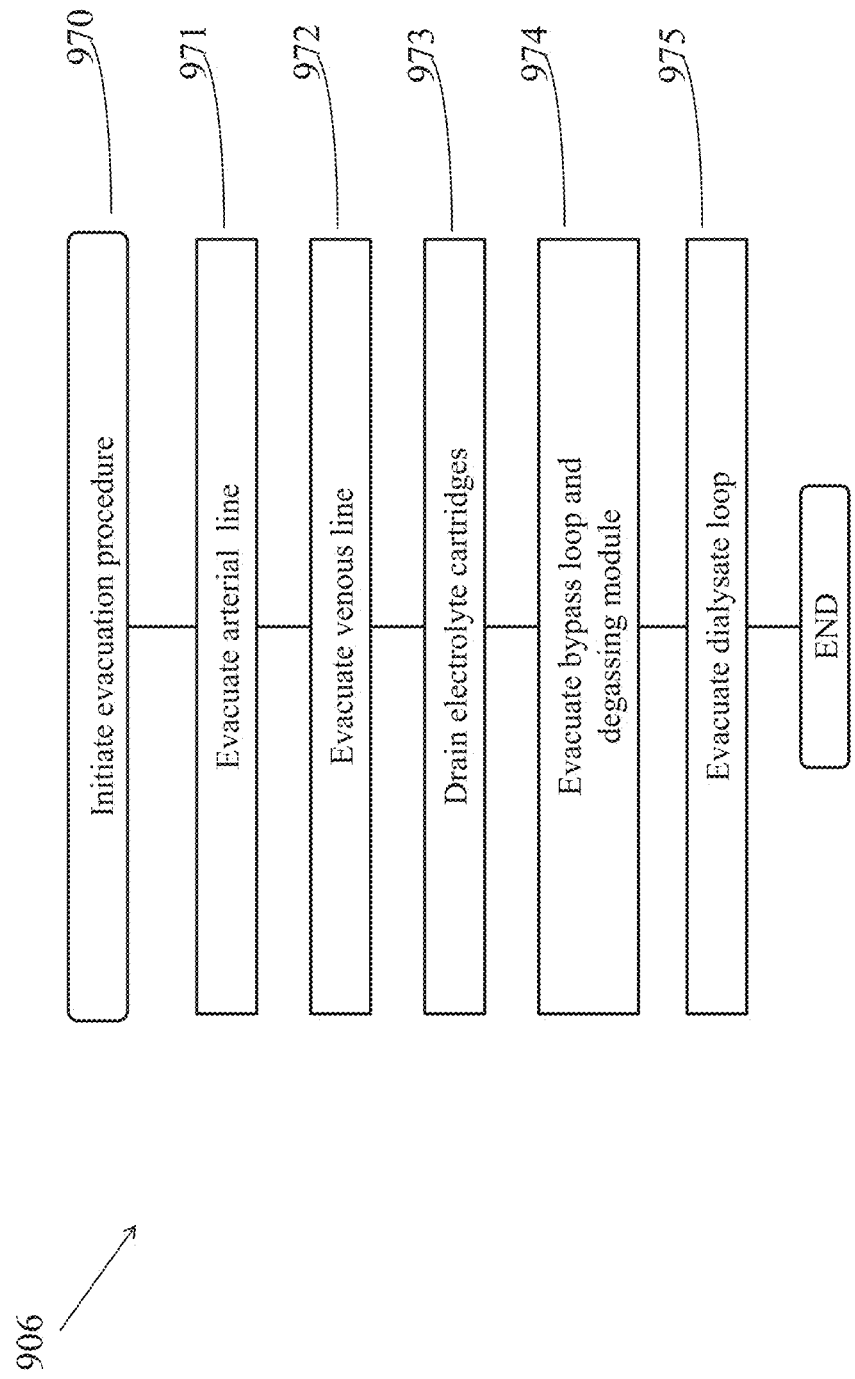
FIG. 14 shows a method of evacuating a hemodialysis device in accordance with certain embodiments.

FIG. 14 shows an evacuation procedure 906 in accordance with the invention. For ease of shutdown and disposal, evacuation procedure 970 can move fluid volume remaining in the system to a reservoir, for example reservoir 201. The fluid volumes moved can include fluid volume from an extracorporeal flow path, consisting of solution that remains in the extracorporeal circuit 100 after the blood has been rinsed back; fluid volume from an infusate reservoir, consisting of solution that remains in an infusate reservoir at the end of a therapy session such as fluid remaining in reservoir 205; fluid volume removed from a conditioning conduit flow path, such as fluid remaining at the end of a therapy session in conditioning conduit flow path 115; fluid volume removed from a bypass conduit, such as fluid volume remaining in bypass flow path 111; and fluid volume removed from a solution flow conduit, including flow paths such as 110 or 120. The evacuation procedure can be initiated 970, for example, by the user entering a request through the user interface. First, the arterial line can be evacuated 971. For example, the system can remove the rinse back solution from arterial line 102 by opening arterial pinch valve 402 and operating blood pump 302 and fluid control pump 303 toward solution reservoir 201 to move the solution from arterial line 102 across dialysis membrane 702 to controlled compliant flow path 110 and into solution reservoir 201. Arterial pinch valve 402 can be closed and blood pump 302 stopped when a solution volume sufficient to drain arterial line 102 has been pumped.

Next, the venous line can be evacuated 972. For example, the system can remove the rinse back solution from venous line 105, dialyzer 701, microbial filter 706, and the portion of controlled compliant flow path 110 from dialyzer inlet 506 to degassing module outlet 519 by opening venous pinch valve 401, closing degassing vent valve 410, and operating dialysate pump 305 in the reverse direction. Fluid balance control pump 303 continues to remove fluid from controlled compliant flow path 110 into solution reservoir 201 during this step. Pumping continues until a volume of fluid sufficient to drain this portion of the fluid circuit has been moved to solution reservoir 201 and then dialysate pump 305 is stopped. Control pump 303 continues to operate in the efflux direction and fluid in the portion of controlled compliant flow path 110 between dialyzer outlet 507 and control pump 303 is moved to reservoir 201, and then venous pinch valve 401 is closed and valve 407 is positioned to bypass flow path 111. With control pump 303 continuing to operate in the efflux direction, vent valve 410 is opened to drain the degassing module 705 and that portion of the controlled compliant flow path 110 from degassing module outlet 519 to bypass valve 407. Pumping continues until a volume of fluid sufficient to drain this portion of the fluid circuit has been moved to solution reservoir 201.

Then, in the next step, electrolyte cartridges can be drained 973. For example, the sodium chloride cartridge 203, bicarbonate cartridge 204, and connecting lines can be drained to a void volume created within main controlled compliant flow path 110 by the preceding step. To accomplish this, fluid balance control pump 303 is stopped, bypass valve 407 is positioned or switched back to dialyzer inlet flow path, degassing vent valve 410 is opened, venous pinch valve 401 is opened, and salination pump 307 operates in reverse direction while the salination valve is directed alternately between sodium chloride cartridge 203 flow path and bicarbonate cartridge 204 flow path. This action moves the fluid to temporary storage created in degassing module 705 and controlled compliant flow path 110 by previous actions. When a volume of fluid sufficient to drain both cartridges and the conditioning flow path 115 lines has been pumped to degas module 705 and main controlled compliant flow path 110, salination pump 307 is stopped.

In the next step, the bypass loop and degassing module can be evacuated 974. For example, with reference to FIG. 1, the portion of controlled compliant flow path 110 between degassing module 705 outlet 519 and dialyzer 701 can be drained by operating dialysate pump 305 in reverse with venous pinch valve 401 remaining open, vent valve 410 closed, and control pump 303 operating in an efflux direction until a volume sufficient to drain the volume of fluid re-introduced to that portion of controlled compliant flow path 110 by the preceding drainage of sodium chloride cartridge 203 and bicarbonate cartridge 204 has been removed to control reservoir 201. Then dialysate pump 305 is stopped, venous pinch valve 401 is closed and bypass valve 407 is positioned or switched to direct flow through bypass flow path 111 and degassing vent valve 410 is opened with control pump 303 continuing to operate in the efflux direction. Fluid balance control pump 303 operates to move fluid to therapy solution reservoir 201 until a volume of fluid sufficient to drain degassing module 705, the portion of the controlled compliant flow path 110 from degassing module outlet 519 to valve 407, and priming and recirculation bypass flow path 111 has been moved to solution reservoir 201.

Then, the dialysate loop can be drained 975. For example, with reference to FIG. 1, the remainder of controlled compliant flow path 110 can be drained. Dialysate pump 305 can be operated in reverse with vent valve 410 open and fluid balance control pump 303 operating in the efflux direction to move fluid remaining in controlled compliant flow path 110 between degassing module 705 inlet 516 and fluid balance control pump 303 to solution reservoir 201. Finally, all pumps are stopped and the degassing vent control valve 410 is closed. In any embodiment, the user interface can display a message to the user that the evacuation procedure is complete, and that therapy cassette 820 may be removed and replaced with cleaning manifold 840. It will be recognized from the detailed description of this invention that solution reservoir 201 functions as a common reservoir of solution or fluid volume used for multiple purposes and originating from multiple sources or locations within the system. The reservoir may contain any one of a dialysate, a filtrate, a volume of a physiologically compatible priming solution, a volume of a physiologically compatible solution to provide a bolus of fluid to a subject receiving treatment, a volume of physiologically compatible solution to provide solution for return of blood from an extracorporeal flow path to a subject receiving treatment, a volume of solution returned to the common reservoir from an extracorporeal flow path when blood from a subject is introduced to the extracorporeal flow path, and combinations thereof. Solution reservoir 201 further can receive fluids that are drained from the extracorporeal flow path, the controlled compliant flow path, and/or an infusate reservoir following conclusion of a treatment.

Figure 15:
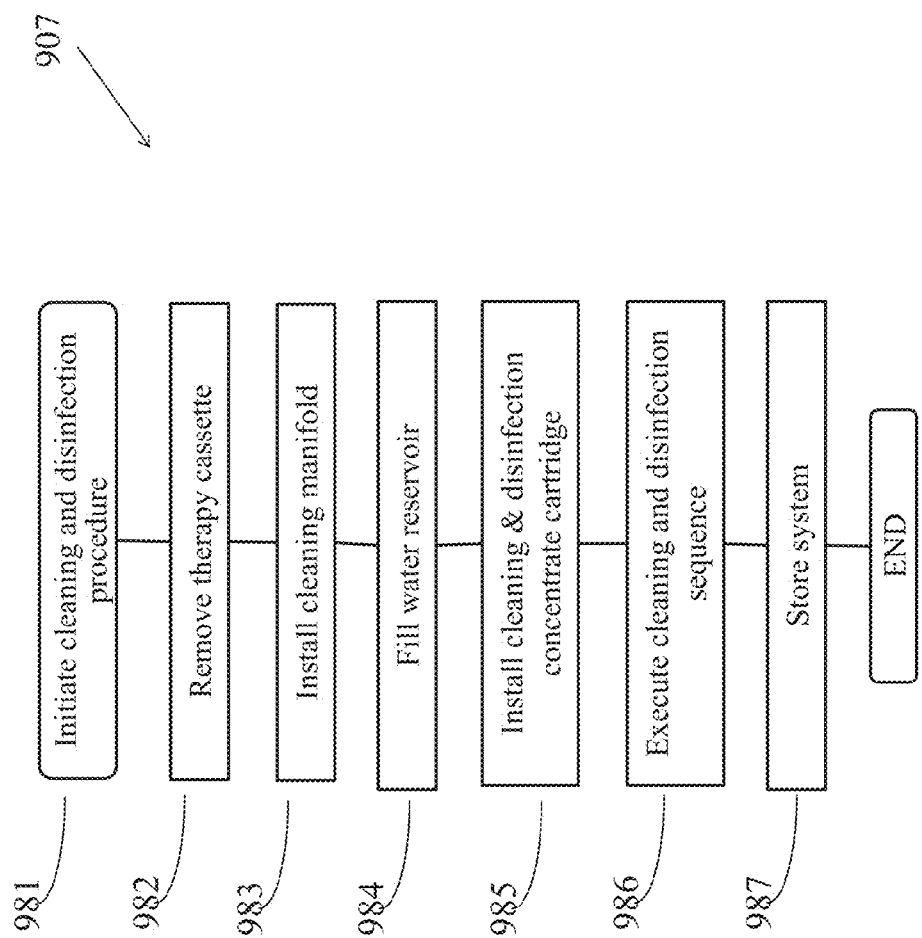
FIG. 15 shows a method of cleaning and disinfecting a hemodialysis device in certain embodiments.

FIG. 15 shows a cleaning and disinfection procedure 907 in accordance with the invention. The cleaning and disinfection procedure can be initiated 981, for example, by the user acknowledging through user interface the user's intent to remove the disposable and consumable components, optionally grouped into a therapy cassette. In the next step, the user can remove the therapy cassette 982. For example, in an embodiment corresponding to FIGS. 1, 5G, 6A and 6B, arterial pinch valve 402 and venous pinch valve 401 can be opened to allow arterial line 102 and venous line 105 to be disengaged for cassette removal, and the user can remove the therapy cassette. Then, the user can install a cleaning manifold 983. For example, the user can remove the therapy cassette 820 and install cleaning manifold 840 in place of therapy cassette 820 on the system. In any embodiment, sensors can be activated to confirm correct loading of the cleaning manifold. In any embodiment, the system may optionally communicate through visual, audible, or tactile signals to user during the process to confirm successful task completion, or to provide corrective feedback.

In the next step, a water reservoir can be filled. For example, the system can display a message on the user interface 801 to prompt the user to fill water reservoir 202 with sufficient water, including potable water, to execute the cleaning and disinfection cycle. It is noted the system is not limited to potable water but can include other types of water prepared and/or treated by those of ordinary skill in the art suitable for use in the present dialysis systems and methods contemplated by the present invention including peritoneal dialysis, hemodiafiltration and hemodialysis. The required amount of water can further be displayed on the user interface. In any embodiment, water reservoir 202 can include a visual indicator of the minimum fill level for this process. The user can fill water reservoir 202 and reconnect it to cleaning manifold 820 connection ports 509BM and 510BM. Alternatively, in any embodiment, the user can transport water or potable water to water reservoir 202 and fill it in place on the system. In some embodiments, sensors can be activated to confirm correct filling and reconnection of the water reservoir.

In any embodiment, the system can intake and degas water from the water reservoir 202 according to the same procedure as previously described under the de-aeration procedure described herein. With reference to FIG. 3, the system can purify water from water reservoir 202 by passing the water through the sorbent cartridge 703 while the pumps and valves are sequenced to flush clean water through each fluid circuit component to the integral fluid reservoir contained in the cleaning manifold in order to flush residual therapy solutions from controlled compliant flow path 110, the conditioning flow path 115 through pump 307 and valve 406, bypass flow path 111, which can function in the present embodiment to bypass the dialyzer, and also metering pumps 303, 304, and 306 prior to further cleaning and/or disinfection.

In the next step, a cleaning and/or disinfection concentrate cartridge is installed 985. For example, the user interface 801 can prompt the user to remove sorbent cartridge 703 and connect the cleaning and/or disinfection concentrate cartridge 720 into the controlled compliant flow path in place of sorbent cartridge 703 at connection ports 513 and 514. The user can acknowledge through user interface 801 that the cleaning and/or disinfection concentrate cartridge 720 is installed. In any embodiment, sensors can be activated to confirm correct connection of the cleaning solution concentrate cartridge.

In the next step, a cleaning and/or disinfection sequence can be executed 986. For example, the user can enter a prompt through user interface 801 to start an automated cleaning and/or disinfection cycle. After this action, the user may not be required to be present for the remainder of the process. The system can first circulate the water contained in the controlled compliant flow path and jumper lumens of the cleaning reservoir in a recirculating loop through the cleaning and/or disinfection solution concentrate cartridge by operating the pumps and valves of controlled compliant flow path 110 to mix and distribute the cleaning and/or disinfection solution concentrate uniformly through all fluid pathways. The system heater 708 can heat the circulating cleaning and/or disinfection solution to a sufficient temperature to clean and disinfect the fluid circuit while continuing to operate the pumps and valves to circulate the cleaning and/or disinfection solution through all fluid pathways until the disinfection process temperature is reached. The fluid temperature is monitored at control points to confirm that the solution has reached the required disinfection temperature throughout the fluid circuit. The system continues to monitor and control the fluid at the required disinfection temperature while operating the pumps and valves to circulate the heated cleaning and/or disinfection solution through all fluid pathways until the required time at temperature is completed. When the cleaning and/or disinfection cycle has been completed, the heater and system pumps can be shut down. Optionally, the pumps can continue to run briefly following heater shutdown to allow residual heat to be safely dissipated from the heater.

In the next step, the hemodialysis system or device can be stored 987. For example, in an embodiment corresponding to FIG. 6B, the cleaning and/or disinfection solution can remain in the fluid circuit and the cleaning manifold 840 can be left in place on the system until the system is needed for the next therapy session. In any embodiment, the hemodialysis device can be folded into the storage and transport configuration with the fluid circuit filled with the cleaning and/or disinfection solution and the cleaning manifold in place to ensure that contamination is not introduced to the fluid pathways prior to the next use.

The FIGS. and specific examples provided herein illustrate a possible embodiment of the invention and are non-limiting with respect to the specific physical geometries of the various components depicted in the illustrations. It will be apparent to one skilled in the art that various combinations and/or modifications can be made in the systems and methods described herein depending upon the specific needs for operation. Moreover, features illustrated or described as being part of one embodiment may be used on another embodiment to yield a still further embodiment.

We claim:

1. A system for generating a physiologically compatible fluid, comprising:
    a conditioning flow path having at least a salination valve, and at least one salination pump, and at least one container having at least one solute in excess of the solubility of that solute wherein at least one of the solutes is a buffer source or sodium chloride;
    said conditioning flow path in fluid communication with a controlled compliant flow path connected to a dialyzer inlet and a dialyzer outlet and comprising a sorbent cartridge, wherein the conditioning flow path can selectively meter fluid into and out of the controlled compliant flow path, wherein fluid enters the conditioning flow path from the controlled compliant flow path through a conditioning flow path inlet; and exits the conditioning flow path to the controlled compliant flow path through a conditioning flow path outlet; and wherein the conditioning flow path inlet is positioned in the controlled compliant flow path downstream from the conditioning flow path outlet.

2. The system of claim 1, further comprising an extracorporeal flow path fluidly connected to the dialyzer, wherein the controlled compliant flow path modifies water into any one of a solution for priming an extracorporeal circuit, rinsing or flushing the dialyzer and blood flow conduits, a physiologically compatible solution for contacting blood, a physiologically compatible solution for bolus infusion to a subject, and a solution for blood rinse back to a subject.

3. The system of claim 1, wherein selectively metering in and metering out fluid from the controlled compliant flow path generates a physiologically compatible level of a sodium ion and/or a buffer from the at least one container in the conditioning flow path.

4. The system of claim 1, further comprising a sodium chloride container and a buffer source container.

5. The system of claim 4, wherein the conduits and containers of the conditioning flow path are controlled compliant.

6. The system of claim 4, wherein the sodium chloride and the buffer source are dry compositions, the dry compositions being hydrated by circulating a fluid through the conditioning flow path.

7. The system of claim 1, wherein a means for selectively metering fluid into and out of the controlled compliant flow path is a fluid balance control pump in fluid communication with the controlled compliant flow path and a fluid reservoir.

8. The system of claim 7, wherein a means for selectively metering fluid into and out of the controlled compliant flow path is any one of a control pump, a water pump, a salination pump, an acid concentrate pump, a replacement fluid pump, and combinations thereof.

9. The system of claim 1, wherein the controlled compliant flow path has at least one pump or valve in fluid communication with both a conduit of the controlled compliant flow path and a container; and
    a pump in fluid communication with a conduit of the controlled compliant flow path and a water source.

10. The system of claim 4, further comprising at least one pump or valve in fluid communication with a conduit of the controlled compliant flow path and at least a buffer source or a sodium source, a pump in fluid communication with a conduit of the controlled compliant flow path and a water source.

11. The system of claim 4, wherein fluid passing through the sodium chloride container increases the sodium chloride concentration of the fluid and fluid passing through the buffer source container increases the buffer concentration of the fluid.

12. The system of claim 4, wherein the sodium chloride container, the buffer source container and the salination valve are configured into a consumables cartridge.

13. The system of claim 4, wherein the sodium chloride and the buffer source are contained in separate compartments of a common container or cartridge.

14. The system of claim 13, wherein the sodium compartment and the buffer source compartment share a common fluid inlet port or a common fluid outlet port.

15. The system of claim 4, wherein a container is disposable.

16. The system of claim 4, wherein a container is reusable and refilled or replenished with sodium chloride or a buffer source.

17. The system of claim 4, wherein a sodium chloride container or a buffer source container are configured together with any of an extracorporeal circuit, a dialyzer, a degassing module, a cation concentrate reservoir, a control reservoir, a sorbent container, a cleaning and/or disinfection concentrate, or an ammonia sensing module into a therapy cassette.

18. The system of claim 4, wherein the salination valve is located downstream from the sodium chloride container and the buffer source container and the salination pump is located upstream from the sodium chloride container and the buffer source container.

19. The system of claim 4, wherein the salination valve is located upstream from the sodium chloride container and the buffer source container and the salination pump is located downstream from the sodium chloride container and the buffer source container.

20. The system of claim 4, wherein fluid flow through the sodium chloride container and the buffer source container can occur concurrently.

21. The system of claim 4, wherein the controlled compliant flow path is fluidly connected to a source selected from the group consisting of a potable water source, a tap water source, a bottled water source, a purified water source and combinations thereof, a physiologically compatible solution source, a dialysate source, a filtrate source, or a replacement fluid source; and wherein a portion of the fluid entering a container is water selected from any one of potable water, tap water, bottled water, purified water and combinations thereof, a physiologically compatible solution, a dialysate, a filtrate, or a replacement fluid.

22. The system of claim 4, further comprising a sorbent system, and wherein a portion of the fluid entering a container is water that has been purified through the sorbent system.

23. The system of claim 4, wherein the sodium chloride container contains a first dry composition and the buffer source container contains a second dry composition, the first and second dry compositions are hydrated during circulation of fluid through the conditioning flow path and the quantity of the dry compositions provided are in excess of the quantities required for operation wherein a portion of the dry compositions remains undissolved in the sodium chloride container and the buffer source container, the sodium chloride container and the buffer source container being operable such that a saturated solution exits the sodium chloride container and/or the buffer source container.

24. The system of claim 23, wherein a container has at least one fluid inlet port and at least one fluid outlet port, and filtering media at the inlet port and outlet port to prevent at least a portion of undissolved sodium chloride or undissolved buffer source from exiting the container.

25. The system of claim 4, wherein a consumables cartridge has a sodium chloride container, a buffer source container and a salination valve for controlling flow of fluid diverted from a conduit of the controlled compliant flow path through the sodium chloride container and the buffer source container.

26. The system of claim 4, wherein the salination valve controls the amount of a fluid flowing through the conditioning flow path into the sodium chloride container and the buffer source container before the fluid returns to the controlled compliant flow path.

27. The system of claim 4, wherein the salination valve directs a fluid through either the sodium chloride container, the sodium bicarbonate container, or both.

28. The system of claim 1, wherein a salination valve is a 2-way or a 3-way valve.

29. The system of claim 4, wherein either the sodium chloride container or the buffer source container is detachable from the conditioning flow path.

30. The system of claim 1, wherein the conditioning flow path is detachable from the controlled compliant flow path.

31. The system of claim 1, wherein the controlled compliant flow path further comprises a conductivity sensor and the system further comprises a controller to control the amount of fluid flow through a conditioning flow path, based at least in part on the conductivity of the fluid in the controlled compliant flow path.

32. The system of claim 1, wherein the conditioning flow path further comprises a temperature sensor, and the system further comprises a controller to control the rate of fluid flow through a conditioning flow path, based at least in part on the temperature of a fluid in the conditioning flow path.

33. The system of claim 1, further comprising
a common reservoir and a control pump in fluid communication with the conditioning flow path wherein the common reservoir contains any one of a dialysate, a filtrate, a volume of a physiologically compatible priming solution, a volume of a physiologically compatible solution to provide a bolus of fluid to a subject receiving treatment, a volume of physiologically compatible solution to provide solution for return of blood from an extracorporeal flow path to a subject receiving treatment, a volume of solution returned to the common reservoir from an extracorporeal flow path when blood from a subject is introduced to the extracorporeal flow path, and combinations thereof.

34. The system of claim 32, wherein a dialysate is produced by the system for performing hemodialysis or hemodiafiltration from water introduced to a conduit of the controlled compliant flow path, a sorbent system, the sodium chloride container, and optionally solutes other than sodium introduced to a conduit of the controlled compliant flow path.

35. The system of claim 32, wherein a volume of a physiologically compatible priming solution is produced by the system from water introduced to a conduit of the controlled compliant flow path, a sorbent system, the sodium chloride container, and optionally solutes other than sodium introduced to the conduit of the controlled compliant flow path.

36. The system of claim 32, wherein a volume of a physiologically compatible solution to provide a bolus of fluid to a subject receiving a blood dialysis, hemofiltration or fluid removal treatment is produced by the system from water introduced to a conduit of the controlled compliant flow path, a sorbent system and the sodium chloride container, and optionally solutes other than sodium introduced to a conduit of the controlled compliant flow path.

37. The system of claim 32, wherein the volume of a physiologically compatible solution to provide solution for return of blood from an extracorporeal flow path to a subject receiving a blood dialysis or fluid removal treatment is produced by the system from water introduced to a conduit of the controlled compliant flow path, a sorbent system and the sodium chloride container, and optionally solutes other than sodium introduced to the conduit of the controlled compliant flow path.

38. The system of claim 33, wherein the physiologically compatible priming solution delivered from the common reservoir to a conduit of the controlled compliant flow path is in fluid communication with an extracorporeal flow path for priming of the extracorporeal flow path wherein the priming solution is passed through a sorbent system and at least a microbial filter or a dialyzer membrane.

39. The system of claim 33, wherein a volume of solution is returned to the common reservoir from an extracorporeal flow path when blood from a subject is introduced to the extracorporeal flow path.

40. The system of claim 4, wherein the buffer source container contains bicarbonate.

41. The system of claim 4, wherein the salination valve is periodically switched to direct fluid flow through the buffer source container to infuse a desired amount of buffer into the fluid.

42. The system of claim 4, wherein a physiologically compatible solution is continually prepared by the system until a predetermined volume of solution has been produced and reserved in a solution reservoir.

43. The system of claim 1, further comprising a filter positioned downstream from the at least one container wherein the microbial filter removes undissolved particulates/aggregates and any contaminants contained in the at least one container.

44. A method for generating a physiologically compatible fluid, comprising the steps of:
preparing the physiologically compatible fluid from water using the system of claim 1 wherein the controlled compliant flow path modifies water into any one of a solution for priming a blood system, a solution for flushing or rinsing a dialyzer or an extracorporeal flow path, a physiologically compatible solution for contacting blood, a physiologically compatible solution for bolus infusion to a subject, and a solution for blood rinse back to a subject.

45. The method of claim 44, wherein the at least one container comprises a first container and a second container, wherein the first container is a sodium chloride cartridge and the second container is a buffer source cartridge, and generating a predetermined concentration of sodium ion and buffer from the sodium chloride cartridge and the buffer source cartridge.

46. The method of claim 45, further comprising the step of:
generating a physiologically compatible priming solution; and
storing the physiologically compatible priming solution in a therapy solution reservoir using a control pump on the controlled compliant flow path.

47. The method of claim 45, further comprising the step of:
generating a physiologically compatible bolus infusion solution; and
storing the physiologically compatible bolus infusion solution in a therapy solution reservoir using a control pump on the controlled compliant flow path.

48. The method of claim 45, further comprising the step of:
generating a physiologically compatible rinse-back solution; and
storing the physiologically compatible rinse-back solution in a therapy solution reservoir using a control pump on the controlled compliant flow path.

49. A method for generating a physiologically compatible fluid, comprising the steps of:
providing water to the system of claim 1, wherein the controlled compliant flow path is in fluid communication with an extracorporeal flow path across a semipermeable membrane;
configuring the system to bypass the extracorporeal flow path, the system having a bypass conduit flow path for conveying fluid through a first segment of the controlled compliant flow path without contacting the semipermeable membrane;
conveying the water through the conditioning flow path;
reconstituting an electrolyte source to generate a physiologically compatible fluid, and conveying the fluid through the first segment of the controlled compliant flow path.

50. The method of claim 49 wherein the dissolved gas is removed from the water.

51. The method of claim 49 wherein the conditioning flow path has a buffer source cartridge.

52. The method of claim 51 wherein the buffer source cartridge is an interchangeable bicarbonate cartridge.

53. The method of claim 49, wherein the conditioning flow path has a sodium conduit flow path with a sodium source configured in parallel with a buffer source conduit flow path with a buffer source.

54. The method of claim 49, further comprising the steps of:
sensing fluid conductivity using a conductivity sensor; and
operating a water pump to add water to reduce a sodium level or, alternatively, controlling the salination valve on the conditioning flow path to direct flow through the sodium chloride container and operating the salination pump to infuse a sodium chloride concentrate into the fluid to increase a sodium level in the controlled compliant flow path.

55. The method of claim 49, wherein a pump rate of the salination pump is adjusted, at least in part, according to the conductivity readings to maintain a desired sodium chloride concentration in the controlled compliant flow path.

56. The method of claim 49, further comprising the step of sensing a temperature of the fluid in the conditioning flow path using a temperature sensor and wherein a pump rate of the salination pump is adjusted, at least in part, according to the temperature readings to achieve a desired rate of sodium or buffer infusion to the controlled compliant flow path.

57. The method of claim 49 further comprising determining the fluid flow rate in the controlled compliant flow path and adjusting the rate of the salination pump, at least in part, based on the fluid flow rate in the controlled compliant flow path.

* * * * *